United States Patent
Chu

(10) Patent No.: US 12,215,171 B2
(45) Date of Patent: Feb. 4, 2025

(54) RABBIT ANTIBODIES TO HUMAN IMMUNOGLOBULINS G

(71) Applicant: Genzyme Corporation, Cambridge, MA (US)

(72) Inventor: Ruiyin Chu, Westborough, MA (US)

(73) Assignee: Genzyme Corporation, Cambridge, MA (US)

( * ) Notice: Subject to any disclaimer, the term of this patent is extended or adjusted under 35 U.S.C. 154(b) by 821 days.

(21) Appl. No.: 17/335,291

(22) Filed: Jun. 1, 2021

(65) Prior Publication Data

US 2021/0380719 A1 Dec. 9, 2021

Related U.S. Application Data

(60) Provisional application No. 63/033,073, filed on Jun. 1, 2020.

(51) Int. Cl.
*C07K 16/42* (2006.01)
*G01N 33/68* (2006.01)

(52) U.S. Cl.
CPC ....... *C07K 16/4241* (2013.01); *G01N 33/686* (2013.01); *C07K 2317/20* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,766,251 B2 | 9/2017 | Essig et al. | |
| 2013/0052668 A1* | 2/2013 | Paulovich | G01N 33/6893 422/69 |

FOREIGN PATENT DOCUMENTS

| | | |
|---|---|---|
| EP | 0161638 A2 | 11/1985 |
| WO | 00/09560 | 2/2000 |

OTHER PUBLICATIONS

Weber et al., 2017, Exp. Mol. Med. 49, e305, doi:10.1038/emm.2017.23; pp. 1-12.*
Chu et al., "Capture-Stabilize Approach for Membrane Protein SPR Assays," Sci Rep. (2015) 4:7360, pp. 1-9.
Chu et al., "Development of Rabbit Monoclonal Antibodies for Quantitation of Therapeutic Human Antibodies in Preclinical Non-Human Primate Studies", Monoclonal Antibodies In Immunodiagnosis and Immunotherapy (2020) 39 (5):175-83.
Fraley et al., "The GyrolabTM Immunoassay System: a Platform for Automated Bioanalysis and Rapid Sample Turnaround," Bioanalysis (2013) 5:1765-74.
Iwasaki et al., "Importance of Cynomolgus Monkeys in Development of Monoclonal Antibody Drugs, "Drug Metab Pharmacokinet. (2019) 34:55-63.
Seeber et al., PLoS One (2014) 9:e86184; Rashidian et al., "Single B Cell Cloning and Production of Rabbit Monoclonal Antibodies" in: Zielonka and Krah (eds) Genotype Phenotype Coupling. Methods in Molecular Biology, vol. 2070, Humana, New York, NY, 2020, pp. 423-441.
Sievers et al., "Fast, Scalable Generation of High-Quality Protein Multiple Sequence Alingments Using Clustal Omega," Mol Syst Biol. (2011) 7:539, pp. 1-6.
Stubenrauch et al., "Evaluation of an Immunoassay for Human-Specific Quantitation of Therapeutic Antibodies in Serum Samples from Non-Human Primates," J Pharm Biomed Anal. (2009) 49:1003-8.
Sulka et al, "Correlation of Lyme Disease-Associated IgG4 Autoantibodies Correlate with Synovial Pathology in Antibiotic-Refractory Lyme Arthritis," Arthritis Rheumatol (2018) 70(11):1835-46.
Wu et al., "Trispecific Antibodies Enhance the Therapeutic Efficacy of Tumor-Directed T Cells Through T Cell Receptor Co-Stimulation," Nat Cancer (2020) 1:86-98.
Zhang et al., "Advances in the Isolation of Specific Monoclonal Rabbit Antibodies," Front Immunol. (2017) 8:494, pp. 1-6.
Zhang et al., "Humanization of Rabbit Monoclonal Antibodies via Grafting Combined Kabat/IMGT/ Paratome Complementarity-Determining Regions: Rationale and Examples," MABS (2017) 9(3):419-29.
Product Data Sheet, "Anti-human IgGI Rabbit Monoclonal Antibody, Clone RM117—RevMAb," (2018) 1 page. https://www.revmab.com/index.php/product/anti-human-igg1-rabbit-monoclonal-antibody-clone-rm117/.
Product Data Sheet "Anti-human IgG2 Rabbit Monoclonal Antibody, Clone RM118—RevMAb," (2018) 1 page. https://www.revmab.com/index.php/product/anti-human-igg2-rabbit-monoclonal-antibody-clone-rm118/.
Product Data Sheet, "Anti-human IgG4 Rabbit Monoclonal Antibody, clone RM120—RevMAb," (2018) 1 page. https://www.revmab.com/index.php/product/anti-human-igg4-rabbit-monoclonal-antibody-clone-rm120/.
Berry et al., "Substitution of cysteine for selenocysteine in type I iodothyronine deiodinase reduces the catalytic efficiency of the protein but enhances its translation," Endocrinology (1992) 131(4):1848-1852.
Gasser et al., "Antibody production with yeasts and filamentous fungi: on the road to large scale?" Biotechnology Letters (2007) 29:201-212.

* cited by examiner

*Primary Examiner* — Elizabeth C. Kemmerer

(74) *Attorney, Agent, or Firm* — Steptoe LLP; Z. Ying Li; Ron Vogel

(57) ABSTRACT

This disclosure anti-human IgG antibodies and antigen-binding portions thereof derived from rabbits and methods of using these antibodies and portions.

22 Claims, 10 Drawing Sheets

Specification includes a Sequence Listing.

```
                        Leader 1-19 aa      ➤ Variable domain 20-141 aa
hIgG_Fab_16F5_H    METGLRWLLLVAVLKGVQCQQQLEESGGGLVKPGGTLTLTCKASGIDFSNYYYMCWVRQA    60
hIgG_Fab_11F9_H    METGLRWLLLVAVLKGVQCQQQLEESGGGLVQPEGSLTLTCIASGFSFSSSHWICWVRQA    60
hIgG_Fab_9E6_H     METGLRWLLLVAVLKGVQCQS-LEESGGDLVKPGASLTLTCKASGFDFSSSYYMCWVRQA    59
hIgG_Fab_11G5_H    METGLRWLLLVAVLKGVQCQS-LEESGGDLVKPGASLTLTCTASGFSFSSSYYMCWVRQA    59
hIgG_Fab_2C5_H     METGLRWLLLVTVLKGVQCQEQLVESGGGLVKPGASLTLTCTASGFSFSSGYYMCWVRQA    60
hIgG_Fab_19B1_H    METGLRWLLLVAVLKGVQCQEQLVESGGGLVKPGSLTLTCTASGFSFSDSYYMCWVRQA    60
                   *******.****. * **.:.:* .:**. *:.**. ::.*:**** hIgG_Fab_16F5_H    PGKGLELIACIYTGSSGSTWYATWAKGRFTISKTSSTTVTLQMTSLTAADTATYFCARDR    120
hIgG_Fab_11F9_H    PGKGLEWIACMSTS-SGSTYDANWAKGRFTISKTSSTTVTLQMTSLTAADTATYFCARD-    118
hIgG_Fab_9E6_H     PG--RLEWIACIYGGGLSNTYYAGWAKGRFTISKTSSTTVTLQMTSLTVADTATYFCARD-    117
hIgG_Fab_11G5_H    PGKRLEWIACIYGGGLSNTYYAGWAKGRFTISKTSSTTVTLQMTSLTAADTATYFCARD-    118
hIgG_Fab_2C5_H     PGKGLEWIACIYGGALTNTYYATWAKGRFTISKTSSTTVTLQMTSLTAADTATYFCARD-    119
hIgG_Fab_19B1_H    PGKGLEWIACIYGGTITNTYYASWAKGRFTISKTSSTTVTLQMTSLTAADTATYFCARD-    119
                   **  ** ***:  .   .*:  *  * ************** ********.*********

➤Constant region 142 aa - end
hIgG_Fab_16F5_H    DVGSLYDSLDLWGQGTLVTVSPGQPKAPSVFPLAPCCGDTPSSTVTLGCLVKGYLPEPVT    180
hIgG_Fab_11F9_H    -VGGSTTYFDLWGPGTLVTVSSGQPKAPSVFPLAPCCGDTPSSTVTLGCLVKGYLPEPVT    177
hIgG_Fab_9E6_H     -AGTSGDYLNLWGPGTLVTVSSGQPKAPSVFPLAPCCGDTPSSTVTLGCLVKGYLPEPVT    176
hIgG_Fab_11G5_H    -AGTSGDYLNLWGPGTLVTVSSGQPKAPSVFPLAPCCGDTPSSTVTLGCLVKGYLPEPVT    177
hIgG_Fab_2C5_H     -LGAAGDAYNLWGQGTLVTVSSGQPKAPSVFPLAPCCGDTPSSTVTLGCLVKGYLPEPVT    178
hIgG_Fab_19B1_H    -LGAAGDAYNLWGPGTLVTVSSGQPKAPSVFPLAPCCGDTPSSTVTLGCLVKGYLPEPVT    178
                    *     ;* ** * ************************************** hIgG_Fab_16F5_H    VTWNSGTLTNGVRTFPSVRQSSGLYSLSSVVSVTSSSQPVTCNVAHPATNTKVDKTVAPS    240
hIgG_Fab_11F9_H    VTWNSGTLTNGVRTFPSVRQSSGLYSLSSVVSVTSSSQPVTCNVAHPATNTKVDKTVAPS    237
hIgG_Fab_9E6_H     VTWNSGTLTNGVRTFPSVRQSSGLYSLSSVVSVTSSSQPVTCNVAHPATNTKVDKTVAPS    236
hIgG_Fab_11G5_H    VTWNSGTLTNGVRTFPSVRQSSGLYSLSSVVSVTSSSQPVTCNVAHPATNTKVDKTVAPS    237
hIgG_Fab_2C5_H     VTWNSGTLTNGVRTFPSVRQSSGLYSLSSVVSVTSSSQPVTCNVAHPATNTKVDKTVAPS    238
hIgG_Fab_19B1_H    VTWNSGTLTNGVRTFPSVRQSSGLYSLSSVVSVTSSSQPVTCNVAHPATNTKVDKTVAPS    238
                   ************************************************************ hIgG_Fab_16F5_H    TCSKPMCPPPELPGGPSVFIFPPKPKDTLMISRTPEVTCVVVDVSQDDPEVQFTWYINNE    300
hIgG_Fab_11F9_H    TCSKPMCPPPELPGGPSVFIFPPKPKDTLMISRTPEVTCVVVDVSQDDPEVQFTWYINNE    297
hIgG_Fab_9E6_H     TCSKPMCPPPELPGGPSVFIFPPKPKDTLMISRTPEVTCVVVDVSQDDPEVQFTWYINNE    296
hIgG_Fab_11G5_H    TCSKPMCPPPELPGGPSVFIFPPKPKDTLMISRTPEVTCVVVDVSQDDPEVQFTWYINNE    297
hIgG_Fab_2C5_H     TCSKPMCPPPELPGGPSVFIFPPKPKDTLMISRTPEVTCVVVDVSQDDPEVQFTWYINNE    298
hIgG_Fab_19B1_H    TCSKPMCPPPELPGGPSVFIFPPKPKDTLMISRTPEVTCVVVDVSQDDPEVQFTWYINNE    298
                   ************************************************************ hIgG_Fab_16F5_H    QVRTARPPLREQQFNSTIRVVSTLPIAHQDWLRGKEFKCKVHNKALPAPIEKTISKARGQ    360
hIgG_Fab_11F9_H    QVRTARPPLREQQFNSTIRVVSTLPIAHQDWLRGKEFKCKVHNKALPAPIEKTISKARGQ    357
hIgG_Fab_9E6_H     QVRTARPPLREQQFNSTIPVVSTLPIAHQDWLRGKEFKCKVHNKALPAPIEKTISKARGQ    356
hIgG_Fab_11G5_H    QVRTARPPLREQQFNSTIRVVSTLPIAHQDWLRGKEFKCKVHNKALPAPIEKTISKARGQ    357
hIgG_Fab_2C5_H     QVRTARPPLREQQFNSTIRVVSTLPIAHQDWLRGKEFKCKVHNKALPAPIEKTISKARGQ    358
hIgG_Fab_19B1_H    QVRTARPPLREQQFNSTIRVVSTLPIAHQDWLRGKEFKCKVHNKALPAPIEKTISKARGQ    358
                   ************************************************************ hIgG_Fab_16F5_H    PLEPKVYTMGPPREELSSRSVSLTCMINGFYPSDISVEWEKNGKAEDNYKTTPTVLDSDG    420
hIgG_Fab_11F9_H    PLEPKVYTMGPPREELSSRSVSLTCMINGFYPSDISVEWEKNGKAEDNYKTTPTVLDSDG    417
hIgG_Fab_9E6_H     PLEPKVYTMGPPREELSSRSVSLTCMINGFYPSDISVEWEKNGKAEDNYKTTPTVLDSDG    416
hIgG_Fab_11G5_H    PLEPKVYTMGPPREELSSRSVSLTCMINGFYPSDISVEWEKNGKAEDNYKTTPTVLDSDG    417
hIgG_Fab_2C5_H     PLEPKVYTMGPPREELSSRSVSLTCMINGFYPSDISVEWEKNGKAEDNYKTTPTVLDSDG    418
hIgG_Fab_19B1_H    PLEPKVYTMGPPREELSSRSVSLTCMINGFYPSDISVEWEKNGKAEDNYKTTPTVLDSDG    418
                   ************************************************************ hIgG_Fab_16F5_H    SYFLYSKLSVPTSEWQRGDVFTCSVMHEALHNHYTQKSISRSPGK*    465    (SEQ ID NO:67)
hIgG_Fab_11F9_H    SYFLYSKLSVPTSEWQRGDVFTCSVMHEALHNHYTQKSISRSPGK*    462    (SEQ ID NO:65)
hIgG_Fab_9E6_H     SYFLYSKLSVPTSEWQRGDVFTCSVMHEALHNHYTQKSISRSPGK*    461    (SEQ ID NO:64)
hIgG_Fab_11G5_H    SYFLYSKLSVPTSEWQRGDVFTCSVMHEALHNHYTQKSISRSPGK*    462    (SEQ ID NO:66)
hIgG_Fab_2C5_H     SYFLYSKLSVPTSEWQRGDVFTCSVMHEALHNHYTQKSISRSPGK*    463    (SEQ ID NO:63)
hIgG_Fab_19B1_H    SYFLYSKLSVPTSEWQRGDVFTCSVMHEALHNHYTQKSISRSPGK*    463    (SEQ ID NO:68)
                   *********************************************
```

FIG. 2A

```
                    Leader: 1-22 aa        Variable domain 23-132 aa
hIgG_Fab_9E6_L    MDTRAPTQLLGLLLLWLPGARCAVVMTQTASPVSGAVGGTVTINCQASQSISSSYLSWYQ    60
hIgG_Fab_11G5_L   MDTRAPTQLLGLLLLWLPGARCAVVMTQTASPVSGAVGGTVTINCQASQSISASALSWYQ   60
hIgG_Fab_2C5_L    MDTRAPTQLLGLLLLWLPGARCASDMTQTPASVSAAVGGTVTIKCQASESIYS-GLAWYQ   59
hIgG_Fab_19B1_L   MDTRAPTQLLGLLLLWLPGARCASDMTQTPASVSEPVGGTVTIKCQASENIYS-SLAWYQ   59
hIgG_Fab_11F9_L   MDTRAPTQLLGLLLLWLPGARCAYDMTQTPASVSEPVGGTVTIKCQASQSISN-ELSWYQ   59
hIgG_Fab_16F5_L   MDTRAPTQLLGLLLLWLPGARCAYDMTQTPASVEAAVGGTVTINCQASQSINN-WLSWYQ   59
                  *************  ** :.*  ****;*:.*    *:*:*** hIgG_Fab_9E6_L    QKPGQPPKLLIYGASTLASGVPSRFKGSGSGTQFTLTISGVQCDDAATYYCAYDAYRLSS   120
hIgG_Fab_11G5_L   QKPGQPPKLLIYAASTLESGVPSRFKGSGSGTQFTLTISGVQCDDAATYYCAYDGYRLSS   120
hIgG_Fab_2C5_L    QKPGQPPKLLIFDASDLASGVPSRFKGSRSETEYTLTISDLECADAATYCQC-TDRNSI    118
hIgG_Fab_19B1_L   QKPGQPPKLLIYDASNLASGVPSRFKGSGSGTEFTLTISDLECADAATYCQC-TYRSSS    118
hIgG_Fab_11F9_L   QKPGQPPKLLIYRASTLASGVPSRFKGSGSGTQFTLTINGVECADAATYCQQ-GYSISN    118
hIgG_Fab_16F5_L   QKPGQRPKLLIYQASTLASGVSSRFKGSGSGTHFTLTISDLECADAATYCQQ-GWSIDD    118
                  ***** ** ****   ** ****** *  * **** **  **** **  *  *
                       Constant region 133 aa - end
hIgG_Fab_9E6_L    PDNIFGGGTEVVVKGDPVAPTVLIFPPAADQVATGTVTIVCVANKYFPDVTVTWEVDGTT   180
hIgG_Fab_11G5_L   ADNIFGGGTEVVVKGDPVAPTVLIFPPAADQVATGTVTIVCVANKYFPDVTVTWEVDGTT   180
hIgG_Fab_2C5_L    TSYAFGGGTEVVVKGDPVAPTVLIFPPAADQVATGTVTIVCVANKYFPDVTVTWEVDGTT   178
hIgG_Fab_19B1_L   SSYAFGGGTEVVVKGDPVAPTVLIFPPAADQVATGTVTIVCVANKYFPDVTVTWEVDGTT   178
hIgG_Fab_11F9_L   VDNTFGGGTEVVVKGDPVAPTVLIFPPAADQVATGTVTIVCVANKYFPDVTVTWEVDGTT   178
hIgG_Fab_16F5_L   IDNAFGGGTEVVVKGDPVAPTVLIFPPAADQVATGTVTIVCVANKYFPDVTVTWEVDGTT   178
                      *************************************************** hIgG_Fab_9E6_L    QTTGIENSKTPQNSADCTYNLSSTLTLTSTQYNSHKEYTCKVTQGTTSVVQSFNRGDC*   238  (SEQ ID NO:70)
hIgG_Fab_11G5_L   QTTGIENSKTPQNSADCTYNLSSTLTLTSTQYNSHKEYTCKVTQGTTSVVQSFNPGDC*   238  (SEQ ID NO:72)
hIgG_Fab_2C5_L    QTTGIENSKTPQNSADCTYNLSSTLTLTSTQYNSHKEYTCKVTQGTTSVVQSFNPGDC*   236  (SEQ ID NO:69)
hIgG_Fab_19B1_L   QTTGIENSKTPQNSADCTYNLSSTLTLTSTQYNSHKEYTCKVTQGTTSVVQSFNPGDC*   236  (SEQ ID NO:74)
hIgG_Fab_11F9_L   QTTGIENSKTPQNSADCTYNLSSTLTLTSTQYNSHKEYTCKVTQGTTSVVQSFNRGDC*   236  (SEQ ID NO:71)
hIgG_Fab_16F5_L   QTTGIENSKTPQNSADCTYNLSSTLTLTSTQYNSHKEYTCKVTQGTTSVVQSFNRGDC*   236  (SEQ ID NO:73)
                  *********************************************************
```

FIG. 2B

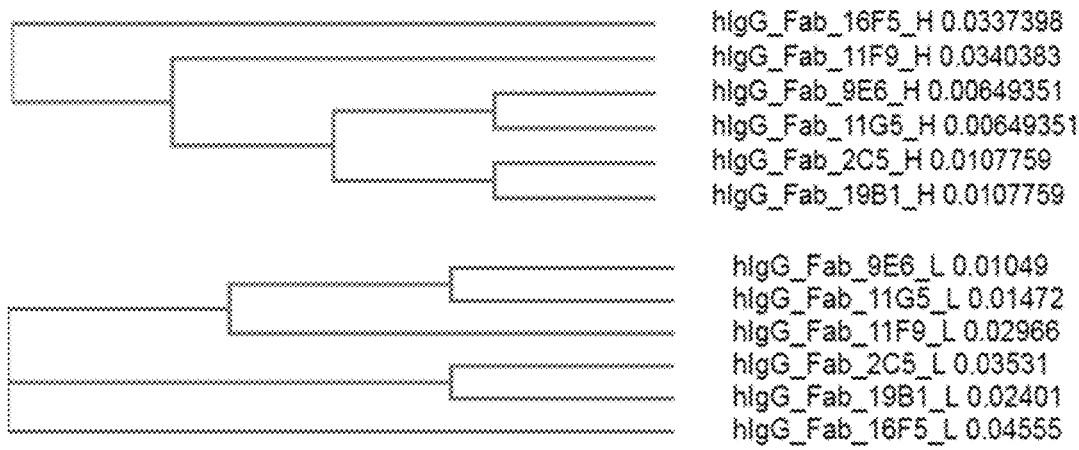

FIG. 2C

Quality Controls

| Identity | Expected Conc. [ng/mL] | Response | S/B | Calc Conc [ng/mL] | Average Conc [ng/mL] | CV Conc [%] | Bias [%] | Average Bias [%] | Average Response | CV Response [%] | Dilution | CD ID | CD Struct |
|---|---|---|---|---|---|---|---|---|---|---|---|---|---|
| MQC | 0.600 | 5.88 | 1.38 | 0.657 | 0.647 | 2.27 | 9.55 | 7.92 | 5.85 | 0.566 | 1.00 | 0004321-183 | C5 |
| MQC | 0.600 | 5.83 | 1.38 | 0.637 | 0.647 | 2.17 | 6.10 | 7.92 | 5.85 | 0.566 | 1.00 | 0004321-183 | C6 |
| LQC | 40.0 | 68.6 | 15.0 | 34.8 | 35.9 | 4.30 | -13.0 | -10.2 | 70.3 | 3.48 | 1.00 | 0004321-183 | C3 |
| LQC | 40.0 | 72.0 | 15.8 | 37.0 | 35.9 | 4.30 | -7.52 | -10.2 | 70.3 | 3.48 | 1.00 | 0004321-183 | C4 |
| HQC | 750 | 409 | 87.7 | 680 | 739 | 20.9 | -9.32 | 6.44 | 414 | 4.56 | 1.00 | 0004321-183 | C1 |
| HQC | 750 | 427 | 93.6 | 937 | 798 | 20.9 | 32.2 | 6.44 | 414 | 4.56 | 1.00 | 0004321-183 | C3 |

FIG. 4C

FIG. 5A  Overlay Graph
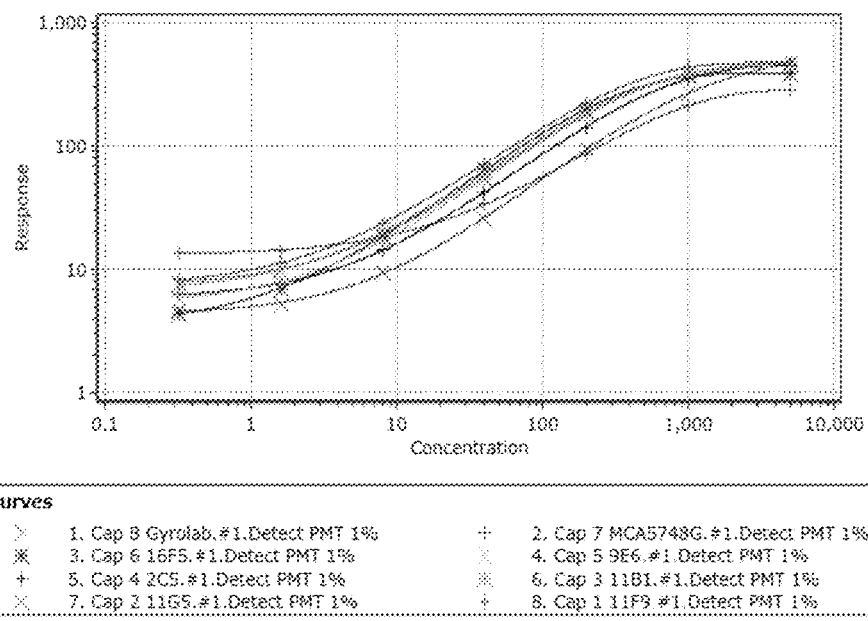
FIG. 5B  Overlay Graph
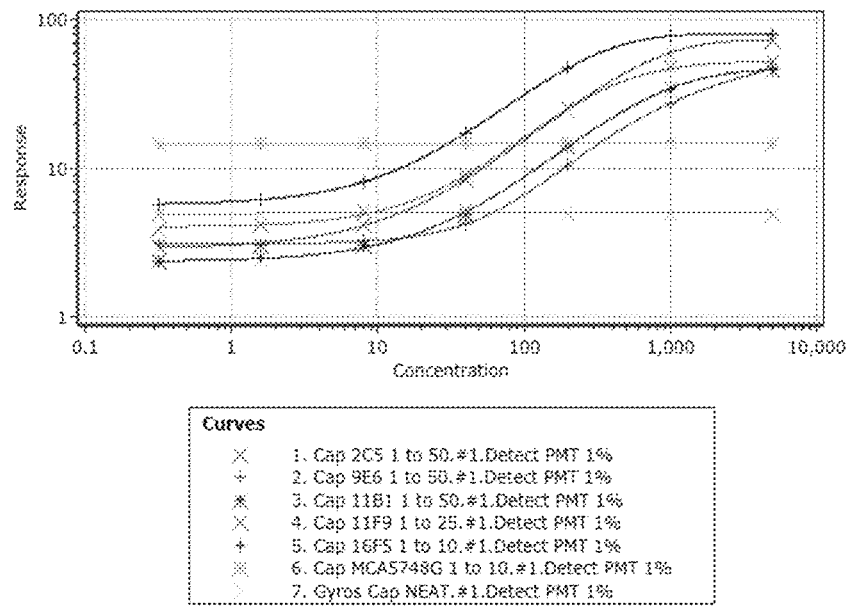

SEQUENCE LISTING

```
<160> NUMBER OF SEQ ID NOS: 74

<210> SEQ ID NO 1
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggagactg ggctgcgctg gcttctcctg gtcactgtgc tcaaaggtgt ccagtgtcag      60
gagcagctgg tggagtccgg gggagacctg gtcaagcctg gggcatccct gacactcacc     120
tgcacagcct ctggattctc cttcagtagc ggctactaca tgtgctgggt ccgccaggct     180
ccagggaagg ggctggagtg gatcgcatgc atttatggtg gtgcgcttac taatacttac     240
tacgcgacct gggcgaaagg ccgattcacc atctccaaga cctcgtcgac cacggtgacc     300
ctgcaaatga ccagtctgac agccgcggac acggccacct atttctgtgc gagagatctg     360
ggtgctgctg gtgatgctta taacttgtgg gggccaggca ccctggtcac cgtctcctca     420
```

```
gggcaaccta aggctccatc agtcttccca ctggcccct gctgcgggga cacacccagc    480
tccacggtga ccctgggctg cctggtcaaa ggctacctcc cggagccagt gaccgtgacc    540
tggaactcgg gcaccctcac caatggggta cgcaccttcc cgtccgtccg gcagtcctca    600
ggcctctact cgctgagcag cgtggtgagc gtgacctcaa gcagccagcc cgtcacctgc    660
aacgtggccc acccagccac caacaccaaa gtggacaaga ccgttgcgcc ctcgacatgc    720
agcaagccca tgtgcccacc ccctgaactc ccggggggac cgtctgtctt catcttcccc    780
ccaaaaccca aggacaccct catgatctca cgcaccccg aggtcacatg cgtggtggtg     840
gacgtgagcc aggatgaccc cgaggtgcag ttcacatggt acataaacaa cgagcaggtg    900
cgcaccgccc ggccgccgct acgggagcag cagttcaaca gcacgatccg cgtggtcagc    960
accctcccca tcgcgcacca ggactggctg aggggcaagg agttcaagtg caaagtccac   1020
aacaaggcac tcccggcccc catcgagaaa accatctcca agccagagg gcagcccctg    1080 gagccgaagg tctacaccat gggccctccc cgggaggagc tgagcagcag gtcggtcagc   1140
ctgacctgca tgatcaacgg cttctaccct tccgacatct cggtggagtg ggagaagaac   1200
gggaaggcag aggacaacta caagaccacg ccgaccgtgc tggacagcga cggctcctac   1260
ttcctctaca gcaagctctc agtgcccacg agtgagtggc agcggggcga cgtcttcacc   1320
tgctccgtga tgcacgaggc cttgcacaac cactacacgc agaagtccat ctcccgctct   1380
ccgggtaaat ag                                                        1392

<210> SEQ ID NO 2
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggagactg gctgcgctg cttctcctg gtcgctgtgc tcaaaggtgt ccagtgtcag       60
tcgttggagg agtccggggg agacctggtc aagcctgggg catccctgac actcacctgc    120
aaagcctctg gattcgactt cagtagcagc tactacatgt gctgggtccg ccaggctcca    180
gggagactgg agtggatcgc atgcatttat ggtggtggtc tgagtaacac ttactacgcg    240
ggctgggcaa aaggccgatt caccatctcc aaaacctcgt cgaccacggt gactctgcaa    300
atgaccagtc tgacagtcgc ggacacggcc acctatttct gtgcgagaga tgctgggact    360
agtggtgatt accttaactt gtggggcccg ggcaccctgg tcaccgtctc ctcagggcaa    420
cctaaggctc catcagtctt cccactggcc cctgctgcg gggacacacc cagctccacg    480
gtgaccctgg gctgcctggt caaaggctac ctcccggagc cagtgaccgt gacctggaac    540
tcgggcaccc tcaccaatgg ggtacgcacc ttcccgtccg tccggcagtc ctcaggcctc    600
tactcgctga gcagcgtggt gagcgtgacc tcaagcagcc agcccgtcac ctgcaacgtg    660
gcccacccag ccaccaacac caaagtggac aagaccgttg cgcctcgac atgcagcaag     720 cccatgtgcc caccccctga actcccgggg gaccgtctgt cttcatcttc cccccaaaa    780 cccaaggaca ccctcatgat ctcacgcacc cccgaggtca catgcgtggt ggtggacgtg   840
agccaggatg accccgaggt gcagttcaca tggtacataa acaacgagca ggtgcgcacc   900
gcccggccgc cgctacggga gcagcagttc aacagcacga tccgcgtggt cagcaccctc   960
cccatcgcgc accaggactg gctgaggggc aaggagttca gtgcaaagt ccacaacaag   1020
```

```
gcactcccgg cccccatcga gaaaaccatc tccaaagcca gagggcagcc cctggagccg      1080
aaggtctaca ccatgggccc tccccgggag gagctgagca gcaggtcggt cagcctgacc      1140
tgcatgatca acggcttcta cccttccgac atctcggtgg agtgggagaa gaacgggaag      1200
gcagaggaca actacaagac cacgccgacc gtgctggaca cgacggctc ctacttcctc       1260 tacagcaagc tctcagtgcc cacgagtgag tggcagcggg gcgacgtctt cacctgctcc      1320
gtgatgcacg aggccttgca caaccactac acgcagaagt ccatctcccg ctctccgggt      1380
aaatag                                                                  1386

<210> SEQ ID NO 3
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggagactg ggctgcgctg gcttctcctg gtcgctgtgc tcaaaggtgt ccagtgtcag       60
cagcagctgg aggagtccgg gggaggcctg gtccagcctg agggatccct gacactcacc      120
tgcatagctt ctggattctc cttcagtagc agccactgga tatgttgggt ccgccaggct      180
ccagggaagg ggctggagtg gatcgcatgc atgtctacta gtagtggtag cacttacgat      240
gcgaactggg cgaaaggccg attcaccatc tccaaaacct cgtcgaccac ggtgactctg      300
caaatgacca gtctgacagc cgcggacacg gccacctatt tctgtgcgag agatgttggc      360
ggtagtacta cttactttga cttgtggggc ccaggcaccc tggtcaccgt ctcctcaggg      420
caacctaagg ctccatcagt cttcccactg gccccctgct gcggggacac acccagctcc      480
acggtgaccc tgggctgcct ggtcaaaggc tacctcccgg agccagtgac cgtgacctgg      540
aactcgggca ccctcaccaa tggggtacga accttcccgt ccgtccggca gtcctcaggc      600
ctctactcgc tgagcagcgt ggtgagcgtg acctcaagca gccagcccgt cacctgcaac      660
gtggcccacc cagccaccaa caccaaagtg gacaagacct tgcgccctc gacatgcagc      720 aagcccatgt gcccaccccc tgaactcccg ggggaccgt ctgtcttcat cttcccccca      780
aaacccaagg acaccctcat gatctcacgc acccccgagg tcacatgcgt ggtggtggac      840
gtgagccagg atgaccccga ggtgcagttc acatggtaca taaacaacga gcaggtgcgc      900 accgccggc cgccgctacg ggagcagcag ttcaacagca cgatccgcgt ggtcagcacc       960
ctccccatcg cgcaccagga ctggctgagg ggcaaggagt tcaagtgcaa agtccacaac      1020
aaggcactcc cggcccccat cgagaaaacc atctccaaag ccagagggca gccctggag      1080 ccgaaggtct acaccatggg ccctcccgg gaggagctga gcagcaggtc ggtcagcctg      1140
acctgcatga tcaacggctt ctacccttcc gacatctcgg tggagtggga agaacggg       1200 aaggcagagg acaactacaa gaccacgccg accgtgctgg acagcgacgg ctcctacttc      1260
ctctacagca agctctcagt gcccacgagt gagtggcagc ggggcgacgt cttcacctgc      1320
tccgtgatgc acgaggcctt gcacaaccac tacacgcaga gtccatctc ccgctctccg       1380 ggtaaatag                                                               1389

<210> SEQ ID NO 4
<211> LENGTH: 1389
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 4
atggagactg ggctgcgctg gcttctcctg gtcgctgtgc tcaaaggtgt ccagtgtcag    60
tcgttggagg agtccggggg agacctggtc aagcctgggg catccctgac actcacctgc   120
acagcttctg gattctcctt cagtagcagc tactacatgt gctgggtccg ccaggctcca   180
gggaagaggc tggagtggat cgcttgcatt tatggtggtg gtctgagtaa cacttactac   240
gcgggctggg caaaaggccg attcaccatc tccaaaacct cgtcgaccac ggtgactctg   300
caaatgacca gtctgacagc cgcggacacg gccaccattt tctgtgcgag agatgctggg   360
actagtggtg attaccttaa cttgtggggc ccaggcaccc tggtcaccgt ctcctcaggg   420
caacctaagg ctccatcagt cttcccactg gccccctgct gcgggacac acccagctcc   480 acggtgaccc tgggctgcct ggtcaaaggc tacctcccgg agccagtgac cgtgacctgg   540
aactcgggca ccctcaccaa tggggtacgc accttcccgt ccgtcggca gtcctcaggc   600 ctctactcgc tgagcagcgt ggtgagcgtg acctcaagca gccagcccgt cacctgcaac   660
gtggcccacc cagccaccaa caccaaagtg acaagaccg ttgcgccctc gacatgcagc   720
aagcccatgt gcccaccccc tgaactcccg ggggaccgt ctgtcttcat cttcccccca   780
aaacccaagg acaccctcat gatctcacgc accccgagg tcacatgcgt ggtggtggac   840
gtgagccagg atgaccccga ggtgcagttc acatggtaca taaacaacga gcaggtgcgc   900
accgcccggc gccgctacg ggagcagcag ttcaacagca cgatccgcgt ggtcagcacc   960
ctccccatcg cgcaccagga ctggctgagg ggcaaggagt tcaagtgcaa agtccacaac  1020
aaggcactcc cggcccccat cgagaaaacc atctccaaag ccagagggca gccccctggag  1080 ccgaaggtct acaccatggg ccctccccgg gaggagctga gcagcaggtc ggtcagcctg  1140
acctgcatga tcaacggctt ctacccttcc gacatctcgg tggagtggga agaacggg  1200 aaggcagagg acaactacaa gaccacgccg accgtgctgg acagcgacgg ctcctacttc  1260
ctctacagca agctctcagt gcccacgagt gagtggcagc ggggcgacgt cttcacctgc  1320
tccgtgatgc acgaggcctt gcacaaccac tacacgcaga agtccatctc ccgctctccg  1380
ggtaaatag                                                           1389

<210> SEQ ID NO 5
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggagactg ggctgcgctg gcttctcctg gtcgctgtgc tcaaaggtgt ccagtgtcag    60
cagcagttgg aggagtccgg gggaggcctg gtcaagcctg gaggaaccct gacactcacc   120
tgcaaagcct ctggaatcga cttcagtaac tactactaca tgtgctgggt ccgccaggct   180
ccagggaagg ggctggagtt gatcgcatgc atttatactg gtagtagtgg tagcacatgg   240
tacgcgacct gggcgaaggg ccgattcacc atctccaaaa cctcgtcgac cacggtgact   300
ctgcaaatga ccagtctgac agccgcggac acggccacct attttctgtg cgagagatcgt   360 gatgttggta gtctttatga ctccttagat ctctggggcc agggcaccct ggtcaccgtc   420
```

```
tctccagggc aacctaaggc tccatcagtc ttcccactgg ccccctgctg cggggacaca    480
cccagctcca cggtgaccct gggctgcctg gtcaaaggct acctcccgga gccagtgacc    540
gtgacctgga actcgggcac cctcaccaat ggggtacgca ccttcccgtc cgtccggcag    600
tcctcaggcc tctactcgct gagcagcgtg gtgagcgtga cctcaagcag ccagcccgtc    660
acctgcaacg tggcccaccc agccaccaac accaaagtgg acaagaccgt tgcgccctcg    720
acatgcagca gcccatgtg cccaccccct gaactcccgg ggggaccgtc tgtcttcatc    780 ttcccccccaa aacccaagga caccctcatg atctcacgca ccccgaggt cacatgcgtg    840 gtggtggacg tgagccagga tgaccccgag gtgcagttca catggtacat aaacaacgag    900
caggtgcgca ccgcccggcc gccgctacgg gagcagcagt caacagcac gatccgcgtg    960 gtcagcaccc tccccatcgc gcaccaggac tggctgaggg gcaaggagtt caagtgcaaa    1020
gtccacaaca aggcactccc ggcccccatc gagaaaacca tctccaaagc cagagggcag    1080
cccctggagc cgaaggtcta caccatgggc cctccccggg aggagctgag cagcaggtcg    1140
gtcagcctga cctgcatgat caacggcttc taccccttccg acatctcggt ggagtgggag    1200
aagaacggga aggcagagga caactacaag accacgccga ccgtgctgga cagcgacggc    1260
tcctacttcc tctacagcaa gctctcagtg cccacgagtg agtggcagcg gggcgacgtc    1320
ttcacctgct ccgtgatgca cgaggccttg cacaaccact acacgcagaa gtccatctcc    1380
cgctctccgg gtaaatag                                                  1398

<210> SEQ ID NO 6
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atggagactg ggctgcggtg gcttctcctg gtcgctgtgc tcaaaggtgt ccagtgtcag     60
gagcagctgg tggagtccgg gggaggcctg gtccagcctg agggatccct gacactcacc    120
tgcacagctt ctggattctc cttcagtgac agctactaca tgtgctgggt ccgccaggct    180
ccagggaagg ggctgagtg gatcgcatgc atttatggtg gtactattac taatacttac    240
tacgcgagct gggcgaaagg ccgattcacc atctccaaga cctcgtcgac cacggtgacc    300
ctgcaaatga ccagtctgac agccgcggac acggccacct atttctgtgc gagagatctg    360
ggtgctgctg gtgatgctta taacttgtgg ggccaggca ccctggtcac cgtctcctca    420
gggcaaccta aggctccatc agtcttccca ctggcccct gctgcgggga cacccccagc    480
tccacggtga cctgggctg cctggtcaaa ggctacctcc cggagccagt gaccgtgacc    540
tggaactcgg gcaccctcac caatgggta cgcaccttcc cgtccgtccg gcagtcctca    600
ggcctctact cgctgagcag cgtggtgagc gtgacctcaa gcagccagcc cgtcacctgc    660
aacgtggccc acccagccac caacaccaaa gtggacaaga ccgttgcgcc ctcgacatgc    720
agcaagccca tgtgcccacc ccctgaactc ccgggggac cgtctgtctt catcttcccc    780
ccaaaaccca aggacaccct catgatctca cgcaccccg aggtcacatg cgtggtggtg    840
gacgtgagcc aggatgaccc cgaggtgcag ttcacatggt acataaacaa cgagcaggtg    900
cgcaccgccc ggccgccgct acgggagcag cagttcaaca gcacgatccg cgtggtcagc    960 accctccccca tcgcgcacca ggactggctg aggggcaagg agttcaagtg caaagtccac   1020
```

| | |
|---|---|
| aacaaggcac tcccggcccc catcgagaaa accatctcca aagccagagg gcagcccctg | 1080 |
| gagccgaagg tctacaccat gggccctccc cgggaggagc tgagcagcag gtcggtcagc | 1140 |
| ctgacctgca tgatcaacgg cttctaccct tccgacatct cggtggagtg ggagaagaac | 1200 |
| gggaaggcag aggacaacta caagaccacg ccgaccgtgc tggacagcga cggctcctac | 1260 |
| ttcctctaca gcaagctctc agtgcccacg agtgagtggc agcggggcga cgtcttcacc | 1320 |
| tgctccgtga tgcacgaggc cttgcacaac cactacacgc agaagtccat ctcccgctct | 1380 |
| ccgggtaaat ag | 1392 |

<210> SEQ ID NO 7
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

| | |
|---|---|
| atggacacga gggcccccac tcagctgctg ggctcctgc tgctctggct cccaggtgcc | 60 |
| agatgtgcct ctgatatgac ccagactcca gcctccgtgt ctgcagctgt gggaggcaca | 120 |
| gtcaccatca agtgccaggc cagtgagagc atttacagtg gtttggcctg gtatcagcag | 180 |
| aaaccagggc agcctcccaa gctcctgatc tttgatgcat ccgatctggc atctggggtc | 240 |
| ccatcgcggt tcaaaggcag tagatctgag acagagtaca ctctcaccat cagcgacctg | 300 |
| gagtgtgccg atgctgccac ttactactgt caatgcactg atcgtaatag tattacttct | 360 |
| tatgctttcg gcggagggac cgaggtggtg gtcaaaggtg atccagttgc acctactgtc | 420 |
| ctcatcttcc caccagctgc tgatcaggtg gcaactggaa cagtcaccat cgtgtgtgtg | 480 |
| gcgaataaat actttcccga tgtcaccgtc acctgggagg tggatggcac acccaaaca | 540 |
| actggcatcg agaacagtaa aaccgcgca aattctgcag attgtaccta caacctcagc | 600 |
| agcactctga cactgaccag cacacagtac aacagccaca aagagtacac ctgcaaggtg | 660 |
| acccagggca cgacctcagt cgtccagagc ttcaataggg gtgactgtta g | 711 |

<210> SEQ ID NO 8
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

| | |
|---|---|
| atggacacga gggcccccac tcagctgctg ggctcctgc tgctctggct cccaggtgcc | 60 |
| agatgtgccg tcgtgatgac ccagactgca tccccgtgt ctggagctgt gggaggcaca | 120 |
| gtcaccatca attgccaggc cagtcagagt attagtagta gctacttatc ctggtatcag | 180 |
| cagaaaccag gcagcctcc caagctcctg atctatggtg catccactct ggcatctggg | 240 |
| gtcccatcgc ggttcaaagg cagtggatct gggacacagt tcactctcac catcagtggc | 300 |
| gtgcagtgtg acgatgctgc cacttactac tgtgcatacg atgcttatcg tctcagtagt | 360 |
| cctgataata tttcggcgg agggaccgag gtggtggtca aaggtgatcc agttgcacct | 420 |
| actgtcctca tcttcccacc agctgctgat caggtggcaa ctggaacagt caccatcgtg | 480 |
| tgtgtggcga ataaatactt tcccgatgtc accgtcacct gggaggtgga tggcaccacc | 540 |
| caaacaactg gcatcgagaa cagtaaaaca ccgcagaatt ctgcagattg tacctacaac | 600 |

```
<210> SEQ ID NO 9
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atggacacga gggcccccac tcagctgctg gggctcctgc tgctctggct cccaggtgcc      60
agatgtgcct atgatatgac ccagactcca gcctccgtgt ctgaacctgt gggaggcaca     120
gtcaccatca agtgccaggc cagtcagagc attagcaatg aattatcctg gtatcaacaa     180
aaaccagggc agcctcccaa actcctgatc tacagggcat ccactctggc atctggggtc     240
ccatcgcggt tcaaaggcag tggatctggg acacagttca ctctcaccat caacggcgtg     300
gagtgtgccg atgctgccac ttactactgt caacagggtt atagtattag taatgttgat     360
aatactttcg gcggagggac cgaggtggtg gtcaaaggtg atccagttgc acctactgtc     420
ctcatcttcc caccagctgc tgatcaggtg gcaactggaa cagtcaccat cgtgtgtgtg     480
gcgaataaat actttcccga tgtcaccgtc acctgggagg tggatggcac cacccaaaca     540
actggcatcg agaacagtaa aacaccgcag aattctgcag attgtaccta caacctcagc     600
agcactctga cactgaccag cacacagtac aacagccaca aagagtacac ctgcaaggtg     660
acccagggca cgacctcagt cgtccagagc ttcaataggg gtgactgtta g              711

<210> SEQ ID NO 10
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atggacacga gggcccccac tcagctgctg gggctcctgc tgctctggct cccaggtgcc      60
agatgtgccg tcgtgatgac ccagactgca tcccccgtgt ctggagctgt gggaggcaca     120
gtcaccatca attgccaggc cagtcagagt attagtgcta gcgccttatc ctggtatcaa     180
cagaaaccag gcagcctcc caagctcctg atctatgctg catccactct ggaatctggg     240
gtcccatcgc ggttcaaagg cagtggatct gggacacagt tcactctcac catcagcggc     300
gtgcagtgtg acgatgctgc cacttactac tgtgcatacg atggttatcg tctcagtagt     360
gctgataata ttttcggcgg agggaccgag gtggtggtca aggtgatcc agttgcacct     420 actgtcctca tcttcccacc agctgctgat caggtggcaa ctggaacagt caccatcgtg     480
tgtgtggcga ataaatactt tcccgatgtc accgtcacct gggaggtgga tggcaccacc     540
caaacaactg gcatcgagaa cagtaaaaca ccgcagaatt ctgcagattg tacctacaac     600
ctcagcagca ctctgacact gaccagcaca cagtacaaca gccacaaaga gtacacctgc     660
aaggtgaccc agggcacgac ctcagtcgtc cagagcttca atagggtga ctgttag        717

<210> SEQ ID NO 11
<211> LENGTH: 711
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 11

```
atggacacga gggcccccac tcagctgctg gggctcctgc tgctctggct cccaggtgcc    60
agatgtgcct atgatatgac ccagactcca gcctccgtgg aggcagctgt gggaggcaca   120
gtcaccatca attgccaggc cagtcagagc attaataatt ggttatcctg gtatcagcag   180
aaaccagggc agcgtcccaa gctcctgatt taccaggcat ccactctggc atctggggtc   240
tcatcgcggt tcaaaggcag tggatctggg acacacttta ctctcaccat cagcgacctg   300
gagtgtgccg atgctgccac ttactactgt caacagggtt ggagtataga cgatattgat   360
aatgctttcg gcggagggac cgaggtggtg gtcaagggtg atccagttgc acctactgtc   420
ctcatcttcc caccagctgc tgatcaggtg gcaactggaa cagtcaccat cgtgtgtgtg   480
gcgaataaat actttcccga tgtcaccgtc acctgggagg tggatggcac acccaaaca    540
actggcatcg agaacagtaa aacaccgcag aattctgcag attgtaccta caacctcagc   600
agcactctga cactgaccag cacacagtac aacagccaca aagagtacac ctgcaaggtg   660
acccagggca cgacctcagt cgtccagagc ttcaataggg gtgactgtta g            711
```

<210> SEQ ID NO 12
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
atggacacga gggcccccac tcagctgctg gggctcctgc tgctctggct cccaggtgcc    60
agatgtgcct ctgatatgac ccagactcca gcctccgtgt ctgaacctgt gggaggcaca   120
gtcaccatca agtgccaggc cagtgagaac atttacagct ctttagcctg gtatcagcag   180
aaaccagggc agcctcccaa gctcctgatc tatgatgcat ccaatctggc atctggggtc   240
ccatcgcggt tcagcggcag tggatctggg acagagttca ctctcaccat cagcgacctg   300
gagtgtgccg atgctgccac ttactactgt caatgcactt atcgtagtag tagtagttct   360
tatgctttcg gcggagggac cgaggtggtg gtcaaaggtg atccagttgc acctactgtc   420
ctcatcttcc caccagctgc tgatcaggtg gcaactggaa cagtcaccat cgtgtgtgtg   480
gcgaataaat actttcccga tgtcaccgtc acctgggagg tggatggcac acccaaaca    540
actggcatcg agaacagtaa aacaccgcag aattctgcag attgtaccta caacctcagc   600
agcactctga cactgaccag cacacagtac aacagccaca aagagtacac ctgcaaggtg   660
acccagggca cgacctcagt cgtccagagc ttcaataggg gtgactgtta g            711
```

<210> SEQ ID NO 13
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Gln Glu Gln Leu Val Glu Ser Gly Gly Asp Leu Val Lys Pro Gly Ala
1               5                   10                  15
```

```
Ser Leu Thr Leu Thr Cys Thr Ala Ser Gly Phe Ser Phe Ser Ser Gly
            20                  25                  30

Tyr Tyr Met Cys Trp Val Arg Gln Ala Pro Gly Lys Gly Leu Glu Trp
        35                  40                  45

Ile Ala Cys Ile Tyr Gly Gly Ala Leu Thr Asn Thr Tyr Tyr Ala Thr
 50                  55                  60

Trp Ala Lys Gly Arg Phe Thr Ile Ser Lys Thr Ser Thr Thr Val
 65                  70                  75                  80

Thr Leu Gln Met Thr Ser Leu Thr Ala Ala Asp Thr Ala Thr Tyr Phe
                85                  90                  95

Cys Ala Arg Asp Leu Gly Ala Ala Gly Asp Ala Tyr Asn Leu Trp Gly
            100                 105                 110

Pro Gly Thr Leu Val Thr Val Ser Ser
            115                 120
```

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Gln Ser Leu Glu Glu Ser Gly Gly Asp Leu Val Lys Pro Gly Ala Ser
 1               5                  10                  15

Leu Thr Leu Thr Cys Lys Ala Ser Gly Phe Asp Phe Ser Ser Ser Tyr
            20                  25                  30

Tyr Met Cys Trp Val Arg Gln Ala Pro Gly Arg Leu Glu Trp Ile Ala
        35                  40                  45

Cys Ile Tyr Gly Gly Gly Leu Ser Asn Thr Tyr Tyr Ala Gly Trp Ala
 50                  55                  60

Lys Gly Arg Phe Thr Ile Ser Lys Thr Ser Ser Thr Thr Val Thr Leu
 65                  70                  75                  80

Gln Met Thr Ser Leu Thr Val Ala Asp Thr Ala Thr Tyr Phe Cys Ala
                85                  90                  95

Arg Asp Ala Gly Thr Ser Gly Asp Tyr Leu Asn Leu Trp Gly Pro Gly
            100                 105                 110

Thr Leu Val Thr Val Ser Ser
            115
```

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gln Gln Gln Leu Glu Glu Ser Gly Gly Gly Leu Val Gln Pro Glu Gly
 1               5                  10                  15

Ser Leu Thr Leu Thr Cys Ile Ala Ser Gly Phe Ser Phe Ser Ser Ser
            20                  25                  30

His Trp Ile Cys Trp Val Arg Gln Ala Pro Gly Lys Gly Leu Glu Trp
        35                  40                  45

Ile Ala Cys Met Ser Thr Ser Ser Gly Ser Thr Tyr Asp Ala Asn Trp
 50                  55                  60
```

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
            85                  90                  95

Ala Arg Asp Val Gly Gly Ser Thr Thr Tyr Phe Asp Leu Trp Gly Pro
            100                 105                 110

Gly Thr Leu Val Thr Val Ser Ser
        115                 120

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ala Pro Gly Lys Arg Leu Glu Trp Ile
            35                  40                  45

Ala Cys Ile Tyr Gly Gly Gly Leu Ser Asn Thr Tyr Tyr Ala Gly Trp
        50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
            85                  90                  95

Ala Arg Asp Ala Thr Ser Gly Asp Tyr Leu Asn Leu Trp Gly Pro Gly
            100                 105                 110

Thr Leu Val Thr Val Ser Ser
        115

<210> SEQ ID NO 17
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Gln Gln Leu Glu Glu Ser Gly Gly Gly Leu Val Lys Pro Gly Gly
1               5                   10                  15

Thr Leu Thr Leu Thr Cys Lys Ala Ser Gly Ile Asp Phe Ser Asn Tyr
            20                  25                  30

Tyr Tyr Met Cys Trp Val Arg Gln Ala Pro Gly Lys Gly Leu Glu Leu
            35                  40                  45

Ile Ala Cys Ile Tyr Thr Gly Ser Ser Gly Ser Thr Trp Tyr Ala Thr
        50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
            85                  90                  95

Cys Ala Arg Asp Arg Asp Val Gly Ser Leu Tyr Asp Ser Leu Asp Leu
            100                 105                 110

```
Trp Gly Gln Gly Thr Leu Val Thr Val Ser Pro
        115                 120

<210> SEQ ID NO 18
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Glu Gln Leu Val Glu Ser Gly Gly Leu Val Gln Pro Glu Gly
1               5                   10                  15

Ser Leu Thr Leu Thr Cys Thr Ala Ser Gly Phe Ser Phe Ser Asp Ser
            20                  25                  30

Tyr Tyr Met Cys Trp Val Arg Gln Ala Pro Gly Lys Gly Leu Glu Trp
        35                  40                  45

Ile Ala Cys Ile Tyr Gly Gly Thr Ile Thr Asn Thr Tyr Tyr Ala Ser
    50                  55                  60

Trp Ala Lys Gly Arg Phe Thr Ile Ser Lys Thr Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Asp Leu Gly Ala Ala Gly Asp Ala Tyr Asn Leu Trp Gly
            100                 105                 110

Pro Gly Thr Leu Val Thr Val Ser Ser
        115                 120

<210> SEQ ID NO 19
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Ser Asp Met Thr Gln Thr Pro Ala Ser Val Ser Ala Ala Val Gly
1               5                   10                  15

Gly Thr Val Thr Ile Lys Cys Gln Ala Ser Glu Ser Ile Tyr Ser Gly
            20                  25                  30

Leu Ala Trp Tyr Gln Gln Lys Pro Gly Gln Pro Pro Lys Leu Leu Ile
        35                  40                  45

Phe Asp Ala Ser Asp Leu Ala Ser Gly Val Pro Ser Arg Phe Lys Gly
    50                  55                  60

Ser Arg Ser Glu Thr Glu Tyr Thr Leu Thr Ile Ser Asp Leu Glu Cys
65                  70                  75                  80

Ala Asp Ala Ala Thr Tyr Tyr Cys Gln Cys Thr Asp Arg Asn Ser Ile
                85                  90                  95

Thr Ser Tyr Ala Phe Gly Gly Gly Thr Glu Val Val Val Lys
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 20

```
Ala Val Val Met Thr Gln Thr Ala Ser Pro Val Ser Gly Ala Val Gly
1               5                   10                  15

Gly Thr Val Thr Ile Asn Cys Gln Ala Ser Gln Ser Ile Ser Ser Ser
            20                  25                  30

Tyr Leu Ser Trp Tyr Gln Gln Lys Pro Gly Gln Pro Pro Lys Leu Leu
        35                  40                  45

Ile Tyr Gly Ala Ser Thr Leu Ala Ser Gly Val Pro Ser Arg Phe Lys
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Ala Tyr Asp Ala Tyr Arg Leu
                85                  90                  95

Ser Ser Pro Asp Asn Ile Phe Gly Gly Thr Glu Val Val Val Lys
                100                 105                 110
```

<210> SEQ ID NO 21
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Ala Tyr Asp Met Thr Gln Thr Pro Ala Ser Val Ser Glu Pro Val Gly
1               5                   10                  15

Gly Thr Val Thr Ile Lys Cys Gln Ala Ser Gln Ser Ile Ser Asn Glu
            20                  25                  30

Leu Ser Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Asn Gly Val Glu Cys
65                  70                  75                  80

Ala Asp Ala Ala Thr Tyr Tyr Cys Gln Gln Gly Tyr Ser Ile Ser Asn
                85                  90                  95

Val Asp Asn Thr Phe Gly Gly Gly Thr Glu Val Val Val Lys
                100                 105                 110
```

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Ala Val Val Met Thr Gln Thr Ala Ser Pro Val Ser Gly Ala Val Gly
1               5                   10                  15

Gly Thr Val Thr Ile Asn Cys Gln Ala Ser Gln Ser Ile Ser Ala Ser
            20                  25                  30

Ala Leu Ser Trp Tyr Gln Gln Lys Pro Gly Gln Pro Pro Lys Leu Leu
        35                  40                  45

Ile Tyr Ala Ala Ser Thr Leu Glu Ser Gly Val Pro Ser Arg Phe Lys
    50                  55                  60
```

```
Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Ala Tyr Asp Gly Tyr Arg Leu
                 85                  90                  95

Ser Ser Ala Asp Asn Ile Phe Gly Gly Gly Thr Glu Val Val Val Lys
            100                 105                 110
```

<210> SEQ ID NO 23
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Ala Tyr Asp Met Thr Gln Thr Pro Ala Ser Val Glu Ala Ala Val Gly
  1               5                  10                  15

Gly Thr Val Thr Ile Asn Cys Gln Ala Ser Gln Ser Ile Asn Asn Trp
                 20                  25                  30

Leu Ser Trp Tyr Gln Gln Lys Pro Gly Gln Arg Pro Lys Leu Leu Ile
             35                  40                  45

Tyr Gln Ala Ser Thr Leu Ala Ser Gly Val Ser Ser Arg Phe Lys Gly
 50                  55                  60

Ser Gly Ser Gly Thr His Phe Thr Leu Thr Ile Ser Asp Leu Glu Cys
 65                  70                  75                  80

Ala Asp Ala Ala Thr Tyr Tyr Cys Gln Gln Gly Trp Ser Ile Asp Asp
                 85                  90                  95

Ile Asp Asn Ala Phe Gly Gly Gly Thr Glu Val Val Val Lys
            100                 105                 110
```

<210> SEQ ID NO 24
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Ala Ser Asp Met Thr Gln Thr Pro Ala Ser Val Ser Glu Pro Val Gly
  1               5                  10                  15

Gly Thr Val Thr Ile Lys Cys Gln Ala Ser Glu Asn Ile Tyr Ser Ser
                 20                  25                  30

Leu Ala Trp Tyr Gln Gln Lys Pro Gly Gln Pro Pro Lys Leu Leu Ile
             35                  40                  45

Tyr Asp Ala Ser Asn Leu Ala Ser Gly Val Pro Ser Arg Phe Ser Gly
 50                  55                  60

Ser Gly Ser Gly Thr Glu Phe Thr Leu Thr Ile Ser Asp Leu Glu Cys
 65                  70                  75                  80

Ala Asp Ala Ala Thr Tyr Tyr Cys Gln Cys Thr Tyr Arg Ser Ser Ser
                 85                  90                  95

Ser Ser Tyr Ala Phe Gly Gly Gly Thr Glu Val Val Val Lys
            100                 105                 110
```

<210> SEQ ID NO 25
<211> LENGTH: 323
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 25

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
    50                  55                  60

Leu Ser Ser Val Val Ser Val Thr Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Met Cys Pro Pro Glu Leu Pro Gly
            100                 105                 110

Gly Pro Ser Val Phe Ile Phe Pro Pro Lys Pro Lys Asp Thr Leu Met
        115                 120                 125

Ile Ser Arg Thr Pro Glu Val Thr Cys Val Val Asp Val Ser Gln
130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
            180                 185                 190

Lys Glu Phe Lys Cys Lys Val His Asn Lys Ala Leu Pro Ala Pro Ile
        195                 200                 205

Glu Lys Thr Ile Ser Lys Ala Arg Gly Gln Pro Leu Glu Pro Lys Val
    210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Thr
            260                 265                 270

Val Leu Asp Ser Asp Gly Ser Tyr Phe Leu Tyr Ser Lys Leu Ser Val
        275                 280                 285

Pro Thr Ser Glu Trp Gln Arg Gly Asp Val Phe Thr Cys Ser Val Met
    290                 295                 300

His Glu Ala Leu His Asn His Tyr Thr Gln Lys Ser Ile Ser Arg Ser
305                 310                 315                 320

Pro Gly Lys

<210> SEQ ID NO 26
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
        35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Ser Phe Ser Ser Gly Tyr Tyr Met Cys
1               5                   10

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Ile Ala Cys Ile Tyr Gly Gly Ala Leu Thr Asn Thr Tyr Tyr Ala
1               5                   10                  15

Thr Trp Ala

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Arg Asp Leu Gly Ala Ala Gly Asp Ala Tyr Asn
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Ser Ile Tyr Ser Gly Leu Ala
1               5

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Leu Ile Phe Asp Ala Ser Asp Leu Ala Ser
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Cys Thr Asp Arg Asn Ser Ile Thr Ser Tyr Ala
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Asp Phe Ser Ser Ser Tyr Tyr Met Cys
1               5                   10

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp Ile Ala Cys Ile Tyr Gly Gly Gly Leu Ser Asn Thr Tyr Tyr Ala
1               5                   10                  15

Gly Trp Ala

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Arg Asp Ala Gly Thr Ser Gly Asp Tyr Leu Asn
1               5                   10

```
<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ser Ile Ser Ser Ser Tyr Leu Ser
1               5

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Leu Ile Tyr Gly Ala Ser Thr Leu Ala Ser
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Tyr Asp Ala Tyr Arg Leu Ser Ser Pro Asp Asn Ile
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Phe Ser Phe Ser Ser Ser His Trp Ile Cys
1               5                   10

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Trp Ile Ala Cys Met Ser Thr Ser Ser Gly Ser Thr Tyr Asp Ala Asn
1               5                   10                  15

Trp Ala

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 41

Ala Arg Asp Val Gly Gly Ser Thr Thr Tyr Phe Asp
1               5                   10

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Ser Ile Ser Asn Glu Leu Ser
1               5

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Leu Ile Tyr Arg Ala Ser Thr Leu Ala Ser
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gln Gly Tyr Ser Ile Ser Asn Val Asp Asn Thr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Phe Ser Phe Ser Ser Ser Tyr Tyr Met Cys
1               5                   10

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Ile Ala Cys Ile Tyr Gly Gly Gly Leu Ser Asn Thr Tyr Tyr Ala
1               5                   10                  15

Gly Trp Ala
```

```
<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Arg Asp Ala Gly Thr Ser Gly Asp Tyr Leu Asn
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ser Ile Ser Ala Ser Ala Leu Ser
1               5

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Leu Ile Tyr Ala Ala Ser Thr Leu Glu Ser
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Tyr Asp Gly Tyr Arg Leu Ser Ser Ala Asp Asn Ile
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Asp Phe Ser Asn Tyr Tyr Tyr Met Cys
1               5                   10

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 52

Leu Ile Ala Cys Ile Tyr Thr Gly Ser Ser Gly Ser Thr Trp Tyr Ala
1               5                   10                  15

Thr Trp Ala

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Arg Asp Arg Asp Val Gly Ser Leu Tyr Asp Ser Leu Asp
1               5                   10

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Ser Ile Asn Asn Trp Leu Ser
1               5

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Leu Ile Tyr Gln Ala Ser Thr Leu Ala Ser
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Gly Trp Ser Ile Asp Asp Ile Asp Asn Ala
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Ser Phe Ser Asp Ser Tyr Tyr Met Cys
1               5                   10
```

```
<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Ile Ala Cys Ile Tyr Gly Gly Thr Ile Thr Asn Thr Tyr Tyr Ala
1               5                   10                  15

Ser Trp Ala

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Arg Asp Leu Gly Ala Ala Gly Asp Ala Tyr Asn
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Asn Ile Tyr Ser Ser Leu Ala
1               5

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Leu Ile Tyr Asp Ala Ser Asn Leu Ala Ser
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Cys Thr Tyr Arg Ser Ser Ser Ser Ser Tyr Ala
1               5                   10

<210> SEQ ID NO 63
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 63

```
Met Glu Thr Gly Leu Arg Trp Leu Leu Leu Val Thr Val Leu Lys Gly
1               5                   10                  15

Val Gln Cys Gln Glu Gln Leu Val Glu Ser Gly Gly Asp Leu Val Lys
            20                  25                  30

Pro Gly Ala Ser Leu Thr Leu Thr Cys Thr Ala Ser Gly Phe Ser Phe
        35                  40                  45

Ser Ser Gly Tyr Tyr Met Cys Trp Val Arg Gln Ala Pro Gly Lys Gly
    50                  55                  60

Leu Glu Trp Ile Ala Cys Ile Tyr Gly Gly Ala Leu Thr Asn Thr Tyr
65                  70                  75                  80

Tyr Ala Thr Trp Ala Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Asp Leu Gly Ala Ala Gly Asp Ala Tyr Asn
        115                 120                 125

Leu Trp Gly Pro Gly Thr Leu Val Thr Val Ser Ser Gly Gln Pro Lys
130                 135                 140

Ala Pro Ser Val Phe Pro Leu Ala Pro Cys Cys Gly Asp Thr Pro Ser
145                 150                 155                 160

Ser Thr Val Thr Leu Gly Cys Leu Val Lys Gly Tyr Leu Pro Glu Pro
                165                 170                 175

Val Thr Val Thr Trp Asn Ser Gly Thr Leu Thr Asn Gly Val Arg Thr
            180                 185                 190

Phe Pro Ser Val Arg Gln Ser Ser Gly Leu Tyr Ser Leu Ser Ser Val
        195                 200                 205

Val Ser Val Thr Ser Ser Gln Pro Val Thr Cys Asn Val Ala His
    210                 215                 220

Pro Ala Thr Asn Thr Lys Val Asp Lys Thr Val Ala Pro Ser Thr Cys
225                 230                 235                 240

Ser Lys Pro Met Cys Pro Pro Glu Leu Pro Gly Gly Pro Ser Val
                245                 250                 255

Phe Ile Phe Pro Pro Lys Pro Lys Asp Thr Leu Met Ile Ser Arg Thr
            260                 265                 270

Pro Glu Val Thr Cys Val Val Asp Val Ser Gln Asp Asp Pro Glu
        275                 280                 285

Val Gln Phe Thr Trp Tyr Ile Asn Asn Glu Gln Val Arg Thr Ala Arg
    290                 295                 300

Pro Pro Leu Arg Glu Gln Gln Phe Asn Ser Thr Ile Arg Val Val Ser
305                 310                 315                 320

Thr Leu Pro Ile Ala His Gln Asp Trp Leu Arg Gly Lys Glu Phe Lys
                325                 330                 335

Cys Lys Val His Asn Lys Ala Leu Pro Ala Pro Ile Glu Lys Thr Ile
            340                 345                 350

Ser Lys Ala Arg Gly Gln Pro Leu Glu Pro Lys Val Tyr Thr Met Gly
        355                 360                 365

Pro Pro Arg Glu Glu Leu Ser Ser Arg Ser Val Ser Leu Thr Cys Met
370                 375                 380

Ile Asn Gly Phe Tyr Pro Ser Asp Ile Ser Val Glu Trp Glu Lys Asn
385                 390                 395                 400
```

Gly Lys Ala Glu Asp Asn Tyr Lys Thr Thr Pro Thr Val Leu Asp Ser
            405                 410                 415

Asp Gly Ser Tyr Phe Leu Tyr Ser Lys Leu Ser Val Pro Thr Ser Glu
            420                 425                 430

Trp Gln Arg Gly Asp Val Phe Thr Cys Ser Val Met His Glu Ala Leu
            435                 440                 445

His Asn His Tyr Thr Gln Lys Ser Ile Ser Arg Ser Pro Gly Lys
            450                 455                 460

<210> SEQ ID NO 64
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Lys Ala Ser Gly Phe Asp Phe Ser
        35                  40                  45

Ser Ser Tyr Tyr Met Cys Trp Val Arg Gln Ala Pro Gly Arg Leu Glu
    50                  55                  60

Trp Ile Ala Cys Ile Tyr Gly Gly Leu Ser Asn Thr Tyr Tyr Ala
65              70                  75                  80

Gly Trp Ala Lys Gly Arg Phe Thr Ile Ser Lys Thr Ser Ser Thr Thr
                85                  90                  95

Val Thr Leu Gln Met Thr Ser Leu Thr Val Ala Asp Thr Ala Thr Tyr
            100                 105                 110

Phe Cys Ala Arg Asp Ala Gly Thr Ser Gly Asp Tyr Leu Asn Leu Trp
        115                 120                 125

Gly Pro Gly Thr Leu Val Thr Val Ser Ser Gly Gln Pro Lys Ala Pro
    130                 135                 140

Ser Val Phe Pro Leu Ala Pro Cys Cys Gly Asp Thr Pro Ser Ser Thr
145                 150                 155                 160

Val Thr Leu Gly Cys Leu Val Lys Gly Tyr Leu Pro Glu Pro Val Thr
                165                 170                 175

Val Thr Trp Asn Ser Gly Thr Leu Thr Asn Gly Val Arg Thr Phe Pro
            180                 185                 190

Ser Val Arg Gln Ser Ser Gly Leu Tyr Ser Leu Ser Ser Val Val Ser
        195                 200                 205

Val Thr Ser Ser Ser Gln Pro Val Thr Cys Asn Val Ala His Pro Ala
    210                 215                 220

Thr Asn Thr Lys Val Asp Lys Thr Val Ala Pro Ser Thr Cys Ser Lys
225                 230                 235                 240

Pro Met Cys Pro Pro Pro Glu Leu Pro Gly Gly Pro Ser Val Phe Ile
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Asp Asp Pro Glu Val Gln
        275                 280                 285

```
Phe Thr Trp Tyr Ile Asn Asn Glu Gln Val Arg Thr Ala Arg Pro Pro
    290                 295                 300

Leu Arg Glu Gln Gln Phe Asn Ser Thr Ile Arg Val Val Ser Thr Leu
305                 310                 315                 320

Pro Ile Ala His Gln Asp Trp Leu Arg Gly Lys Glu Phe Lys Cys Lys
                325                 330                 335

Val His Asn Lys Ala Leu Pro Ala Pro Ile Glu Lys Thr Ile Ser Lys
            340                 345                 350

Ala Arg Gly Gln Pro Leu Glu Pro Lys Val Tyr Thr Met Gly Pro Pro
        355                 360                 365

Arg Glu Glu Leu Ser Ser Arg Ser Val Ser Leu Thr Cys Met Ile Asn
    370                 375                 380

Gly Phe Tyr Pro Ser Asp Ile Ser Val Glu Trp Glu Lys Asn Gly Lys
385                 390                 395                 400

Ala Glu Asp Asn Tyr Lys Thr Thr Pro Thr Val Leu Asp Ser Asp Gly
                405                 410                 415

Ser Tyr Phe Leu Tyr Ser Lys Leu Ser Val Pro Thr Ser Glu Trp Gln
            420                 425                 430

Arg Gly Asp Val Phe Thr Cys Ser Val Met His Glu Ala Leu His Asn
        435                 440                 445

His Tyr Thr Gln Lys Ser Ile Ser Arg Ser Pro Gly Lys
    450                 455                 460

<210> SEQ ID NO 65
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Glu Thr Gly Leu Arg Trp Leu Leu Leu Val Ala Val Leu Lys Gly
1               5                   10                  15

Val Gln Cys Gln Gln Gln Leu Glu Glu Ser Gly Gly Gly Leu Val Gln
            20                  25                  30

Pro Glu Gly Ser Leu Thr Leu Thr Cys Ile Ala Ser Gly Phe Ser Phe
        35                  40                  45

Ser Ser Ser His Trp Ile Cys Trp Val Arg Gln Ala Pro Gly Lys Gly
    50                  55                  60

Leu Glu Trp Ile Ala Cys Met Ser Thr Ser Ser Gly Ser Thr Tyr Asp
65                  70                  75                  80

Ala Asn Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Arg Asp Val Gly Gly Ser Thr Thr Tyr Phe Asp Leu
        115                 120                 125

Trp Gly Pro Gly Thr Leu Val Thr Val Ser Ser Gly Gln Pro Lys Ala
    130                 135                 140

Pro Ser Val Phe Pro Leu Ala Pro Cys Cys Gly Asp Thr Pro Ser Ser
145                 150                 155                 160

Thr Val Thr Leu Gly Cys Leu Val Lys Gly Tyr Leu Pro Glu Pro Val
                165                 170                 175
```

```
Thr Val Thr Trp Asn Ser Gly Thr Leu Thr Asn Gly Val Arg Thr Phe
            180                 185                 190

Pro Ser Val Arg Gln Ser Ser Gly Leu Tyr Ser Leu Ser Ser Val Val
        195                 200                 205

Ser Val Thr Ser Ser Ser Gln Pro Val Thr Cys Asn Val Ala His Pro
    210                 215                 220

Ala Thr Asn Thr Lys Val Asp Lys Thr Val Ala Pro Ser Thr Cys Ser
225                 230                 235                 240

Lys Pro Met Cys Pro Pro Glu Leu Pro Gly Gly Pro Ser Val Phe
            245                 250                 255

Ile Phe Pro Pro Lys Pro Lys Asp Thr Leu Met Ile Ser Arg Thr Pro
            260                 265                 270

Glu Val Thr Cys Val Val Val Asp Val Ser Gln Asp Asp Pro Glu Val
        275                 280                 285

Gln Phe Thr Trp Tyr Ile Asn Asn Glu Gln Val Arg Thr Ala Arg Pro
    290                 295                 300

Pro Leu Arg Glu Gln Gln Phe Asn Ser Thr Ile Arg Val Val Ser Thr
305                 310                 315                 320

Leu Pro Ile Ala His Gln Asp Trp Leu Arg Gly Lys Glu Phe Lys Cys
            325                 330                 335

Lys Val His Asn Lys Ala Leu Pro Ala Pro Ile Glu Lys Thr Ile Ser
            340                 345                 350

Lys Ala Arg Gly Gln Pro Leu Glu Pro Lys Val Tyr Thr Met Gly Pro
        355                 360                 365

Pro Arg Glu Glu Leu Ser Ser Arg Ser Val Ser Leu Thr Cys Met Ile
370                 375                 380

Asn Gly Phe Tyr Pro Ser Asp Ile Ser Val Glu Trp Glu Lys Asn Gly
385                 390                 395                 400

Lys Ala Glu Asp Asn Tyr Lys Thr Thr Pro Thr Val Leu Asp Ser Asp
            405                 410                 415

Gly Ser Tyr Phe Leu Tyr Ser Lys Leu Ser Val Pro Thr Ser Glu Trp
        420                 425                 430

Gln Arg Gly Asp Val Phe Thr Cys Ser Val Met His Glu Ala Leu His
    435                 440                 445

Asn His Tyr Thr Gln Lys Ser Ile Ser Arg Ser Pro Gly Lys
    450                 455                 460

<210> SEQ ID NO 66
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Phe Ser Phe Ser
        35                  40                  45

Ser Ser Tyr Tyr Met Cys Trp Val Arg Gln Ala Pro Gly Lys Arg Leu
    50                  55                  60
```

```
Glu Trp Ile Ala Cys Ile Tyr Gly Gly Gly Leu Ser Asn Thr Tyr Tyr
 65                  70                  75                  80

Ala Gly Trp Ala Lys Gly Arg Phe Thr Ile Ser Lys Thr Ser Ser Thr
                 85                  90                  95

Thr Val Thr Leu Gln Met Thr Ser Leu Thr Ala Ala Asp Thr Ala Thr
                100                 105                 110

Tyr Phe Cys Ala Arg Asp Ala Gly Thr Ser Gly Asp Tyr Leu Asn Leu
                115                 120                 125

Trp Gly Pro Gly Thr Leu Val Thr Val Ser Ser Gly Gln Pro Lys Ala
            130                 135                 140

Pro Ser Val Phe Pro Leu Ala Pro Cys Cys Gly Asp Thr Pro Ser Ser
145                 150                 155                 160

Thr Val Thr Leu Gly Cys Leu Val Lys Gly Tyr Leu Pro Glu Pro Val
                165                 170                 175

Thr Val Thr Trp Asn Ser Gly Thr Leu Thr Asn Gly Val Arg Thr Phe
                180                 185                 190

Pro Ser Val Arg Gln Ser Ser Gly Leu Tyr Ser Leu Ser Ser Val Val
            195                 200                 205

Ser Val Thr Ser Ser Gln Pro Val Thr Cys Asn Val Ala His Pro
210                 215                 220

Ala Thr Asn Thr Lys Val Asp Lys Thr Val Ala Pro Ser Thr Cys Ser
225                 230                 235                 240

Lys Pro Met Cys Pro Pro Pro Glu Leu Pro Gly Gly Pro Ser Val Phe
                245                 250                 255

Ile Phe Pro Pro Lys Pro Lys Asp Thr Leu Met Ile Ser Arg Thr Pro
                260                 265                 270

Glu Val Thr Cys Val Val Val Asp Val Ser Gln Asp Asp Pro Glu Val
                275                 280                 285

Gln Phe Thr Trp Tyr Ile Asn Asn Glu Gln Val Arg Thr Ala Arg Pro
            290                 295                 300

Pro Leu Arg Glu Gln Gln Phe Asn Ser Thr Ile Arg Val Val Ser Thr
305                 310                 315                 320

Leu Pro Ile Ala His Gln Asp Trp Leu Arg Gly Lys Glu Phe Lys Cys
                325                 330                 335

Lys Val His Asn Lys Ala Leu Pro Ala Pro Ile Glu Lys Thr Ile Ser
                340                 345                 350

Lys Ala Arg Gly Gln Pro Leu Glu Pro Lys Val Tyr Thr Met Gly Pro
                355                 360                 365

Pro Arg Glu Glu Leu Ser Ser Arg Ser Val Ser Leu Thr Cys Met Ile
        370                 375                 380

Asn Gly Phe Tyr Pro Ser Asp Ile Ser Val Glu Trp Glu Lys Asn Gly
385                 390                 395                 400

Lys Ala Glu Asp Asn Tyr Lys Thr Thr Pro Thr Val Leu Asp Ser Asp
                405                 410                 415

Gly Ser Tyr Phe Leu Tyr Ser Lys Leu Ser Val Pro Thr Ser Glu Trp
                420                 425                 430

Gln Arg Gly Asp Val Phe Thr Cys Ser Val Met His Glu Ala Leu His
            435                 440                 445

Asn His Tyr Thr Gln Lys Ser Ile Ser Arg Ser Pro Gly Lys
450                 455                 460
```

<210> SEQ ID NO 67
<211> LENGTH: 465

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67
```

Met Glu Thr Gly Leu Arg Trp Leu Leu Leu Val Ala Val Leu Lys Gly
1               5                   10                  15

Val Gln Cys Gln Gln Leu Glu Glu Ser Gly Gly Gly Leu Val Lys
            20                  25                  30

Pro Gly Gly Thr Leu Thr Leu Thr Cys Lys Ala Ser Gly Ile Asp Phe
                35                  40                  45

Ser Asn Tyr Tyr Tyr Met Cys Trp Val Arg Gln Ala Pro Gly Lys Gly
    50                  55                  60

Leu Glu Leu Ile Ala Cys Ile Tyr Thr Gly Ser Ser Gly Ser Thr Trp
65                  70                  75                  80

Tyr Ala Thr Trp Ala Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
                100                 105                 110

Thr Tyr Phe Cys Ala Arg Asp Arg Asp Val Gly Ser Leu Tyr Asp Ser
                115                 120                 125

Leu Asp Leu Trp Gly Gln Gly Thr Leu Val Thr Val Ser Pro Gly Gln
            130                 135                 140

Pro Lys Ala Pro Ser Val Phe Pro Leu Ala Pro Cys Cys Gly Asp Thr
145                 150                 155                 160

Pro Ser Ser Thr Val Thr Leu Gly Cys Leu Val Lys Gly Tyr Leu Pro
                165                 170                 175

Glu Pro Val Thr Val Thr Trp Asn Ser Gly Thr Leu Thr Asn Gly Val
                180                 185                 190

Arg Thr Phe Pro Ser Val Arg Gln Ser Ser Gly Leu Tyr Ser Leu Ser
            195                 200                 205

Ser Val Val Ser Val Thr Ser Ser Ser Gln Pro Val Thr Cys Asn Val
210                 215                 220

Ala His Pro Ala Thr Asn Thr Lys Val Asp Lys Thr Val Ala Pro Ser
225                 230                 235                 240

Thr Cys Ser Lys Pro Met Cys Pro Pro Glu Leu Pro Gly Gly Pro
                245                 250                 255

Ser Val Phe Ile Phe Pro Pro Lys Pro Lys Asp Thr Leu Met Ile Ser
                260                 265                 270

Arg Thr Pro Glu Val Thr Cys Val Val Val Asp Val Ser Gln Asp Asp
            275                 280                 285

Pro Glu Val Gln Phe Thr Trp Tyr Ile Asn Asn Glu Gln Val Arg Thr
            290                 295                 300

Ala Arg Pro Pro Leu Arg Glu Gln Gln Phe Asn Ser Thr Ile Arg Val
305                 310                 315                 320

Val Ser Thr Leu Pro Ile Ala His Gln Asp Trp Leu Arg Gly Lys Glu
                325                 330                 335

Phe Lys Cys Lys Val His Asn Lys Ala Leu Pro Ala Pro Ile Glu Lys
            340                 345                 350

Thr Ile Ser Lys Ala Arg Gly Gln Pro Leu Glu Pro Lys Val Tyr Thr
            355                 360                 365

Met Gly Pro Pro Arg Glu Glu Leu Ser Ser Arg Ser Val Ser Leu Thr
    370                 375                 380

```
Cys Met Ile Asn Gly Phe Tyr Pro Ser Asp Ile Ser Val Glu Trp Glu
385                 390                 395                 400

Lys Asn Gly Lys Ala Glu Asp Asn Tyr Lys Thr Thr Pro Thr Val Leu
            405                 410                 415

Asp Ser Asp Gly Ser Tyr Phe Leu Tyr Ser Lys Leu Ser Val Pro Thr
            420                 425                 430

Ser Glu Trp Gln Arg Gly Asp Val Phe Thr Cys Ser Val Met His Glu
            435                 440                 445

Ala Leu His Asn His Tyr Thr Gln Lys Ser Ile Ser Arg Ser Pro Gly
            450                 455                 460

Lys
465

<210> SEQ ID NO 68
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Thr Ala Ser Gly Phe Ser Phe
        35                  40                  45

Ser Asp Ser Tyr Tyr Met Cys Trp Val Arg Gln Ala Pro Gly Lys Gly
    50                  55                  60

Leu Glu Trp Ile Ala Cys Ile Tyr Gly Gly Thr Ile Thr Asn Thr Tyr
65                  70                  75                  80

Tyr Ala Ser Trp Ala Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Asp Leu Gly Ala Ala Gly Asp Ala Tyr Asn
        115                 120                 125

Leu Trp Gly Pro Gly Thr Leu Val Thr Val Ser Ser Gly Gln Pro Lys
    130                 135                 140

Ala Pro Ser Val Phe Pro Leu Ala Pro Cys Cys Gly Asp Thr Pro Ser
145                 150                 155                 160

Ser Thr Val Thr Leu Gly Cys Leu Val Lys Gly Tyr Leu Pro Glu Pro
                165                 170                 175

Val Thr Val Thr Trp Asn Ser Gly Thr Leu Thr Asn Gly Val Arg Thr
            180                 185                 190

Phe Pro Ser Val Arg Gln Ser Ser Gly Leu Tyr Ser Leu Ser Ser Val
        195                 200                 205

Val Ser Val Thr Ser Ser Gln Pro Val Thr Cys Asn Val Ala His
    210                 215                 220

Pro Ala Thr Asn Thr Lys Val Asp Lys Thr Val Ala Pro Ser Thr Cys
225                 230                 235                 240

Ser Lys Pro Met Cys Pro Pro Pro Glu Leu Pro Gly Gly Pro Ser Val
                245                 250                 255
```

```
Phe Ile Phe Pro Pro Lys Pro Lys Asp Thr Leu Met Ile Ser Arg Thr
            260                 265                 270

Pro Glu Val Thr Cys Val Val Asp Val Ser Gln Asp Asp Pro Glu
    275                 280                 285

Val Gln Phe Thr Trp Tyr Ile Asn Asn Glu Gln Val Arg Thr Ala Arg
290                 295                 300

Pro Pro Leu Arg Glu Gln Gln Phe Asn Ser Thr Ile Arg Val Val Ser
305                 310                 315                 320

Thr Leu Pro Ile Ala His Gln Asp Trp Leu Arg Gly Lys Glu Phe Lys
                325                 330                 335

Cys Lys Val His Asn Lys Ala Leu Pro Ala Pro Ile Glu Lys Thr Ile
                340                 345                 350

Ser Lys Ala Arg Gly Gln Pro Leu Glu Pro Lys Val Tyr Thr Met Gly
                355                 360                 365

Pro Pro Arg Glu Glu Leu Ser Ser Arg Ser Val Ser Leu Thr Cys Met
370                 375                 380

Ile Asn Gly Phe Tyr Pro Ser Asp Ile Ser Val Glu Trp Glu Lys Asn
385                 390                 395                 400

Gly Lys Ala Glu Asp Asn Tyr Lys Thr Thr Pro Thr Val Leu Asp Ser
                405                 410                 415

Asp Gly Ser Tyr Phe Leu Tyr Ser Lys Leu Ser Val Pro Thr Ser Glu
                420                 425                 430

Trp Gln Arg Gly Asp Val Phe Thr Cys Ser Val Met His Glu Ala Leu
                435                 440                 445

His Asn His Tyr Thr Gln Lys Ser Ile Ser Arg Ser Pro Gly Lys
    450                 455                 460

<210> SEQ ID NO 69
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Asp Thr Arg Ala Pro Thr Gln Leu Leu Gly Leu Leu Leu Leu Trp
1               5                   10                  15

Leu Pro Gly Ala Arg Cys Ala Ser Asp Met Thr Gln Thr Pro Ala Ser
                20                  25                  30

Val Ser Ala Ala Val Gly Gly Thr Val Thr Ile Lys Cys Gln Ala Ser
            35                  40                  45

Glu Ser Ile Tyr Ser Gly Leu Ala Trp Tyr Gln Gln Lys Pro Gly Gln
    50                  55                  60

Pro Pro Lys Leu Leu Ile Phe Asp Ala Ser Asp Leu Ala Ser Gly Val
65                  70                  75                  80

Pro Ser Arg Phe Lys Gly Ser Arg Ser Glu Thr Glu Tyr Thr Leu Thr
                85                  90                  95

Ile Ser Asp Leu Glu Cys Ala Asp Ala Ala Thr Tyr Tyr Cys Gln Cys
                100                 105                 110

Thr Asp Arg Asn Ser Ile Thr Ser Tyr Ala Phe Gly Gly Gly Thr Glu
            115                 120                 125

Val Val Val Lys Gly Asp Pro Val Ala Pro Thr Val Leu Ile Phe Pro
130                 135                 140
```

```
Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
            195                 200                 205

Gln Tyr Asn Ser His Lys Glu Tyr Thr Cys Lys Val Thr Gln Gly Thr
        210                 215                 220

Thr Ser Val Val Gln Ser Phe Asn Arg Gly Asp Cys
225                 230                 235

<210> SEQ ID NO 70
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Asp Thr Arg Ala Pro Thr Gln Leu Leu Gly Leu Leu Leu Leu Trp
1               5                   10                  15

Leu Pro Gly Ala Arg Cys Ala Val Val Met Thr Gln Thr Ala Ser Pro
                20                  25                  30

Val Ser Gly Ala Val Gly Gly Thr Val Thr Ile Asn Cys Gln Ala Ser
            35                  40                  45

Gln Ser Ile Ser Ser Ser Tyr Leu Ser Trp Tyr Gln Gln Lys Pro Gly
        50                  55                  60

Gln Pro Pro Lys Leu Leu Ile Tyr Gly Ala Ser Thr Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Gly Val Gln Cys Asp Asp Ala Ala Thr Tyr Tyr Cys Ala
            100                 105                 110

Tyr Asp Ala Tyr Arg Leu Ser Ser Pro Asp Asn Ile Phe Gly Gly Gly
        115                 120                 125

Thr Glu Val Val Val Lys Gly Asp Pro Val Ala Pro Thr Val Leu Ile
130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
210                 215                 220

Gly Thr Thr Ser Val Val Gln Ser Phe Asn Arg Gly Asp Cys
225                 230                 235

<210> SEQ ID NO 71
<211> LENGTH: 236
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 71

```
Met Asp Thr Arg Ala Pro Thr Gln Leu Leu Gly Leu Leu Leu Trp
1               5                   10                  15

Leu Pro Gly Ala Arg Cys Ala Tyr Asp Met Thr Gln Thr Pro Ala Ser
                20                  25                  30

Val Ser Glu Pro Val Gly Gly Thr Val Thr Ile Lys Cys Gln Ala Ser
            35                  40                  45

Gln Ser Ile Ser Asn Glu Leu Ser Trp Tyr Gln Lys Pro Gly Gln
50                  55                  60

Pro Pro Lys Leu Leu Ile Tyr Arg Ala Ser Thr Leu Ala Ser Gly Val
65                  70                  75                  80

Pro Ser Arg Phe Lys Gly Ser Gly Ser Gly Thr Gln Phe Thr Leu Thr
                85                  90                  95

Ile Asn Gly Val Glu Cys Ala Asp Ala Ala Thr Tyr Tyr Cys Gln Gln
            100                 105                 110

Gly Tyr Ser Ile Ser Asn Val Asp Asn Thr Phe Gly Gly Gly Thr Glu
            115                 120                 125

Val Val Val Lys Gly Asp Pro Val Ala Pro Thr Val Leu Ile Phe Pro
        130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
            195                 200                 205

Gln Tyr Asn Ser His Lys Glu Tyr Thr Cys Lys Val Thr Gln Gly Thr
        210                 215                 220

Thr Ser Val Val Gln Ser Phe Asn Arg Gly Asp Cys
225                 230                 235
```

<210> SEQ ID NO 72
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Met Asp Thr Arg Ala Pro Thr Gln Leu Leu Gly Leu Leu Leu Trp
1               5                   10                  15

Leu Pro Gly Ala Arg Cys Ala Val Val Met Thr Gln Thr Ala Ser Pro
                20                  25                  30

Val Ser Gly Ala Val Gly Gly Thr Val Thr Ile Asn Cys Gln Ala Ser
            35                  40                  45

Gln Ser Ile Ser Ala Ser Ala Leu Ser Trp Tyr Gln Gln Lys Pro Gly
50                  55                  60

Gln Pro Pro Lys Leu Leu Ile Tyr Ala Ala Ser Thr Leu Glu Ser Gly
65                  70                  75                  80
```

```
Val Pro Ser Arg Phe Lys Gly Ser Gly Ser Gly Thr Gln Phe Thr Leu
                85                  90                  95

Thr Ile Ser Gly Val Gln Cys Asp Ala Ala Thr Tyr Tyr Cys Ala
            100                 105                 110

Tyr Asp Gly Tyr Arg Leu Ser Ser Ala Asp Asn Ile Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235

<210> SEQ ID NO 73
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Ala Ala Val Gly Gly Thr Val Thr Ile Asn Cys Gln Ala Ser
        35                  40                  45

Gln Ser Ile Asn Asn Trp Leu Ser Trp Tyr Gln Gln Lys Pro Gly Gln
    50                  55                  60

Arg Pro Lys Leu Leu Ile Tyr Gln Ala Ser Thr Leu Ala Ser Gly Val
65                  70                  75                  80

Ser Ser Arg Phe Lys Gly Ser Gly Ser Gly Thr His Phe Thr Leu Thr
                85                  90                  95

Ile Ser Asp Leu Glu Cys Ala Asp Ala Ala Thr Tyr Tyr Cys Gln Gln
            100                 105                 110

Gly Trp Ser Ile Asp Asp Ile Asp Asn Ala Phe Gly Gly Gly Thr Glu
        115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190
```

```
Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
        210                 215                 220

Thr Ser Val Val Gln Ser Phe Asn Arg Gly Asp Cys
225                 230                 235

<210> SEQ ID NO 74
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Asp Thr Arg Ala Pro Thr Gln Leu Leu Gly Leu Leu Leu Leu Trp
1               5                   10                  15

Leu Pro Gly Ala Arg Cys Ala Ser Asp Met Thr Gln Thr Pro Ala Ser
                20                  25                  30

Val Ser Glu Pro Val Gly Gly Thr Val Thr Ile Lys Cys Gln Ala Ser
            35                  40                  45

Glu Asn Ile Tyr Ser Ser Leu Ala Trp Tyr Gln Gln Lys Pro Gly Gln
    50                  55                  60

Pro Pro Lys Leu Leu Ile Tyr Asp Ala Ser Asn Leu Ala Ser Gly Val
65                  70                  75                  80

Pro Ser Arg Phe Ser Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Cys
            100                 105                 110

Thr Tyr Arg Ser Ser Ser Ser Tyr Ala Phe Gly Gly Gly Thr Glu
        115                 120                 125

Val Val Val Lys Gly Asp Pro Val Ala Pro Thr Val Leu Ile Phe Pro
        130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
        210                 215                 220

Thr Ser Val Val Gln Ser Phe Asn Arg Gly Asp Cys
225                 230                 235
```

RABBIT ANTIBODIES TO HUMAN IMMUNOGLOBULINS G

CROSS-REFERENCE TO RELATED APPLICATION

This application claims priority from U.S. Patent Application No. 63/033,073, filed Jun. 1, 2020, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 26, 2021, is named 022548_US063_SL.txt and is 83,191 bytes in size.

BACKGROUND OF THE INVENTION

Therapeutic monoclonal antibodies (mAbs) have become one of the fastest growing classes of drugs in recent years and are approved for the treatment of a wide range of indications, from cancer to autoimmune diseases. Preclinical pharmacokinetic characterization of these therapeutic monoclonal antibodies often has to be performed in non-human primates in order to prove efficacy and safety before the initiation of clinical studies. The cynomolgus monkey is a preferred non-human primate for such preclinical studies because it often provides a sufficient level of cross-reactivity with the target of the therapeutic antibody (Iwasaki et al., *Drug Metab Pharmacokinet.* (2019) 34: 55-63). However, the immunoglobulins of the cynomolgus monkey also show a high sequence homology with the immunoglobulins of humans. The lack of high-quality reagent antibodies that can distinguish a human therapeutic molecule from cynomolgus monkey immunoglobulin in the serum constitutes a significant challenge for the bioanalytical measurement of human therapeutic antibodies in non-human primate serum samples because of the high level of protein sequence homology for IgG (Stubenrauch et al., *J Pharm Biomed Anal.* (2009) 49:1003-8).

Currently, evaluation of therapeutic antibody pharmacokinetics (PK) and pharmacodynamics (PD) in preclinical studies relies on drug specific anti-idiotype antibodies, which are laborious and time-consuming to develop. Each drug candidate would require its own anti-idiotype antibody. There are few options for a universal reagent that can detect all human IgG-based therapeutic antibodies in preclinical studies. There is therefore a need to develop monoclonal antibodies that are universally specific for human IgG but do not bind monkey IgG, in order to accurately measure the levels of therapeutic human IgG-derived mAbs in non-human primates during preclinical studies.

SUMMARY OF THE INVENTION

The present disclosure provides isolated monoclonal antibodies or antigen-binding portions thereof that bind specifically to human IgG, wherein the antibodies or portions comprise heavy chain complementarity-determining region (CDR) 1-3 and light chain CDR1-3 respectively comprising SEQ ID NOs: 27-32, SEQ ID NOs: 33-38, SEQ ID NOs: 39-44, SEQ ID NOs: 45-50, SEQ ID NOs: 51-56, or SEQ ID NOs: 57-62. The antibodies may be rabbit antibodies or modified from such molecules (including, for example, chimeric antibodies with Fc domains from a non-rabbit species such as mouse, rat, or human).

In some embodiments, the present antibody or portion comprises heavy chain variable domain (VH) and light chain variable domain (VL) respectively comprising SEQ ID NOs: 13 and 19, SEQ ID NOs: 14 and 20, SEQ ID NOs: 15 and 21, SEQ ID NOs: 16 and 22, SEQ ID NOs: 17 and 23, or SEQ ID NOs: 18 and 24. The antibodies may be rabbit antibodies or modified from such molecules.

In some embodiments, the present antibody comprises a heavy chain constant region amino acid sequence of SEQ ID NO: 25, and/or a light chain constant region amino acid sequence of SEQ ID NO: 26. In further embodiments, the antibody comprises a heavy chain and a light chain having the amino acid sequences of SEQ ID NOs: 63 and 69, SEQ ID NOs: 64 and 70, SEQ ID NOs: 65 and 71, SEQ ID NOs: 66 and 72, SEQ ID NOs: 67 and 73, or SEQ ID NOs: 68 and 74, respectively, with or without the leader sequences.

In certain embodiments, the present antibody or antigen-binding portion comprises a detectable label.

The present disclosure also provides a composition or a kit comprising the present monoclonal antibody or antigen-binding portion in an aqueous buffered solution.

In other aspects, the present disclosure provides an isolated nucleic acid molecule encoding the heavy chain, the light chain, or both, of the present monoclonal antibody or antigen-binding portion. In some embodiments, the nucleic acid molecule comprises SEQ ID NOs: 1, 2, 3, 4, 5, 6, 7, 8, 9, 10, 11, and/or 12. In further embodiments, the nucleic acid molecule comprises SEQ ID NOs: 1 and 7, SEQ ID NOs: 2 and 8, SEQ ID NOs: 3 and 9, SEQ ID NOs: 4 and 10, SEQ ID NOs: 5 and 11, or SEQ ID NOs: 6 and 12. Also provided herein is an expression construct comprising the nucleic acid molecule, and a host cell (e.g., a mammalian cell) comprising nucleotide sequences encoding the heavy chain and the light chain of the present monoclonal antibody or antigen-binding portion. The present disclosure also provides a method of producing an antibody or an antigen-binding portion thereof, comprising culturing the host cell under conditions that allow expression of the heavy chain and light chain of the antibody or portion, and isolating the antibody or portion from the cultured cell or the supernatant of the cell culture.

In another aspect, the present disclosure provides a method of detecting human IgG or a fragment thereof in a sample, comprising contacting the sample with one or more monoclonal antibodies or antigen-binding portions described herein. The sample (e.g., a tissue sample such as a blood, serum, or plasma sample, or a biopsy sample) may be obtained from, for example, an animal that has been administered with an antibody comprising a human IgG constant region (e.g., human IgG1, IgG2, IgG3, or IgG4 constant region) or a fragment thereof (e.g., a Fab or F(ab')2 fragment). The animal may be, for example, a non-human primate such as cynomolgus monkey or rhesus monkey.

Other features, objectives, and advantages of the invention are apparent in the detailed description that follows. It should be understood, however, that the detailed description, while indicating embodiments and aspects of the invention, is given by way of illustration only, not limitation. Various changes and modifications within the scope of the invention will become apparent to those skilled in the art from the detailed description.

BRIEF DESCRIPTION OF THE DRAWINGS

FIG. 2A and FIG. 2B show the alignments of the heavy (FIG. 2A) and light (FIG. 2B) chain amino acid sequences, respectively, of the six rabbit recombinant antibody clones using Clustal Omega and the Kabat numbering system. CDRs (see also Zhang and Ho, MABS (2017) 9(3):419-29) are underlined and in in boldface. The leader sequences, the start of the variable domains, and the start of the constant regions are marked as shown.

FIG. 2C shows the phylogenetic trees of the VH and VL sequences of the six rabbit antibody clones.

FIGS. 4A-4C show a Gyrolab™ immunoassay using clone 16F5 as the capture reagent, and an overlay graph of hIgG4 in the assay matrixes containing 0%, 4%, 10% and 25% cynomolgus monkey serum (FIG. 4A); a standard curve graph of hIgG4 in the assay matrix containing 4% cynomolgus monkey serum (FIG. 4B); and quality controls in the same assay matrix containing 4% cynomolgus monkey serum (FIG. 4C). Clone 16F5 was biotinylated and used as the capture reagent. The human IgG4 antibody (hIgG4) served as the assay standard was diluted 1 to 4 at the range of 1200-0.30 ng/ml. Alexa Fluor647-conjugated Goat antihuman IgG was used for detection.

FIGS. 5A and 5B show a comparison of different clones used as capture reagents for detection of hIgG4 and hFab. FIG. 5A shows a standard curve of all six rabbit anti-hIgG mAb clones, plus Gyrolab™ and MCA5748G capture agents, for the detection of hIgG4. FIG. 5B shows the same set of capture reagents used for the detection of hIgG Fab. Note that the hFab cannot be detected by the Gyrolab™ capture agent or by the MCA5748G capture agent.

DETAILED DESCRIPTION OF THE INVENTION

Figure 1:
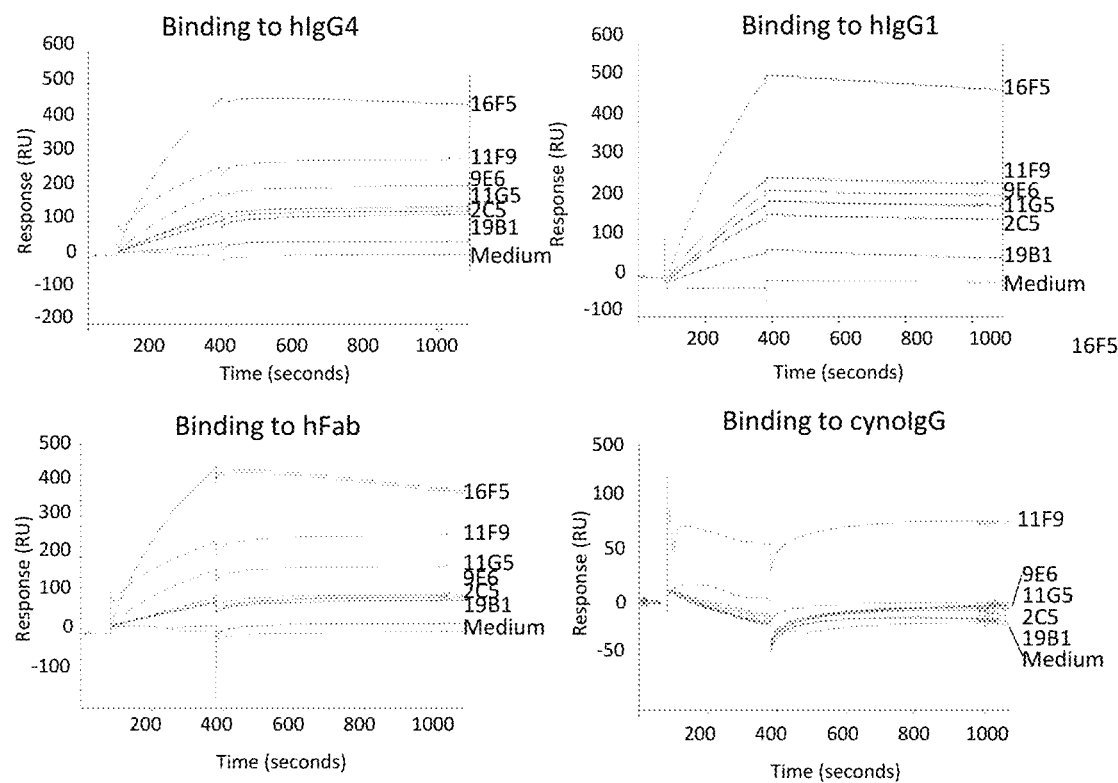
FIG. 1 is a panel of Biacore sensorgram graphs showing the binding of six rabbit recombinant antibody clones to whole human IgG1 (hIgG1), whole human IgG4 (hIgG4), human Fab (hFab), and cynomolgus monkey IgG (cynoIgG).

The present disclosure provides rabbit monoclonal antibodies that bind to human immunoglobulins G and Fab fragments thereof with high affinity and yet do not bind at a detectable level to IgG of non-human primates such as monkey (e.g., cynomolgus monkey or rhesus monkey). These rabbit antibodies are particular useful as reagents for detecting human IgG or fragments thereof in preclinical pharmacology studies of therapeutic human IgG-based antibodies in cynomolgus monkey or another non-human primate. For example, these rabbit antibodies can be used to study therapeutic antibodies that are fully human IgG antibodies, humanized IgG antibodies, chimeric antibodies having human IgG constant regions, and Fab fragments thereof. The present rabbit antibodies also can be used in preclinical immunohistochemistry studies and in manufacturing process development for human IgG-based therapeutic antibodies (e.g., whole antibodies including mono-specific, bi-specific, and tri-specific antibodies, as well as Fab fragments thereof).

The present rabbit monoclonal antibodies bind to three distinct epitopes on human IgG, which epitopes are further distinct from that bound by the commercially available mouse anti-hIgG antibody MCA5748G. Rabbit monoclonal antibodies offer several advantages over traditional mouse monoclonal antibodies. These advantages include higher binding affinity and specificity and more diverse epitope recognition. The rabbit's immune system is evolutionarily distinct from that of a rodent and it uses different mechanisms to generate, diversify, and optimize the affinity of the antibodies it produces. Additionally, the rabbit's immune system can recognize smaller-sized epitopes that are not immunogenic in mice, while maintaining the ability to produce strong immune responses. Therefore, the rabbit antibodies described herein are advantageous over mouse antibodies.

Rabbit Anti-hIgG Antibodies

The present disclosure provides antibodies that bind specifically (i.e., with high affinity) to human IgGs and antigen-binding portions thereof (e.g., Fab and F(ab')2). These antibodies do not bind at a detectable level to immunoglobulins (such as IgGs) from other species commonly used in preclinical studies (e.g., such as mice, rats, rabbits, non-human primates, or dogs).

As used herein, the term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind to an antigen when the binding affinity is high, i.e., with a $K_D$ of ≤100 nM (e.g., ≤10 nM or ≤1 nM). A $K_D$ binding affinity constant can be measured, e.g., by surface plasmon resonance (Biacore®), for example using the Biacore® T200 from Biacore. The binding affinity of a particular antibody-antigen interaction can also be shown by a standard concentration-response curve, for example using a Gyrolab™ xPlore from Gyros Protein Technologies. In some embodiments, the present antibodies bind to human IgG and Fab fragments derived therefrom with a $K_D$ no greater than 2 nM while showing no detectable binding to cynomolgus monkey IgG in a Biacore assay.

The antibodies exemplified herein bind to three distinct epitopes on hIgG and Fab fragments thereof. As used herein, the term "epitope" refers to a portion (determinant) of an antigen that specifically binds to an antibody or a related molecule such as a bi-specific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest (e.g., IgG or Fab) or a relevant portion thereof, then screening for binding to the epitope.

One can determine whether an antibody binds to the same epitope or competes for binding with an anti-hIgG antibody of the present disclosure by using methods known in the art, including, without limitation, competition assays, epitope binning, and alanine scanning. In some embodiments, one allows the anti-hIgG antibody of the present disclosure to bind to hIgG under saturating conditions, and then measures the ability of the test antibody to bind to hIgG. If the test antibody is able to bind to hIgG at the same time as the reference anti-IgG antibody, then the test antibody binds to a different epitope than the reference anti-IgG antibody. However, if the test antibody is not able to bind to hIgG at the same time, then the test antibody binds to the same epitope, an overlapping epitope, or an epitope that is in close proximity to the epitope bound by the anti-IgG antibody of the present disclosure. This experiment can be performed using, e.g., ELISA, RIA, BIACORE™, SPR, Bio-Layer Interferometry or flow cytometry. To test whether an anti-hIgG antibody cross-competes with another anti-IgG antibody, one may use the competition method described above in two directions, i.e., determining if the known antibody blocks the test antibody and vice versa. The competition experiments may be performed, e.g., using a Biacore® T200 instrument.

Antigen-binding portions of the anti-hIgG antibodies disclosed herein may be used in lieu of full antibodies. The term "antigen-binding portion" refers to one or more portions or fragments of an antibody that retain the ability to specifically bind to an antigen (e.g., human IgG, or a fragment thereof). Examples of antigen-binding portions are, without limitation, (i) a Fab fragment: a monovalent fragment consisting of the VL, VH, CL and CH1 domains; (ii) a F(ab')2 fragment: a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody; (v) a dAb fragment, which consists of a VH domain; and (vi) an isolated complementarity determining region (CDR) capable of specifically binding to an antigen. Furthermore, although the two domains of the Fv fragment, VL and VH, are encoded by separate genes, they can be joined, using recombinant methods, by a synthetic linker that enables them to be made as a single protein chain in which the VL and VH domains pair to form monovalent molecules (known as single chain Fv (scFv)). Other forms of single chain antibodies, such as diabodies, are also encompassed. Diabodies are bivalent, bi-specific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites. Antibody portions, such as Fab and F(ab')2 fragments, can be prepared from whole antibodies using conventional techniques, such as papain or pepsin digestion of whole antibodies, or recombinant DNA techniques.

The present antibodies bind to one, more, or all of human IgG subtypes hIgG1, hIgG2, hIgG3, and hIgG4. In certain embodiments, it binds all of said subtypes. It is understood that the antibodies described herein may also bind to humanized and/or chimeric antibodies comprising sequences from human IgG.

In some embodiments, the present disclosure provides an anti-hIgG monoclonal antibody or an antigen-binding portion thereof whose heavy chain CDR1-3 and light chain CDR1-3 comprise SEQ ID NOs:27-32, 33-38, 39-44, 45-50, 51-56, or 57-62, respectively. The framework of this antibody may be derived from an antibody from a rabbit or another species (e.g., mouse, human, or rat).

In some embodiments, the present disclosure provides an anti-hIgG monoclonal antibody or an antigen-binding portion thereof whose heavy chain variable domain (VH) and light chain variable domain (VL) comprise SEQ ID NOs:13 and 19, 14 and 20, 15 and 21, 16 and 22, 17 and 23, or 18 and 24, respectively. The constant region of this antibody may be derived from an antibody from rabbit or another species (e.g., mouse, human, or rat).

In some embodiments, the present disclosure provides an anti-hIgG monoclonal antibody comprising:
  a) a heavy chain (HC) comprising the amino acid sequences of SEQ ID NOs: 13 and 25 and a light chain (LC) comprising the amino acid sequences of SEQ ID NOs: 19 and 26;
  b) an HC comprising the amino acid sequences of SEQ ID NOs: 14 and 25 and an LC comprising the amino acid sequences of SEQ ID NOs: 20 and 26;
  c) an HC comprising the amino acid sequences of SEQ ID NOs: 15 and 25 and an LC comprising the amino acid sequences of SEQ ID NOs: 21 and 26;
  d) an HC comprising the amino acid sequences of SEQ ID NOs: 16 and 25 and an LC comprising the amino acid sequences of SEQ ID NOs: 22 and 26;
  e) an HC comprising the amino acid sequences of SEQ ID NOs: 17 and 25 and an LC comprising the amino acid sequences of SEQ ID NOs: 23 and 26; or
  f) an HC comprising the amino acid sequences of SEQ ID NOs: 18 and 25 and an LC comprising the amino acid sequences of SEQ ID NOs: 24 and 26.

In some embodiments, the anti-hIgG antibody or antigen-binding portion has a VH amino acid sequence that is at least 80%, 85%, 90%, 91%, 92%, 93%, 94%, 95%, 96%, 97%, 98%, or 99% identical to the amino acid sequence of SEQ ID NO: 13, 14, 15, 16, 17, or 18.

In some embodiments, the anti-hIgG antibody or antigen-binding portion has a VL amino acid sequence that is at least 80%, 85%, 90%, 91%, 92%, 93%, 94%, 95%, 96%, 97%, 98%, or 99% identical to the amino acid sequence of SEQ ID NO: 19, 20, 21, 22, 23, or 24.

In some embodiments, the anti-hIgG antibody or antigen-binding portion has VH and VL amino acid sequences that are at least 80%, 85%, 90%, 91%, 92%, 93%, 94%, 95%, 96%, 97%, 98%, or 99% identical, to SEQ ID NOs: 13 and 19, 14 and 20, 15 and 21, 16 and 22, 17 and 23, or 18 and 24, respectively.

In some embodiments, the anti-hIgG antibody has a HC and a LC comprising SEQ ID NOs: 63 and 69, 64 and 70, 65 and 71, 66 and 72, 67 and 73, or 68 and 74, respectively, with or without the leader sequence.

In some embodiments, the anti-hIgG antibody or antigen-binding portion of the present disclosure comprises the HCDR1-3 and LCDR1-3, VH and VL, or HC and LC amino acid sequences of antibody 2C5, 9E6, 11F9, 11G5, 16F5, or 19B1.

The assignment of amino acid numbers and of CDRs may be in accordance with the definitions of Kabat, *Sequences of Proteins of Immunological Interest* (National Institutes of Health, Bethesda, MD (1987 and 1991)). See also Zhang, supra.

An anti-hIgG antibody or antigen-binding portion of the present disclosure can be derivatized or linked to another molecule (e.g., another peptide or protein). In general, the antibodies or portions thereof are derivatized such that IgG binding is not affected adversely by the derivatization or labeling. For example, an antibody or antibody portion of the present disclosure can be functionally linked (by chemical coupling, genetic fusion, noncovalent association or otherwise) to one or more other molecular entities, such as another antibody or a detectable label or tag. Examples include, but are not limited to, radioisotopes or radionuclides (e.g., $^{3}$H, $^{14}$C, $^{15}$N, $^{35}$S, $^{90}$Y $^{99}$Tc, $^{111}$In, $^{125}$I, $^{131}$I), fluorescent labels (e.g., FITC, rhodamine, lanthanide phosphors, phycoerythrin, or the Alexa Fluor® dyes), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), and magnetic agents such as gadolinium chelates. In some embodiments, labels are attached by spacer arms of various lengths to reduce potential steric hindrance.

The present anti-hIgG antibodies and antigen-binding portions of the present disclosure are useful for detecting and/or measuring the level of human IgG or Fab in a sample from an animal (e.g., a non-human primate such as a cynomolgus or rhesus monkey). In some embodiments, the antibodies and antigen-binding portions can be used to detect and/or measure the level of human IgG or Fab in a sample from a human. Suitable detection and measurement methods include immunological methods such as enzyme-linked immunosorbent assays (ELISA), radioimmuno assays, and immunohistology. In some embodiments, the antibodies and antigen-binding portions can be used to detect and/or measure the level of human IgG or Fab in a sample from a human for preclinical or clinical immunohistochemistry (IHC) studies.

Because the rabbit antibodies described herein can bind to distinct epitopes, they can be used alone or used in pairs for the detection of human IgG, in any host animal, to meet the need for therapeutic monoclonal antibody development in preclinical studies. For example, antibodies 16F5, 11F9, and 11G5/19B1/2C5/9E6 bind to three distinct epitopes that are different also from the epitope of MCA5748G. Thus, a pair selected from them that bind to two distinct epitopes may be used together to, e.g., increase assay sensitivity and specificity. For example, 16F5 may be used together with 11F9; 16F5 or 11F9 may be used together with 11G5, 19B1, 2C5, or 9E6; and MCA5748G can used with any one of 16F5, 11F9, 11 G5, 19B1, 2C5, and 9E6. The antibodies in the pair may be labeled differently.

Production of the Anti-hIgG Antibodies

The present anti-hIgG antibodies may be produced by well-known hybridoma technology, in which rabbit B cells producing the antibody of interest are fused with an immortalized cell to form hybridoma cell lines that produce the antibody.

Alternatively, the present hIgG antibodies or antigen-binding portions thereof are produced by recombinant technology using host cells containing nucleotide sequences encoding the heavy and light chains of the antibodies or portions. Accordingly, the present disclosure also provides nucleic acid molecules and sequences encoding anti-IgG antibodies or antigen-binding portions thereof described herein. The nucleotide sequences encoding the heavy chain and light chain amino acid sequences may be introduced to the host cells in two different vectors or on the same vector. They may be expressed under the transcriptional control of a single promoter or two separate promoters.

In some embodiments, the present nucleic acid molecules comprise nucleotide sequences that are at least 70%, 75%, 80%, 85%, 90%, 95%, 97%, 98% or 99% identical to (i) SEQ ID NO: 1, 2, 3, 4, 5, 6, 7, 8, 9, 10, 11, or 12; or (ii) a nucleotide sequence encoding SEQ ID NO: 13, 14, 15, 16, 17, 18, 19, 20, 21, 22, 23, 24, 25, or 26.

The term "percent sequence identity" in the context of amino acid and nucleic acid sequences refers to the residues in two sequences that are the same when aligned for maximum correspondence. For example, the length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure amino acid and nucleotide sequence identity. For instance, polynucleotide sequences can be compared using FASTA, Gap or Bestfit, which are programs in Wisconsin Package Version 10.0, Genetics Computer Group (GCG), Madison, Wisconsin FASTA, which includes, e.g., the programs FASTA2 and FASTA3, provides alignments and percent sequence identity of the regions of the best overlap between the query and search sequences (see, e.g., Pearson, *Methods Enzymol.* (1990) 183:63-98; Pearson, *Methods Mol. Biol.* (2000) 132:185-219; Pearson, *Methods Enzymol.* (1996) 266:227-58; and Pearson, *J. Mol. Biol.* (1998) 276:71-84; incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In particular embodiments, the present disclosure provides a nucleic acid molecule comprising a nucleotide sequence selected from the group consisting of SEQ ID NOs: 1, 2, 3, 4, 5, 6, 7, 8, 9, 10, 11, and 12. In certain embodiments, the nucleic acid molecule comprises the nucleotide sequences of SEQ ID NOs: 1 and 7, 2 and 8, 3 and 9, 4 and 10, 5 and 11, or 6 and 12.

In any of the above embodiments, the nucleic acid molecules may be isolated. Nucleic acid molecules referred to herein as "isolated" or "purified" are nucleic acids which (1) have been separated away from the nucleic acids of the genomic DNA or cellular RNA of their source of origin; and/or (2) do not occur in nature.

In a further aspect, the present disclosure provides a vector suitable for expressing one or both of the chains of an antibody or antigen-binding portion thereof as described herein. The term "vector," as used herein, means a nucleic acid molecule capable of transporting another nucleic acid to which it has been linked. In some embodiments, the vector is a plasmid, i.e., a circular double stranded piece of DNA into which additional DNA segments may be ligated. Moreover, certain vectors are capable of directing the expression of genes to which they are operatively linked. Such vectors are referred to herein as "recombinant expression vectors" (or simply, "expression vectors").

The present disclosure provides vectors comprising nucleic acid molecules that encode the heavy chain, the light chain, or both the heavy and light chains of an anti-hIgG antibody as described herein or an antigen-binding portion thereof. The vector may further comprise an expression control sequence.

The term "expression control sequence" as used herein means polynucleotide sequences that are necessary to affect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

In some embodiments, a nucleic acid molecule as described herein comprises a nucleotide sequence encoding a VH domain from an anti-IgG antibody or antigen-binding portion as described herein joined in-frame to a nucleotide sequence encoding a heavy chain constant region from any source. Similarly, a nucleic acid molecule as described herein can comprise a nucleotide sequence encoding a VL domain from an anti-IgG antibody or antigen-binding portion as described herein joined in-frame to a nucleotide sequence encoding a light chain constant region from any source.

In a further aspect of the present disclosure, nucleic acid molecules encoding the VH and/or VL may be "converted" to full-length antibody genes. In some embodiments, nucleic acid molecules encoding the VH or VL domains are converted to full-length antibody genes by insertion into an expression vector already encoding heavy chain constant (CH) or light chain constant (CL) regions, respectively, such that the VH segment is operatively linked to the CH segment(s) within the vector, and/or the VL segment is operatively linked to the CL segment within the vector. In another aspect, nucleic acid molecules encoding the VH and/or VL domains are converted into full-length antibody genes by linking, e.g., ligating, a nucleic acid molecule encoding a VH and/or VL domain to a nucleic acid molecule encoding a CH and/or CL region using standard molecular biological techniques. Nucleic acid molecules encoding the full-length heavy and/or light chains may then be expressed from a cell into which they have been introduced and the anti-IgG antibody isolated.

In some embodiments, the framework region(s) are mutated so that the resulting framework region(s) have the amino acid sequence of the corresponding germline gene. A mutation may be made in a framework region or constant region, e.g., to increase the half-life of the anti-IgG antibody. See, e.g., PCT Publication WO 00/09560. A mutation in a framework region or constant region also can be made to alter the immunogenicity of the antibody, and/or to provide a site for covalent or noncovalent binding to another molecule. According to the present disclosure, an antibody may have mutations in any one or more of the CDRs or framework regions of the variable domain or in the constant region.

The present disclosure also provides methods for producing the antibody compositions and antibodies and antigen-binding portions thereof described herein. In some embodiments, the present disclosure relates to a method for producing an anti-IgG antibody or antigen-binding portion as described herein, comprising providing a recombinant host cell comprising a nucleotide sequence that encodes the heavy chain or an antigen-binding portion thereof, and a nucleotide sequence that encodes the light chain or an antigen-binding portion thereof, of an anti-IgG antibody or antigen-binding portion described herein; cultivating said host cell under conditions suitable for expression of the antibody or antigen-binding portion; and isolating the resulting antibody or antigen-binding portion. Antibodies or antigen-binding portions produced by such expression in such recombinant host cells are referred to herein as "recombinant" antibodies or antigen-binding portions. The present disclosure also provides progeny cells of such host cells, and antibodies or antigen-binding portions produced by same.

The term "recombinant host cell" (or simply "host cell"), as used herein, means a cell into which a recombinant expression vector has been introduced. By definition, a recombinant host cell does not occur in nature. The present disclosure provides host cells that may comprise, e.g., a vector as described herein. The present disclosure also provides host cells that comprise, e.g., a nucleotide sequence encoding the heavy chain or an antigen-binding portion thereof, a nucleotide sequence encoding the light chain or an antigen-binding portion thereof, or both, of an anti-IgG antibody or antigen-binding portion thereof described herein. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Nucleic acid molecules encoding anti-IgG antibodies and antigen-binding portions thereof and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

It is likely that antibodies expressed by different cell lines or in transgenic animals will have different glycosylation patterns from each other. However, all antibodies encoded by the nucleic acid molecules provided herein, or comprising the amino acid sequences provided herein are part of the present disclosure, regardless of the glycosylation state of the antibodies, and more generally, regardless of the presence or absence of post-translational modification(s).

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents form part of the common general knowledge in the art.

In order that the present disclosure may be better understood, the following examples are set forth. These examples are for purposes of illustration only and are not to be construed as limiting the scope of the present disclosure in any manner.

EXAMPLES

The following examples describe experiments in which a human IgG Fab was used to immunize rabbits and the splenocytes were isolated and used to sort human IgG-specific B-cells. Using cynomolgus monkey IgG as counter screening agent, we obtained six human IgG and Fab specific mAb clones. These clones demonstrated better binding affinity and targeted different epitopes from the only commercially available mouse-origin anti-hIgG mAb clone MCA5748G. These rabbit anti-hIgG mAb clones were evaluated by Gyrolab™ assays and found to be suitable for use as capture reagent in generic pharmacokinetic assays in the presence of cynomolgus monkey serum. The materials and methods for the experiments described herein are as follows.

Chemicals and Reagents

The therapeutic antibodies used in these experiments were a humanized therapeutic monoclonal antibody IgG1 (hIgG1), a humanized development candidate monoclonal antibody IgG4 (hIgG4) and an internal research reagent human Fab (hFab). Cynomolgus monkey IgG (cynoIgG) was purified from cynomolgus monkey serum, purchased from Innovative Research (Novi, MI 48377), by protein A affinity purification. The mouse anti-human IgG monoclonal antibody MCA5748G (Stubenrauch et al., *J Pharm Biomed Anal*. (2009) 49:1003-8) was purchased from BioRad Laboratories (Hercules, CA). Cell culture medium and phosphate-buffered saline (PBS) were purchased from ThermoFisher Scientific (Waltham, MA). All other chemicals were analytical grade.

ELISA for Determination of Binding Specificity

Enzyme-linked immunosorbent assay (ELISA) was used to evaluate the specificity of the antibody clones for binding to human immunoglobulin (IgG) using cynoIgG as control. The ELISA was performed at room temperature on microtiter plates from ThermoFisher Scientific (Waltham, MA), which were first coated with hIgG1, hIgG4 or cynoIgG in PBS for 1 hr. After washing three times with phosphate-buffered saline-polysorbate 20 (Tween 20), the plate was blocked with PBS/3% bovine serum albumin for 1 h. The plate was then washed again and incubated with anti-human IgG antibody clones for 1 h. After another washing step, the bound antibodies were detected by horseradish peroxidase (HRP)-conjugated anti-rabbit IgG antibody from Southern Biotech (Birmingham, AL), according to manufacturer's instructions.

Biacore Assay for Determination of Binding Specificity and Kinetics

The specificity of the rabbit anti-human IgG monoclonal antibody was evaluated in a second assay system as described elsewhere (Chu et al., *Sci Rep*. (2015) 4:7360). These experiments were performed with the Biacore® T200 instrument (Biacore, Uppsala, Sweden) using Streptavidin or CM5 sensor chips from Biacore. Coating of an antibody to streptavidin chip was achieved by injecting biotinylated target antibody, which was amine coupled using the EZ-Link™ Amine-PEG11-Biotin reagent from ThermoFisher Scientific (Waltham, MA) following manufacture's manual. For the CM5 chip, the target antigen or antibody was coupled to the chip surface, via standard amine coupling, using the amine coupling kit from Biacore. Unless otherwise stated, all binding and kinetics assays were performed in HBS-EP+ buffer (0.01 M HEPES pH 7.4, 0.15 M NaCl, 3 mM EDTA, 0.005% v/v Surfactant P20) at 25° C. The dissociation constant values ($K_D$) were calculated with a 1:1 *Langmuir* fitting model using BIAevaluation software V4.1 from Biacore.

Rabbit Immunization and B-Cell Cloning

The hIgG Fab, as described by Wu et al., *Nat Cancer* (2020) 1:86-98, was used to immunize two rabbits with the total of five antigen injections. The primary injection used complete Freund's adjuvant (CFA) and the four boosts used incomplete Freund's adjuvant (IFA). The CFA and IFA were both from ThermoFisher Scientific (Waltham, MA). Serum titers were monitored by ELISA using the antigen protein. The rabbit with higher ELISA titer was chosen for splenectomy.

For B-cell isolation, fresh splenocytes were isolated from the spleen. Approximately $1.2 \times 10^8$ splenocytes were cultured overnight in a special B cell medium customized by Yurogen (Worcester, MA) before sorting. Splenocytes were processed using SMab™ platform at Yurogen to enrich antigen-recognizing B cells. The antigen-sorted B cells were seeded and cultured in a 96-well plate, with 1 cell/well, for 10-14 days.

Antigen-recognizing B-cell clones were identified and confirmed using hIgG4 coated direct ELISA, purified cynoIgG was used in ELISA for counter screening. Antigen-specific B-cell clones were ranked and selected according to the positive/negative ELISA signal ratio and their heavy and light chains of IgG coding sequences were amplified by RT-PCR. The heavy and light chain PCR products were combined and used to transfect HEK293F cells directly. Transiently expressed recombinant rabbit IgG clones were then further confirmed for specific binding to hIgG1, hIgG4 and hFab by ELISA and Biacore binding assays. Upon confirming specific binding to hIgG1, hIgG4 and hFab, the PCR products from the selected positive B-cells were cloned into mammalian expression vector for scale up antibody production in HEK293F cells. Recombinant rabbit mAb clones produced by HEK293F transfection were purified using protein A chromatography for further evaluation.

Gyrolab™ Assay

Gyrolab™ xPlore, Bioaffy 1000 nL CDs, Rexxip A and Rexxip F Buffer from Gyros Protein Technologies (Uppsala Sweden) were used for all experiments (Fraley et al., *Bioanalysis* (2013) 5:1765-74). Biotinylated capture antibodies were diluted to 0.1-0.2 μg/μL in Rexxip A Buffer and flowed over the streptavidin bead column within the microstructure of the Bioaffy CDs. The standard curve and quality control (QC) samples were prepared by spiking the hIgG4 or hFab at the range as indicated in Rexxip A Buffer containing various amount of cynomolgus monkey serum. The standard curve samples, QC samples, mock samples and assay reagents were added to PCR plates and loaded onto the Gyrolab™ instrument. A single replicate of the standard curve, QC samples or mock samples were added into two CD microstructures by the Gyros instrument and then flowed over the bead column. Alexa fluor 647-labeled goat anti-human IgG (Fc) antibody purchased from Southern Biotech (Birmingham, AL) was used as the detection reagent at 2 μg/ml in Rexxip F buffer. A wash solution of PBS with 0.01% v/v Tween-20 was flowed over the columns prior to each run in order to pre-wet the streptavidin beads, and after each step in the assay, to rinse away any unbound reagents. Sample concentrations were determined with the data acquisition at a 1% level of photomultiplication. The Gyrolab™ Evaluator Program was used to analyze results with a 5-parameter fit and 1/Y2 weighting as directed by the manufacture.

Example 1: Isolation of Human IgG-Specific Rabbit Antibody Clones

This example describes experiments in which six rabbit antibody clones recognizing both human IgG and Fab but not cynomolgus monkey IgG were developed using rabbit B-cell cloning technology.

Although hybridoma screening and display methodologies have been used in rabbit monoclonal antibody development, they both have some drawbacks: the hybridoma technology has a low efficiency of cell fusion, while display method results in the loss of natural cognate pairing of heavy and light chain (Zhang et al., *Front Immunol.* (2017) 8:494). To overcome these issues, a single B cell-based antibody gene cloning technology (or single B cell cloning) has been developed recently (Seeber et al., *PLoS ONE* (2014) 9:e86184; Rashidian et al., "Single B Cell Cloning and Production of Rabbit Monoclonal Antibodies" in: Zielonka and Krah (eds) Genotype Phenotype Coupling. Methods in Molecular Biology, vol 2070, Humana, New York, NY, 2020).

Briefly, the single B cell cloning consists of the following steps: (i) isolating specific single B cells from peripheral blood or from lymphoid tissues by antigen-based FACS sorting, (ii) growing and expanding the single B cell for two weeks, (iii) performing RT-PCR with antibody-specific primers to amplify antibody genes and sequencing, (iv) cloning the antibody genes into an expression vector and produce recombinant monoclonal antibody in mammalian cell systems (e.g., HEK 293, CHO cells), and (v) purifying and evaluating recombinant monoclonal antibody by ELISA and other in vitro assays.

We used the human IgG1 Fab to immunize rabbits and the resultant splenocytes were sorted by biotinylated hIgG1, which was a humanized whole IgG1 molecule. A total of 530 primary B cells were single-cell seeded into 96-well plates and grown for two weeks. The B-cell culture medium, which contained monoclonal rabbit IgG antibody, was screened by direct ELISA using hIgG4, hIgG1 and cynoIgG. Based on the ELISA hIgG1/cynoIgG and hIgG4/cynoIgG signal values, we picked 17 clones that had both hIgG1 and hIgG4 OD450>0.9 and CynoIgG OD450<0.2 (Table 1), and their antibody coding sequences were amplified by PCR.

TABLE 1

ELISA screen of PCR product-transfected cell culture medium

| | hIgG4/CynoIgG ELISA | | hIgG1/CynoIgG ELISA | |
|---|---|---|---|---|
| Antigen | hIgG4 (OD450 > 0.9) | CynoIgG (OD450 < 0.2) | hIgG1 (OD450 > 0.9) | CynoIgG (OD450 < 0.2) |
| 16F5 | 1.374 | 0.154 | 1.394 | 0.184 |
| 11G5 | 1.317 | 0.159 | 1.254 | 0.161 |
| 14G6 | 1.311 | 0.169 | 1.583 | 0.141 |
| 2C5 | 1.29 | 0.124 | 1.243 | 0.107 |
| 9E6 | 1.282 | 0.146 | 1.281 | 0.14 |
| 2G11 | 1.203 | 0.083 | 1.375 | 0.073 |
| 12C10 | 1.093 | 0.071 | 1.13 | 0.097 |
| 18C1 | 0.984 | 0.094 | 0.929 | 0.093 |
| 4E5 | 0.961 | 0.093 | 1.201 | 0.08 |
| 2D2 | 0.959 | 0.095 | 0.963 | 0.066 |
| 2G3 | 0.957 | 0.082 | 1.27 | 0.087 |
| 9H11 | 0.957 | 0.074 | 1.029 | 0.068 |
| 19B1 | 0.954 | 0.102 | 1.149 | 0.055 |
| 17E8 | 0.946 | 0.086 | 1.251 | 0.064 |
| 2A7 | 0.945 | 0.101 | 1.036 | 0.046 |
| 20D5 | 0.928 | 0.107 | 1.072 | 0.074 |
| 11F9 | 0.91 | 0.092 | 1.109 | 0.089 |

In eleven of these 17 clones, we were able to obtain PCR products for both heavy and light chains. The heavy and light chain PCR products from each clone were combined at a 1:1 ratio and used to transfect HEK293F cells directly. Cell culture medium from the transfected HEK293F cells was further confirmed by the same ELISA screen assay. Table 2 shows the binding of six of the rabbit recombinant antibody clones with specific binding to whole human IgG (hIgG) and Fab, but not to cynomolgus monkey IgG (cynoIgG), as indicated by the signal ratio of their binding to hIgG1 or hIgG4 versus cynoIgG determined by ELISA assay. These six clones exhibited good hIgG4/cynoIgG and hIgG1/cynoIgG ELISA signal ratio ranging from 4.94 to 14.99.

TABLE 2

Exemplary Rabbit mAbs

| | Selected Clones | | | | | |
|---|---|---|---|---|---|---|
| ELISA Signal Ratio | 2C5 | 9E6 | 11F9 | 11G5 | 16F5 | 19B1 |
| hIgG4/CynoIgG | 7.91 | 9.53 | 5.92 | 5.19 | 6.33 | 12.01 |
| hIgG1/CynoIgG | 7.72 | 10.17 | 6.20 | 4.94 | 5.90 | 14.99 |

These six clones were further analyzed for direct binding to hIgG1, hIgG4, hFab and cynoIgG by Biacore as shown in FIG. 1. All six clones showed various levels of binding to hIgG1, hIgG4 and hFab, but not to cynoIgG. These data indicate that these clones are specific to human IgGs and Fab, but not to cynoIgG.

Example 2: Sequences of Rabbit Anti-hIgG Antibodies

In order to determine the uniqueness of the six clones, heavy and light chain PCR products were subjected to DNA sequencing. The deduced amino acid sequences of the variable regions for the heavy and light chains, respectively, were aligned using the EMBL-EBI web based Clustal Omega (Sievers et al., *Mol Syst Biol.* (2011) 7:539). As shown in FIGS. 2A and 2B, all six clones possess unique amino acid sequences for both heavy and light chains. The phylogenetic trees, based on Clustal Omega, were constructed to visualize relative distances (FIG. 2C). Notably, clone 16F5 is highly divergent from other five clones in both heavy and light chains, whereas clone 11F9 is the next divergent clone in the heavy chain but not in the light chain.

Table 3 shows the nucleotide sequences encoding antibodies 205, 9E6, 11F9, 11 G5, 16F5, and 19B1 (SEQ: SEQ ID NO).

TABLE 3

| | | Nucleotide sequences of exemplary mAbs | |
|---|---|---|---|
| Ab Chain | | Nucleotide Sequence (5' to 3') | SEQ |
| 2C5 | H | ATGGAGACTGGGCTGCGCTGGCTTCTCCTGGTCACTGTGCTCAAAGGTGTCCA<br>GTGTCAGGAGCAGCTGGTGGAGTCCGGGGGAGACCTGGTCAAGCCTGGGGCAT<br>CCCTGACACTCACCTGCACAGCCTCTGGATTCTCCTTCAGTAGCGGCTACTAC<br>ATGTGCTGGGTCCGCCAGGCTCCAGGGAAGGGGCTGGAGTGGATCGCATGCAT<br>TTATGGTGGTGCGCTTACTAATACTTACTACGCGACCTGGGCGAAAGGCCGAT<br>TCACCATCTCCAAGACCTCGTCGACCACGGTGACCCTGCAAATGACCAGTCTG<br>ACAGCCGCGGACACGGCCACCTATTTCTGTGCGAGAGATCTGGGTGCTGCTGG<br>TGATGCTTATAACTTGTGGGGGCCAGGCACCCTGGTCACCGTCTCCTCAGGGC<br>AACCTAAGGCTCCATCAGTCTTCCCACTGGCCCCCTGCTGCGGGACACACCC<br>AGCTCCACGGTGACCCTGGGCTGCCTGGTCAAAGGCTACCTCCCGGAGCCAGT<br>GACCGTGACCTGGAACTCGGGCACCCTCACCAATGGGGTACGCACCTTCCCGT<br>CCGTCCGGCAGTCCTCAGGCCTCTACTCGCTGAGCAGCGTGGTGAGCGTGACC<br>TCAAGCAGCCAGCCCGTCACCTGCAACGTGGCCCACCCAGCCACCAACACCAA<br>AGTGGACAAGACCGTTGCGCCCTCGACATGCAGCAAGCCCATGTGCCCACCCC<br>CTGAACTCCCGGGGGGACCGTCTGTCTTCATCTTCCCCCCAAAACCCAAGGAC<br>ACCCTCATGATCTCACGCACCCCCGAGGTCACATGCGTGGTGGTGGACGTGAG<br>CCAGGATGACCCCGAGGTGCAGTTCACATGGTACATAAACAACGAGCAGGTGC<br>GCACCGCCCGGCCGCCGCTACGGGAGCAGCAGTTCAACAGCACGATCCGCGTG<br>GTCAGCACCCTCCCCATCGCGCACCAGGACTGGCTGAGGGGCAAGGAGTTCAA<br>GTGCAAAGTCCACAACAAGGCACTCCCGGCCCCCATCGAGAAAACCATCTCCA<br>AAGCCAGAGGGCAGCCCCTGGAGCCGAAGGTCTACACCATGGGCCCTCCCCGG<br>GAGGAGCTGAGCAGCAGGTCGGTCAGCCTGACCTGCATGATCAACGGCTTCTA<br>CCCTTCCGACATCTCGGTGGAGTGGGAGAAGAACGGGAAGGCAGAGGACAACT<br>ACAAGACCACGCCGACCGTGCTGGACAGCGACGGCTCCTACTTCCTCTACAGC<br>AAGCTCTCAGTGCCCACGAGTGAGTGGCAGCGGGGCGACGTCTTCACCTGCTC<br>CGTGATGCACGAGGCCTTGCACAACCACTACACGCAGAAGTCCATCTCCCGCT<br>CTCCGGGTAAATAG | 1 |
| 9E6 | H | ATGGAGACTGGGCTGCGCTGGCTTCTCCTGGTCGCTGTGCTCAAAGGTGTCCA<br>GTGTCAGTCGTTGGAGGAGTCCGGGGGAGACCTGGTCAAGCCTGGGGCATCCC<br>TGACACTCACCTGCAAAGCCTCTGGATTCGACTTCAGTAGCAGCTACTACATG<br>TGCTGGGTCCGCCAGGCTCCAGGGAGACTGGAGTGGATCGCATGCATTTATGG<br>TGGTGGTCTGAGTAACACTTACTACGCGGGCTGGGCAAAAGGCCGATTCACCA<br>TCTCCAAAACCTCGTCGACCACGGTGACTCTGCAAATGACCAGTCTGACAGTC<br>GCGGACACGGCCACCTATTTCTGTGCGAGAGATGCTGGGACTAGTGGTGATTA<br>CCTTAACTTGTGGGGCCCGGGCACCCTGGTCACCGTCTCCTCAGGGCAACCTA<br>AGGCTCCATCAGTCTTCCCACTGGCCCCCTGCTGCGGGGACACACCCAGCTCC<br>ACGGTGACCCTGGGCTGCCTGGTCAAAGGCTACCTCCCGGAGCCAGTGACCGT<br>GACCTGGAACTCGGGCACCCTCACCAATGGGGTACGCACCTTCCCGTCCGTCC<br>GGCAGTCCTCAGGCCTCTACTCGCTGAGCAGCGTGGTGAGCGTGACCTCAAGC<br>AGCCAGCCCGTCACCTGCAACGTGGCCCACCCAGCCACCAACACCAAAGTGGA<br>CAAGACCGTTGCGCCCTCGACATGCAGCAAGCCCATGTGCCCACCCCCTGAAC<br>TCCCGGGGGACCGTCTGTCTTCATCTTCCCCCCAAAACCCAAGGACACCCTC<br>ATGATCTCACGCACCCCCGAGGTCACATGCGTGGTGGTGGACGTGAGCCAGGA<br>TGACCCCGAGGTGCAGTTCACATGGTACATAAACAACGAGCAGGTGCGCACCG<br>CCCGGCCGCCGCTACGGGAGCAGCAGTTCAACAGCACGATCCGCGTGGTCAGC<br>ACCCTCCCCATCGCGCACCAGGACTGGCTGAGGGGCAAGGAGTTCAAGTGCAA<br>AGTCCACAACAAGGCACTCCCGGCCCCCATCGAGAAAACCATCTCCAAAGCCA<br>GAGGGCAGCCCCTGGAGCCGAAGGTCTACACCATGGGCCCTCCCCGGGAGGAG<br>CTGAGCAGCAGGTCGGTCAGCCTGACCTGCATGATCAACGGCTTCTACCCTTC<br>CGACATCTCGGTGGAGTGGGAGAAGAACGGGAAGGCAGAGGACAACTACAAGA<br>CCACGCCGACCGTGCTGGACAGCGACGGCTCCTACTTCCTCTACAGCAAGCTC<br>TCAGTGCCCACGAGTGAGTGGCAGCGGGGCGACGTCTTCACCTGCTCCGTGAT<br>GCACGAGGCCTTGCACAACCACTACACGCAGAAGTCCATCTCCCGCTCTCCGG<br>GTAAATAG | 2 |
| 11F9 | H | ATGGAGACTGGGCTGCGCTGGCTTCTCCTGGTCGCTGTGCTCAAAGGTGTCCA<br>GTGTCAGCAGCAGCTGGAGGAGTCCGGGGGAGGCCTGGTCCAGCCTGAGGGAT<br>CCCTGACACTCACCTGCATAGCTTCTGGATTCTCCTTCAGTAGCAGCCACTGG<br>ATATGTTGGGTCCGCCAGGCTCCAGGGAAGGGGCTGGAGTGGATCGCATGCAT | 3 |

TABLE 3-continued

Nucleotide sequences of exemplary mAbs

| Ab Chain | Nucleotide Sequence (5' to 3') | SEQ |
|---|---|---|
| | GTCTACTAGTAGTGGTAGCACTTACGATGCGAACTGGGCGAAAGGCCGATTCA<br>CCATCTCCAAAACCTCGTCGACCACGGTGACTCTGCAAATGACCAGTCTGACA<br>GCCGCGGACACGGCCACCTATTTCTGTGCGAGAGATGTTGGCGGTAGTACTAC<br>TTACTTTGACTTGTGGGGCCCAGGCACCCTGGTCACCGTCTCCTCAGGGCAAC<br>CTAAGGCTCCATCAGTCTTCCCACTGGCCCCCTGCTGCGGGGACACACCCAGC<br>TCCACGGTGACCCTGGGCTGCCTGGTCAAAGGCTACCTCCCGGAGCCAGTGAC<br>CGTGACCTGGAACTCGGGCACCCTCACCAATGGGGTACGCACCTTCCCGTCCG<br>TCCGGCAGTCCTCAGGCCTCTACTCGCTGAGCAGCGTGGTGAGCGTGACCTCA<br>AGCAGCCAGCCCGTCACCTGCAACGTGGCCCACCCAGCCACCAACACCAAAGT<br>GGACAAGACCGTTGCGCCCTCGACATGCAGCAAGCCCATGTGCCCACCCCCTG<br>AACTCCCGGGGGACCGTCTGTCTTCATCTTCCCCCCAAAACCCAAGGACACC<br>CTCATGATCTCACGCACCCCCGAGGTCACATGCGTGGTGGACGTGAGCCA<br>GGATGACCCCGAGGTGCAGTTCACATGGTACATAAACAACGAGCAGGTGCGCA<br>CCGCCCGGCCGCCGCTACGGGAGCAGCAGTTCAACAGCACGATCCGCGTGGTC<br>AGCACCCTCCCCATCGCGCACCAGGACTGGCTGAGGGGCAAGGAGTTCAAGTG<br>CAAAGTCCACAACAAGGCACTCCCGGCCCCCATCGAGAAAACCATCTCCAAAG<br>CCAGAGGGCAGCCCCTGGAGCCGAAGGTCTACACCATGGGCCCTCCCCGGGAG<br>GAGCTGAGCAGCAGGTCGGTCAGCCTGACCTGCATGATCAACGGCTTCTACCC<br>TTCCGACATCTCGGTGGAGTGGGAGAAGAACGGGAAGGCAGAGGACAACTACA<br>AGACCACGCCGACCGTGCTGGACAGCGACGGCTCCTACTTCCTCTACAGCAAG<br>CTCTCAGTGCCCACGAGTGAGTGGCAGCGGGGCGACGTCTTCACCTGCTCCGT<br>GATGCACGAGGCCTTGCACAACCACTACACGCAGAAGTCCATCTCCCGCTCTC<br>CGGGTAAATAG | |
| 11G5 H | ATGGAGACTGGGCTGCGCTGGCTTCTCCTGGTCGCTGTGCTCAAAGGTGTCCA<br>GTGTCAGTCGTTGGAGGAGTCCGGGGGAGACCTGGTCAAGCCTGGGGCATCCC<br>TGACACTCACCTGCACAGCTTCTGGATTCTCCTTCAGTAGCAGCTACTACATG<br>TGCTGGGTCCGCCAGGCTCCAGGGAAGAGGCTGGAGTGGATCGCTTGCATTTA<br>TGGTGGTGGTCTGAGTAACACTTACTACGCGGGCTGGGCAAAAGGCCGATTCA<br>CCATCTCCAAAACCTCGTCGACCACGGTGACTCTGCAAATGACCAGTCTGACA<br>GCCGCGGACACGGCCACCTATTTCTGTGCGAGAGATGCTGGGACTAGTGGTGA<br>TTACCTTAACTTGTGGGGCCCAGGCACCCTGGTCACCGTCTCCTCAGGGCAAC<br>CTAAGGCTCCATCAGTCTTCCCACTGGCCCCCTGCTGCGGGGACACACCCAGC<br>TCCACGGTGACCCTGGGCTGCCTGGTCAAAGGCTACCTCCCGGAGCCAGTGAC<br>CGTGACCTGGAACTCGGGCACCCTCACCAATGGGGTACGCACCTTCCCGTCCG<br>TCCGGCAGTCCTCAGGCCTCTACTCGCTGAGCAGCGTGGTGAGCGTGACCTCA<br>AGCAGCCAGCCCGTCACCTGCAACGTGGCCCACCCAGCCACCAACACCAAAGT<br>GGACAAGACCGTTGCGCCCTCGACATGCAGCAAGCCCATGTGCCCACCCCCTG<br>AACTCCCGGGGGACCGTCTGTCTTCATCTTCCCCCCAAAACCCAAGGACACC<br>CTCATGATCTCACGCACCCCCGAGGTCACATGCGTGGTGGTGGACGTGAGCCA<br>GGATGACCCCGAGGTGCAGTTCACATGGTACATAAACAACGAGCAGGTGCGCA<br>CCGCCCGGCCGCCGCTACGGGAGCAGCAGTTCAACAGCACGATCCGCGTGGTC<br>AGCACCCTCCCCATCGCGCACCAGGACTGGCTGAGGGGCAAGGAGTTCAAGTG<br>CAAAGTCCACAACAAGGCACTCCCGGCCCCCATCGAGAAAACCATCTCCAAAG<br>CCAGAGGGCAGCCCCTGGAGCCGAAGGTCTACACCATGGGCCCTCCCCGGGAG<br>GAGCTGAGCAGCAGGTCGGTCAGCCTGACCTGCATGATCAACGGCTTCTACCC<br>TTCCGACATCTCGGTGGAGTGGGAGAAGAACGGGAAGGCAGAGGACAACTACA<br>AGACCACGCCGACCGTGCTGGACAGCGACGGCTCCTACTTCCTCTACAGCAAG<br>CTCTCAGTGCCCACGAGTGAGTGGCAGCGGGGCGACGTCTTCACCTGCTCCGT<br>GATGCACGAGGCCTTGCACAACCACTACACGCAGAAGTCCATCTCCCGCTCTC<br>CGGGTAAATAG | 4 |
| 16F5 H | ATGGAGACTGGGCTGCGCTGGCTTCTCCTGGTCGCTGTGCTCAAAGGTGTCCA<br>GTGTCAGCAGCAGTTGGAGGAGTCCGGGGGAGGCCTGGTCAAGCCTGGAGGAA<br>CCCTGACACTCACCTGCAAAGCCTCTGGAATCGACTTCAGTAACTACTACTAC<br>ATGTGCTGGGTCCGCCAGGCTCCAGGGAAGGGCTGGAGTTGATCGCATGCAT<br>TTATACTGGTAGTAGTGGTAGCACATGGTACGCGACCTGGGCGAAGGGCCGAT<br>TCACCATCTCCAAAACCTCGTCGACCACGGTGACTCTGCAAATGACCAGTCTG<br>ACAGCCGCGGACACGGCCACCTATTTCTGTGCGAGAGATCGTGATGTTGGTAG<br>TCTTTATGACTCCTTAGATCTCTGGGGCCAGGGCACCCTGGTCACCGTCTCTC<br>AGGGCAACCTAAGGCTCCATCAGTCTTCCCACTGGCCCCCTGCTGCGGGGAC<br>ACACCCAGCTCCACGGTGACCCTGGGCTGCCTGGTCAAAGGCTACCTCCCGGA<br>GCCAGTGACCGTGACCTGGAACTCGGGCACCCTCACCAATGGGGTACGCACCT<br>TCCCGTCCGTCCGGCAGTCCTCAGGCCTCTACTCGCTGAGCAGCGTGGTGAGC<br>GTGACCTCAAGCAGCCAGCCCGTCACCTGCAACGTGGCCCACCCAGCCACCAA<br>CACCAAAGTGGACAAGACCGTTGCGCCCTCGACATGCAGCAAGCCCATGTGCC<br>CACCCCCTGAACTCCCGGGGGACCGTCTGTCTTCATCTTCCCCCCAAAACCC<br>AAGGACACCCTCATGATCTCACGCACCCCCGAGGTCACATGCGTGGTGGTGGA<br>CGTGAGCCAGGATGACCCCGAGGTGCAGTTCACATGGTACATAAACAACGAGC<br>AGGTGCGCACCGCCCGGCCGCCGCTACGGGAGCAGCAGTTCAACAGCACGATC<br>CGCGTGGTCAGCACCCTCCCCATCGCGCACCAGGACTGGCTGAGGGGCAAGGA<br>GTTCAAGTGCAAAGTCCACAACAAGGCACTCCCGGCCCCCATCGAGAAAACCA<br>TCTCCAAAGCCAGAGGGCAGCCCCTGGAGCCGAAGGTCTACACCATGGGCCCT<br>CCCCGGGAGGAGCTGAGCAGCAGGTCGGTCAGCCTGACCTGCATGATCAACGG<br>CTTCTACCCTTCCGACATCTCGGTGGAGTGGGAGAAGAACGGGAAGGCAGAGG<br>ACAACTACAAGACCACGCCGACCGTGCTGGACAGCGACGGCTCCTACTTCCTC | 5 |

TABLE 3-continued

Nucleotide sequences of exemplary mAbs

| Ab Chain | Nucleotide Sequence (5' to 3') | SEQ |
|---|---|---|
| | TACAGCAAGCTCTCAGTGCCCACGAGTGAGTGGCAGCGGGGCGACGTCTTCAC<br>CTGCTCCGTGATGCACGAGGCCTTGCACAACCACTACACGCAGAAGTCCATCT<br>CCCGCTCTCCGGGTAAATAG | |
| 19B1 H | ATGGAGACTGGGCTGCGGTGGCTTCTCCTGGTCGCTGTGCTCAAAGGTGTCCA<br>GTGTCAGGAGCAGCTGGTGGAGTCCGGGGGAGGCCTGGTCCAGCCTGAGGGAT<br>CCCTGACACTCACCTGCACAGCTTCTGGATTCTCCTTCAGTGACAGCTACTAC<br>ATGTGCTGGGTCCGCCAGGCTCCAGGGAAGGGGCTGGAGTGGATCGCATGCAT<br>TTATGGTGGTACTATTACTAATACTTACTACGCGAGCTGGGCGAAAGGCCGAT<br>TCACCATCTCCAAGACCTCGTCGACCACGGTGACCCTGCAAATGACCAGTCTG<br>ACAGCCGCGGACACGGCCACCTATTTCTGTGCGAGAGATCTGGGTGCTGCTGG<br>TGATGCTTATAACTTGTGGGGCCCAGGCACCCTGGTCACCGTCTCCTCAGGGC<br>AACCTAAGGCTCCATCAGTCTTCCCACTGGCCCCCTGCTGCGGGGACACACCC<br>AGCTCCACGGTGACCCTGGGCTGCCTGGTCAAAGGCTACCTCCCGGAGCCAGT<br>GACCGTGACCTGGAACTCGGGCACCCTCACCAATGGGGTACGCACCTTCCCGT<br>CCGTCCGGCAGTCCTCAGGCCTCTACTCGCTGAGCAGCGTGGTGAGCGTGACC<br>TCAAGCAGCCAGCCCGTCACCTGCAACGTGGCCCACCCAGCCACCAACACCAA<br>AGTGGACAAGACCGTTGCGCCCTCGACATGCAGCAAGCCCATGTGCCCACCCC<br>CTGAACTCCCGGGGGACCGTCTGTCTTCATCTTCCCCCCAAAACCCAAGGAC<br>ACCCTCATGATCTCACGCACCCCCGAGGTCACATGCGTGGTGGTGGACGTGAG<br>CCAGGATGACCCCGAGGTGCAGTTCACATGGTACATAAACAACGAGCAGGTGC<br>GCACCGCCCGGCCGCCGCTACGGGAGCAGCAGTTCAACAGCACGATCCGCGTG<br>GTCAGCACCCTCCCCATCGCGCACCAGGACTGGCTGAGGGGCAAGGAGTTCAA<br>GTGCAAAGTCCACAACAAGGCACTCCCGGCCCCCATCGAGAAACCATCTCCA<br>AAGCCAGAGGGCAGCCCCTGGAGCCGAAGGTCTACACCATGGGCCCTCCCCGG<br>GAGGAGCTGAGCAGCAGGTCGGTCAGCCTGACCTGCATGATCAACGGCTTCTA<br>CCCTTCCGACATCTCGGTGGAGTGGGAGAAGAACGGGAAGGCAGAGGACAACT<br>ACAAGACCACGCCGACCGTGCTGGACAGCGACGGCTCCTACTTCCTCTACAGC<br>AAGCTCTCAGTGCCCACGAGTGAGTGGCAGCGGGGCGACGTCTTCACCTGCTC<br>CGTGATGCACGAGGCCTTGCACAACCACTACACGCAGAAGTCCATCTCCCGCT<br>CTCCGGGTAAATAG | 6 |
| 2C5 L | ATGGACACGAGGGCCCCCACTCAGCTGCTGGGGCTCCTGCTGCTCTGGCTCCC<br>AGGTGCCAGATGTGCCTCTGATATGACCCAGACTCCAGCCTCCGTGTCTGCAG<br>CTGTGGGAGGCACAGTCACCATCAAGTGCCAGGCCAGTGAGAGCATTTACAGT<br>GGTTTGGCCTGGTATCAGCAGAAACCAGGGCAGCCTCCCAAGCTCCTGATCTT<br>TGATGCATCCGATCTGGCATCTGGGGTCCCATCGCGGTTCAAAGGCAGTAGAT<br>CTGAGACAGAGTACACTCTCACCATCAGCGACCTGGAGTGTGCCGATGCTGCC<br>ACTTACTACTGTCAATGCACTGATCGTAATAGTATTACTTCTTATGCTTTCGG<br>CGGAGGGACCGAGGTGGTGGTCAAAGGTGATCCAGTTGCACCTACTGTCCTCA<br>TCTTCCCACCAGCTGCTGATCAGGTGGCAACTGGAACAGTCACCATCGTGTGT<br>GTGGCGAATAAATACTTTCCCGATGTCACCGTCACCTGGGAGGTGGATGGCAC<br>CACCCAAACAACTGGCATCGAGAACAGTAAAACACCGCAGAATTCTGCAGATT<br>GTACCTACAACCTCAGCAGCACTCTGACACTGACCAGCACACAGTACAACAGC<br>CACAAAGAGTACACCTGCAAGGTGACCCAGGGCACGACCTCAGTCGTCCAGAG<br>CTTCAATAGGGGTGACTGTTAG | 7 |
| 9E6 L | ATGGACACGAGGGCCCCCACTCAGCTGCTGGGGCTCCTGCTGCTCTGGCTCCC<br>AGGTGCCAGATGTGCCGTCGTGATGACCCAGACTGCATCCCCCGTGTCTGGAG<br>CTGTGGGAGGCACAGTCACCATCAATTGCCAGGCCAGTCAGAGTATTAGTAGT<br>AGCTACTTATCCTGGTATCAGCAGAAACCAGGGCAGCCTCCCAAGCTCCTGAT<br>CTATGGTGCATCCACTCTGGCATCTGGGGTCCCATCGCGGTTCAAAGGCAGTG<br>GATCTGGGACACAGTTCACTCTCACCATCAGTGGCGTGCAGTGTGACGATGCT<br>GCCACTTACTACTGTGCATACGATGCTTATCGTCTCAGTAGTCCTGATAATAT<br>TTTCGGCGGAGGGACCGAGGTGGTGGTCAAAGGTGATCCAGTTGCACCTACTG<br>TCCTCATCTTCCCACCAGCTGCTGATCAGGTGGCAACTGGAACAGTCACCATC<br>GTGTGTGTGGCGAATAAATACTTTCCCGATGTCACCGTCACCTGGGAGGTGGA<br>TGGCACCACCCAAACAACTGGCATCGAGAACAGTAAAACACCGCAGAATTCTG<br>CAGATTGTACCTACAACCTCAGCAGCACTCTGACACTGACCAGCACACAGTAC<br>AACAGCCACAAAGAGTACACCTGCAAGGTGACCCAGGGCACGACCTCAGTCGT<br>CCAGAGCTTCAATAGGGGTGACTGTTAG | 8 |
| 11F9 L | ATGGACACGAGGGCCCCCACTCAGCTGCTGGGGCTCCTGCTGCTCTGGCTCCC<br>AGGTGCCAGATGTGCCTATGATATGACCCAGACTCCAGCCTCCGTGTCTGAAC<br>CTGTGGGAGGCACAGTCACCATCAAGTGCCAGGCCAGTCAGAGCATTAGCAAT<br>GAATTATCCTGGTATCAACAAAAACCAGGGCAGCCTCCCAAACTCCTGATCTA<br>CAGGGCATCCACTCTGGCATCTGGGGTCCCATCGCGGTTCAAAGGCAGTGGAT<br>CTGGGACACAGTTCACTCTCACCATCAACGGCGTGGAGTGTGCCGATGCTGCC<br>ACTTACTACTGTCAACAGGGTTATAGTATTAGTAATGTTGATAATACTTTCGG<br>CGGAGGGACCGAGGTGGTGGTCAAAGGTGATCCAGTTGCACCTACTGTCCTCA<br>TCTTCCCACCAGCTGCTGATCAGGTGGCAACTGGAACAGTCACCATCGTGTGT<br>GTGGCGAATAAATACTTTCCCGATGTCACCGTCACCTGGGAGGTGGATGGCAC<br>CACCCAAACAACTGGCATCGAGAACAGTAAAACACCGCAGAATTCTGCAGATT<br>GTACCTACAACCTCAGCAGCACTCTGACACTGACCAGCACACAGTACAACAGC<br>CACAAAGAGTACACCTGCAAGGTGACCCAGGGCACGACCTCAGTCGTCCAGAG<br>CTTCAATAGGGGTGACTGTTAG | 9 |

TABLE 3-continued

Nucleotide sequences of exemplary mAbs

| Ab Chain | Nucleotide Sequence (5' to 3') | SEQ |
|---|---|---|
| 11G5 L | ATGGACACGAGGGCCCCCACTCAGCTGCTGGGGCTCCTGCTGCTCTGGCTCCC<br>AGGTGCCAGATGTGCCGTCGTGATGACCCAGACTGCATCCCCGTGTCTGGAG<br>CTGTGGGAGGCACAGTCACCATCAATTGCCAGGCCAGTCAGAGTATTAGTGCT<br>AGCGCCTTATCCTGGTATCAACAGAAACCAGGGCAGCCTCCCAAGCTCCTGAT<br>CTATGCTGCATCCACTCTGGAATCTGGGGTCCCATCGCGGTTCAAAGGCAGTG<br>GATCTGGGACACAGTTCACTCTCACCATCAGCGGCGTGCAGTGTGACGATGCT<br>GCCACTTACTACTGTGCATACGATGGTTATCGTCTCAGTAGTGCTGATAATAT<br>TTTCGGCGGAGGGACCGAGGTGGTGGTCAAAGGTGATCCAGTTGCACCTACTG<br>TCCTCATCTTCCCACCAGCTGCTGATCAGGTGGCAACTGGAACAGTCACCATC<br>GTGTGTGTGGCGAATAAATACTTTCCCGATGTCACCGTCACCTGGGAGGTGGA<br>TGGCACCACCCAAACAACTGGCATCGAGAACAGTAAAACACCGCAGAATTCTG<br>CAGATTGTACCTACAACCTCAGCAGCACTCTGACACTGACCAGCACACAGTAC<br>AACAGCCACAAAGAGTACACCTGCAAGGTGACCCAGGGCACGACCTCAGTCGT<br>CCAGAGCTTCAATAGGGGTGACTGTTAG | 10 |
| 16F5 L | ATGGACACGAGGGCCCCCACTCAGCTGCTGGGGCTCCTGCTGCTCTGGCTCCC<br>AGGTGCCAGATGTGCCTATGATATGACCCAGACTCCAGCCTCCGTGGAGGCAG<br>CTGTGGGAGGCACAGTCACCATCAATTGCCAGGCCAGTCAGAGCATTAATAAT<br>TGGTTATCCTGGTATCAGCAGAAACCAGGGCAGCGTCCCAAGCTCCTGATTTA<br>CCAGGCATCCACTCTGGCATCTGGGGTCTCATCGCGGTTCAAAGGCAGTGGAT<br>CTGGGACACACTTTACTCTCACCATCAGCGACCTGGAGTGTGCCGATGCTGCC<br>ACTTACTACTGTCAACAGGGTTGGAGTATAGACGATATTGATAATGCTTTCGG<br>CGGAGGGACCGAGGTGGTGGTCAAGGGTGATCCAGTTGCACCTACTGTCCTCA<br>TCTTCCCACCAGCTGCTGATCAGGTGGCAACTGGAACAGTCACCATCGTGTGT<br>GTGGCGAATAAATACTTTCCCGATGTCACCGTCACCTGGGAGGTGGATGGCAC<br>CACCCAAACAACTGGCATCGAGAACAGTAAAACACCGCAGAATTCTGCAGATT<br>GTACCTACAACCTCAGCAGCACTCTGACACTGACCAGCACACAGTACAACAGC<br>CACAAAGAGTACACCTGCAAGGTGACCCAGGGCACGACCTCAGTCGTCCAGAG<br>CTTCAATAGGGGTGACTGTTAG | 11 |
| 19B1 L | ATGGACACGAGGGCCCCCACTCAGCTGCTGGGGCTCCTGCTGCTCTGGCTCCC<br>AGGTGCCAGATGTGCCTCTGATATGACCCAGACTCCAGCCTCCGTGTCTGAAC<br>CTGTGGGAGGCACAGTCACCATCAAGTGCCAGGCCAGTGAGAACATTTACAGC<br>TCTTTAGCCTGGTATCAGCAGAAACCAGGGCAGCCTCCCAAGCTCCTGATCTA<br>TGATGCATCCAATCTGGCATCTGGGGTCCCATCGCGGTTCAGCGGCAGTGGAT<br>CTGGGACAGAGTTCACTCTCACCATCAGCGACCTGGAGTGTGCCGATGCTGCC<br>ACTTACTACTGTCAATGCACTTATCGTAGTAGTAGTAGTTCTTATGCTTTCGG<br>CGGAGGGACCGAGGTGGTGGTCAAAGGTGATCCAGTTGCACCTACTGTCCTCA<br>TCTTCCCACCAGCTGCTGATCAGGTGGCAACTGGAACAGTCACCATCGTGTGT<br>GTGGCGAATAAATACTTTCCCGATGTCACCGTCACCTGGGAGGTGGATGGCAC<br>CACCCAAACAACTGGCATCGAGAACAGTAAAACACCGCAGAATTCTGCAGATT<br>GTACCTACAACCTCAGCAGCACTCTGACACTGACCAGCACACAGTACAACAGC<br>CACAAAGAGTACACCTGCAAGGTGACCCAGGGCACGACCTCAGTCGTCCAGAG<br>CTTCAATAGGGGTGACTGTTAG | 12 |

Table 4 shows the deduced amino acid sequences of the variable domains of antibodies 2C5, 9E6, 11F9, 11 G5, 16F5, and 19B1. The complementarity-determining regions (CDRs) are in boldface and underlined.

TABLE 4

Variable domain amino acid sequences of exemplary antibodies

| Ab Chain | Sequence (N-terminus to C-terminus) | SEQ |
|---|---|---|
| 2C5 VH | QEQLVESGGD LVKPGASLTL TCTASGFSFS SGYYMCWVRQ APGKGLEWIA CIYGGALTNT YYATWAKGRF TISKTSSTTV TLQMTSLTAA DTATYFCARD LGAAGDAYNL WGPGTLVTVS S | 13 |
| 9E6 VH | QSLEESGGDL VKPGASLTLT CKASGFDFSS SYYMCWVRQA PGRLEWIACI YGGGLSNTYY AGWAKGRFTI SKTSSTTVTL QMTSLTVADT ATYFCARDAG TSGDYLNLWG PGTLVTVSS | 14 |
| 11F9 VH | QQQLEESGGG LVQPEGSLTL TCIASGFSFS SSHWICWVRQ APGKGLEWIA CMSTSSGSTY DANWAKGRF ISKTSSTTVT LQMTSLTAAD TATYFCARDV GGSTTYFDLW GPGTLVTVSS | 15 |
| 11G5 VH | QSLEESGGDL VKPGASLTLT CTASGFSFSS SYYMCWVRQA PGKRLEWIAC IYGGGLSNTY YAGWAKGRFT ISKTSSTTVT LQMTSLTAAD TATYFCARDA TSGDYLNLWG PGTLVTVSS | 16 |

TABLE 4-continued

Variable domain amino acid sequences of exemplary antibodies

| Ab | Chain | Sequence (N-terminus to C-terminus) | SEQ |
|---|---|---|---|
| 16F5 | VH | QQQLEESGGG LVKPGGTLTL TCKASGIDFS NYYYMCWVRQ APGKGLELIA CIYTGSSGST WYATWAKGRF TISKTSSTTV TLQMTSLTAA DTATYFCARD RDVGSLYDSL DLWGQGTLVT VSP | 17 |
| 19B1 | VH | QEQLVESGGG LVQPEGSLTL TCTASGFSFS DSYYMCWVRQ APGKGLEWIA CIYGGTITNT YYASWAKGRF TISKTSSTTV TLQMTSLTAA DTATYFCARD LGAAGDAYNL WGPGTLVTVS S | 18 |
| 2C5 | VL | ASDMTQTPAS VSAAVGGTVT IKCQASESIY SGLAWYQQKP GQPPKLLIFD ASDLASGVPS RFKGSRSETE YTLTISDLEC ADAATYYCQC TDRNSITSYA FGGGTEVVVK | 19 |
| 9E6 | VL | AVVMTQTASP VSGAVGGTVT INCQASQSIS SSYLSWYQQK PGQPPKLLIY GASTLASGVP SRFKGSGSGT QFTLTISGVQ CDDAATYYCA YDAYRLSSPD NIFGGGTEVV VK | 20 |
| 11F9 | VL | AYDMTQTPAS VSEPVGGTVT IKCQASQSIS NELSWYQQKP GQPPKLLIYR ASTLASGVPS RFKGSGSGTQ FTLTINGVEC ADAATYYCQQ GYSISNVDNT FGGGTEVVVK | 21 |
| 11G5 | VL | AVVMTQTASP VSGAVGGTVT INCQASQSIS ASALSWYQQK PGQPPKLLIY AASTLESGVP SRFKGSGSGT QFTLTISGVQ CDDAATYYCA YDGYRLSSAD NIFGGGTEVV VK | 22 |
| 16F5 | VL | AYDMTQTPAS VEAAVGGTVT INCQASQSIN NWLSWYQQKP GQRPKLLIYQ ASTLASGVSS RFKGSGSGTH FTLTISDLEC ADAATYYCQQ GWSIDDIDNA FGGGTEVVVK | 23 |
| 19B1 | VL | ASDMTQTPAS VSEPVGGTVT IKCQASENIY SSLAWYQQKP GQPPKLLIYD ASNLASGVPS RFSGSGSGTE FTLTISDLEC ADAATYYCQC TYRSSSSSYA FGGGTEVVVK | 24 |

Table 5 shows heavy and light chain constant region amino acid sequences (CH and CL, respectively) of the six antibodies 2C5, 9E6, 11F9, 11 G5, 16F5, and 19B31.

TABLE 5

Constant region amino acid sequences of exemplary antibodies

| Ab | Chain | Sequence (N-terminal to C-terminus) | SEQ |
|---|---|---|---|
| CH | | GQPKAPSVFP LAPCCGDTPS STVTLGCLVK GYLPEPVTVT WNSGTLTNGV RTFPSVRQSS GLYSLSSVVS VTSSSQPVTC NVAHPATNTK VDKTVAPSTC SKPMCPPPEL PGGPSVFIFP PKPKDTLMIS RTPEVTCVVV DVSQDDPEVQ FTWYINNEQV RTARPPLREQ QFNSTIRVVS TLPIAHQDWL RGKEFKCKVH NKALPAPIEK TISKARGQPL EPKVYTMGPP REELSSRSVS LTCMINGFYP SDISVEWEKN GKAEDNYKTT PTVLDSDGSY FLYSKLSVPT SEWQRGDVFT CSVMHEALHN HYTQKSISRS PGK | 25 |
| CL | | GDPVAPTVLI FPPAADQVAT GTVTIVCVAN KYFPDVTVTW EVDGTTQTTG IENSKTPQNS ADCTYNLSST LTLTSTQYNS HKEYTCKVTQ GTTSVVQSFN RGDC | 26 |

Table 6 shows heavy CDR (HCDR) and light chain CDR (LCDR) amino acid sequences of antibodies 2C5, 9E6, 11F9, 11 G5, 16F5, and 19B31, wherein the CDRs are defined according to the Kabat numbering system. The SEQ ID NOs of the sequences are shown in parentheses.

TABLE 6

CDR amino acid sequences of exemplary antibodies

Amino Acid Sequence (N-terminus to C-terminus)

| Ab | HCDR1 | HCDR2 | HCDR3 | LCDR1 | LCDR2 | LCDR3 |
|---|---|---|---|---|---|---|
| 2C5 | FSFSSGYYMC (27) | WIACIYGGAL TNTYYATWA (28) | ARDLGAAGDA YN (29) | ESIYSGLA (30) | LLIFDASDLA S (31) | QCTDRNSITS YA (32) |

TABLE 6-continued

CDR amino acid sequences of exemplary antibodies

Amino Acid Sequence (N-terminus to C-terminus)

| Ab | HCDR1 | HCDR2 | HCDR3 | LCDR1 | LCDR2 | LCDR3 |
|---|---|---|---|---|---|---|
| 9E6 | FDFSSSYYMC (33) | WIACIYGGGL SNTYYAGWA (34) | ARDAGTSGDY LN (35) | QSISSSYL S (36) | LLIYGASTLA S (37) | AYDAYRLSSP DNI (38) |
| 11F9 | FSFSSSHWIC (39) | WIACMSTSSG STYDANWA (40) | ARDVGGSTTY FD (41) | QSISNELS (42) | LLIYRASTLA S (43) | QQGYSISNVD NT (44) |
| 11G5 | FSFSSSYYMC (45) | WIACIYGGGL SNTYYAGWA (46) | ARDAGTSGDY LN (47) | QSISASAL (48) | LLIYAASTLE S (49) | AYDGYRLSSA DNI (50) |
| 16F5 | IDFSNYYYMC (51) | LIACIYTGSS GSTWYATWA (52) | ARDRDVGSLY DSLD (53) | QSINNWLS (54) | LLIYQASTLA S (55) | QQGWSIDDID NA (56) |
| 19B1 | FSFSDSYYMC (57) | WIACIYGGTI TNTYYASWA (58) | ARDLGAAGDA YN (59) | ENIYSSLA (60) | LLIYDASNLA S (61) | QCTYRSSSSS YA (62) |

Table 7 shows SEQ ID NO information for antibodies 2C5, 9E6, 11F9, 11 G5, 16F5, and 19B1. Except as indicated by "nt" (nucleotides), all sequences in the table are amino acid sequences.

TABLE 7

SEQ ID NOs for 2C5, 9E6, 11F9, 11G5, 16F5, and 19B1

| Clone | HC (nt.) | LC (nt.) | VH | VL | CH | CL | HC | LC | HCDR 1 | HCDR 2 | HCDR 3 | LCDR 1 | LCDR 2 | LCDR 3 |
|---|---|---|---|---|---|---|---|---|---|---|---|---|---|---|
| 2C5 | 1 | 7 | 13 | 19 | 25 | 26 | 63 | 69 | 27 | 28 | 29 | 30 | 31 | 32 |
| 9E6 | 2 | 8 | 14 | 20 | 25 | 26 | 64 | 70 | 33 | 34 | 35 | 36 | 37 | 38 |
| 11F9 | 3 | 9 | 15 | 21 | 25 | 26 | 65 | 71 | 39 | 40 | 41 | 42 | 43 | 44 |
| 11G5 | 4 | 10 | 16 | 22 | 25 | 26 | 66 | 72 | 45 | 46 | 47 | 48 | 49 | 50 |
| 16F5 | 5 | 11 | 17 | 23 | 25 | 26 | 67 | 73 | 51 | 52 | 53 | 54 | 55 | 56 |
| 19B1 | 6 | 12 | 18 | 24 | 25 | 26 | 68 | 74 | 57 | 58 | 59 | 60 | 61 | 62 |

Example 3: Binding Affinity and Epitope of the Rabbit Anti-hIgG Antibodies

The amplified PCR products containing the heavy and light chain antibody coding sequences were cloned into expression vectors and used for transient transfection and antibody purification. Using amine coupling, a mouse anti-rabbit mAb was directly immobilized on CM5 chip (Chu et al., *Sci Rep.* (2015) 4:7360). The purified rabbit mAb clones were then injected, followed by flow over 1:2 serially diluted hFab, hIgG1, hIgG4 and cynoIgG, ranging from 80-0 nM.

As illustrated in Table 8, all the clones exhibited a binding affinity ($K_D$) greater than sub-nanomolar to the hIgG1, hIgG4 and hFab, but not to cynoIgG. Under the same conditions, the control commercial clone MCA5748G (Bio-Rad, Hercules, CA), however, was able to bind to hIgG1 and hIgG4, but not hFab and cynoIgG.

TABLE 8

Biacore kinetics of binding of rabbit mAb clones to different antibody types

| Sample | Antigen | ka (1/Ms) | kd (1/s) | KD (M) |
|---|---|---|---|---|
| 11F9 | hFab | 2.97E+07 | 3.34E-02 | 1.12E-09 |
| | hIgG4 | 1.45E+05 | 4.06E-05 | 2.79E-10 |
| | hIgG1 | 1.49E+05 | 9.21E-05 | 6.19E-10 |
| | cynoIgG | | no binding | |
| 11G5 | hFab | 8.99E+05 | 5.31E-04 | 5.91E-10 |
| | hIgG4 | 1.35E+05 | 5.80E-06 | 4.29E-11 |
| | hIgG1 | 1.35E+05 | 2.52E-05 | 1.87E-10 |
| | cynoIgG | | no binding | |
| 16F5 | hFab | 3.02E+06 | 5.84E-03 | 1.93E-09 |
| | hIgG4 | 1.57E+05 | 8.09E-05 | 5.14E-10 |
| | hIgG1 | 1.73E+05 | 2.21E-05 | 1.27E-10 |
| | cynoIgG | | no binding | |
| 19B1 | hFab | 1.22E+06 | 6.58E-04 | 5.40E-10 |
| | hIgG4 | 1.36E+05 | 9.14E-06 | 6.70E-11 |
| | hIgG1 | 1.37E+05 | 3.28E-05 | 2.39E-10 |
| | cynoIgG | | no binding | |

TABLE 8-continued

Biacore kinetics of binding of rabbit mAb clones to different antibody types

| Sample | Antigen | ka (1/Ms) | kd (1/s) | KD (M) |
|---|---|---|---|---|
| 2C5 | hFab | 2.65E+06 | 1.46E−03 | 5.50E−10 |
|  | hIgG4 | 1.35E+05 | 1.36E−05 | 1.00E−10 |
|  | hIgG1 | 1.37E+05 | 3.80E−05 | 2.77E−10 |
|  | cynoIgG |  | no binding |  |
| 9E6 | hFab | 1.16E+07 | 6.03E−03 | 5.18E−10 |
|  | hIgG4 | 1.37E+05 | 2.68E−05 | 1.96E−10 |
|  | hIgG1 | 1.43E+05 | 6.10E−05 | 4.26E−10 |
|  | cynoIgG |  | no binding |  |
| MCA5748G | hFab |  | no binding |  |
|  | hIgG4 | 1.34E+05 | 2.36E−04 | 1.57E−09 |
|  | hIgG1 | 1.47E+05 | 2.81E−04 | 1.82E−09 |
|  | cynoIgG |  | no binding |  |

Figure 3A:
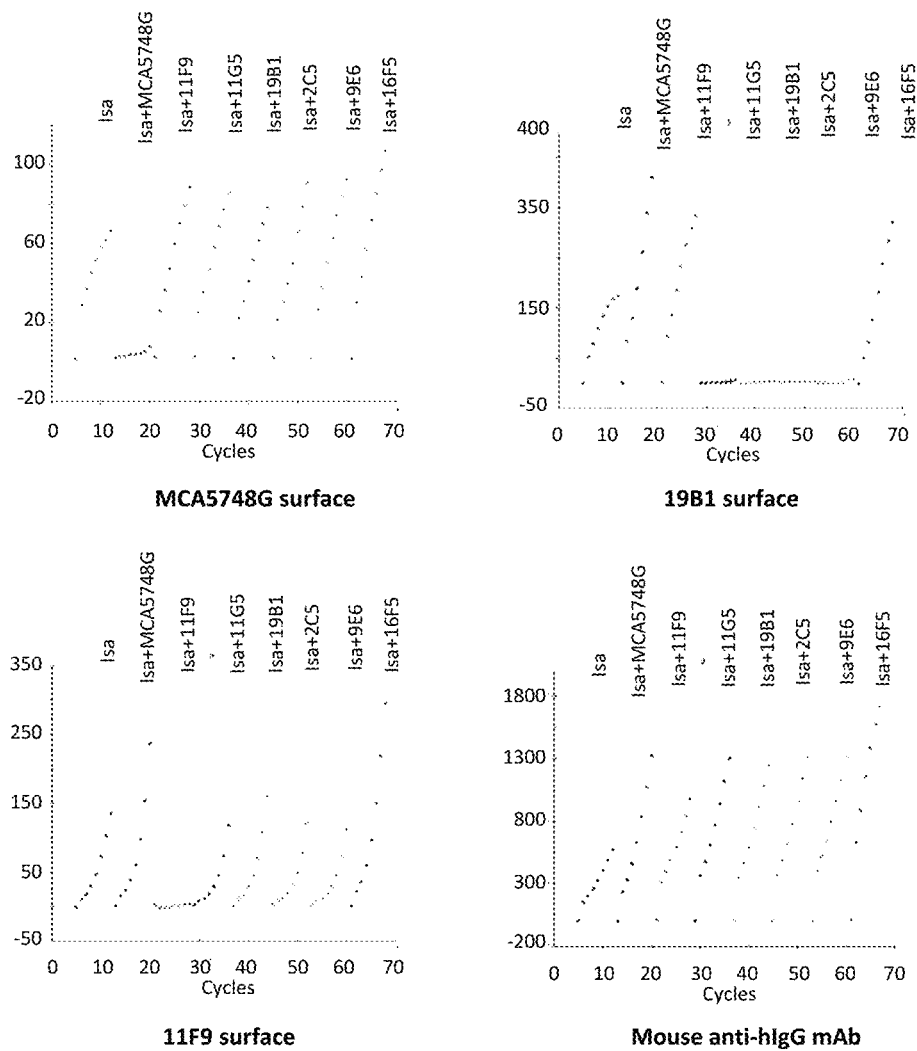
FIGS. 3A and 3B show the epitope determination of the six rabbit anti-hIgG clones by Biacore competition assay (FIG. 3A) and Biacore kinetics assay sensorgram (FIG. 3B). Antibodies MCA5748G (Bio-Rad), 19B1, 11F9 and mouse anti-hIgG mAb (Southern Biotech Cat #9042-01) were first biotinylated and captured on Biacore SA chip at 500-600 RUs, and 8 times 1:2 serially diluted (80-0 nM) hIgG1 antibody (isatuximab; "isa") was premixed with each of the competition antibodies (240 nM). When the pre-mixed competition antibody binds to hIgG1 at the same site as the antibody captured on the chip surface, it prevents hIgG1 from binding to the captured antibody.
Figure 3B:
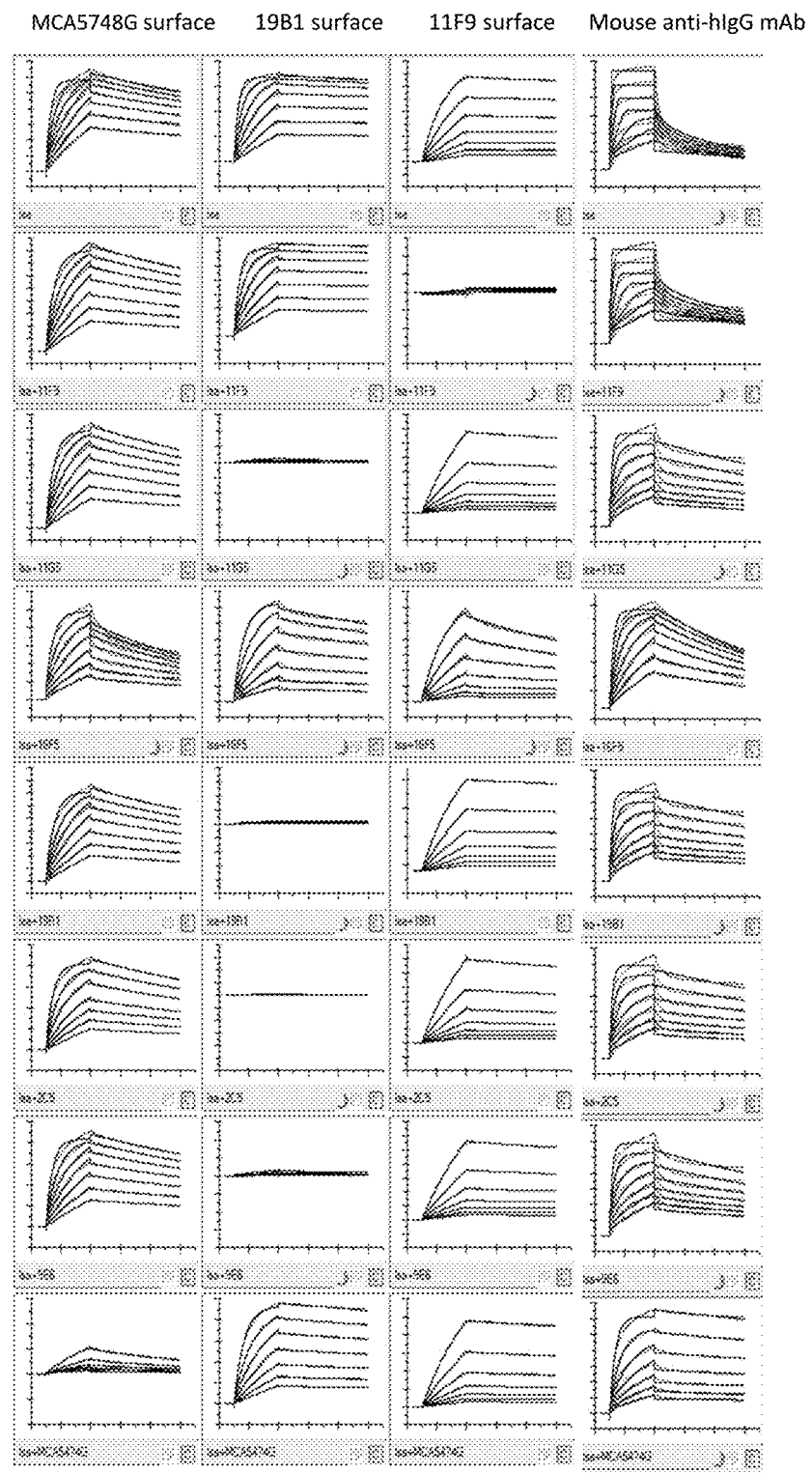

In order to determine if the six rabbit anti-hIgG clones had a different epitope from the only commercially available clone MCA5748G, the MCA5748G, 19B1 and 11F9 clones and a mouse anti-hIgG mAb (as the assay control) were biotinylated. These biotinylated antibodies were then injected into the different flow cells of a streptavidin chip, to reach a range between 500-600 RUs, followed by flow over the 1:2 serially diluted hIgG1 antibody, ranging from 80-0 nM, in the presence of 240 nm of the different rabbit mAb clones as the competitor. As shown in FIGS. 3A and 3B, when MCA5748G was used as the capture antibody on the chip surface, competition was only seen with the clone MAC5748G itself, indicating that this commercial mouse anti-hIgG clone MAC5748G has a different epitope from all the six rabbit anti-hIgG clones disclosed herein.

When the rabbit anti-hIgG clone 19B1 was used as the capture antibody on the chip surface, competition was seen with clones 11 G5, 19B1, 2C5 and 9E6. Therefore, the epitope of these four clones are the same, but different from clone 11F9 and 16F5. Furthermore, when clone 11F9 was captured on the chip surface, competition was only seen with clone 11F9 itself, not with clone 16F5, nor with any of the other four clones which share the same epitope. Thus, clone 16F5 also has a different epitope from clone 11F9. These results indicated that clones 16F5 and 11F9 each has a unique epitope whereas the clones 11 G5, 19B1, 2C5 and 9E6 share the same epitope. Paratopes in CDRs determine antibody binding epitopes and the heavy chain plays the dominant role, the epitope classification of the six rabbit anti-hIgG clones correlate well with the phylogenetic tree's relationship (FIG. 2C).

Additional Biacore experiments have shown that all six rabbit anti-hIgG clones are capable of binding to each of the 10 different human IgGs, and the 2 Fabs tested. The ten antibodies included those having human IgG1 and IgG4. Because Fab was used as the immunogen to generate these rabbit anti-hIgG mAb clones, all of them should bind within the Fab region of the IgG. Because different human IgG subtypes (IgG1, IgG2, IgG3 and IgG4) are classified by their Fc sequences, which are not part of the Fab region, all six of the rabbit anti-hIgG antibody clones should be able to recognize all subtypes of human IgGs. This is a significant advantage when these rabbit anti-hIgG mAbs are used for the detection of different subtypes therapeutic human IgG (e.g., IgG1, IgG2, and IgG4) molecules in preclinical studies and/or in process development.

In summary, amino acid sequence alignment showed that all six clones obtained herein were unique and diverse. They bound to three different epitope groups (16F5; 11F9; and 11 G5/19B1/2C5/9E6) and demonstrated better binding affinity and targeted different epitopes from the only commercially available mouse-origin anti-hIgG antibody clone, MCA5748G. Clones with different binding epitopes can be used to develop pair-wise human IgG detection assays, such as "sandwich" ELISAs and Gyrolab™ assays.

Example 4: Specific Detection of Human IgG by Rabbit Antibodies in Gyrolab™ Assay In order to test if the rabbit anti-hIgG mAb can detect human IgG molecule in the presence of monkey serum, biotinylated clone 16F6 was first used as the capture reagent. Gyrolab™ xPlore, Bioaffy 1000 nL CDs, Rexxip A and Rexxip F Buffer from Gyros Protein Technologies (Uppsala Sweden) were used for all experiments. Biotinylated capture antibodies were diluted to 0.1-0.2 µg/µL in Rexxip A Buffer and flowed over the streptavidin bead column within the microstructure of the Bioaffy CDs. The standard curve and quality control (QC) samples were prepared by spiking the hIgG4 or hFab at the range as indicated in Gyrolab™ Rexxip A Buffer mixed with 0, 4%, 10% and 25% cynomolgus monkey serum. The human IgG4 antibody hIgG4 was used to prepare the standard curve, which was a 1:4 dilution at a range between 1200-0.3 ng/ml in assay matrix.

Figure 4A:
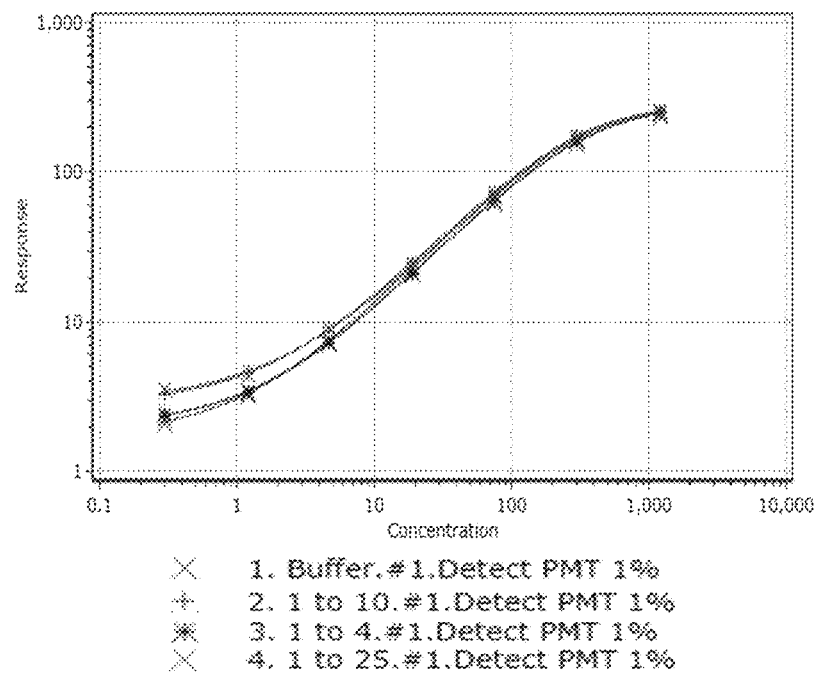
Figure 4B:
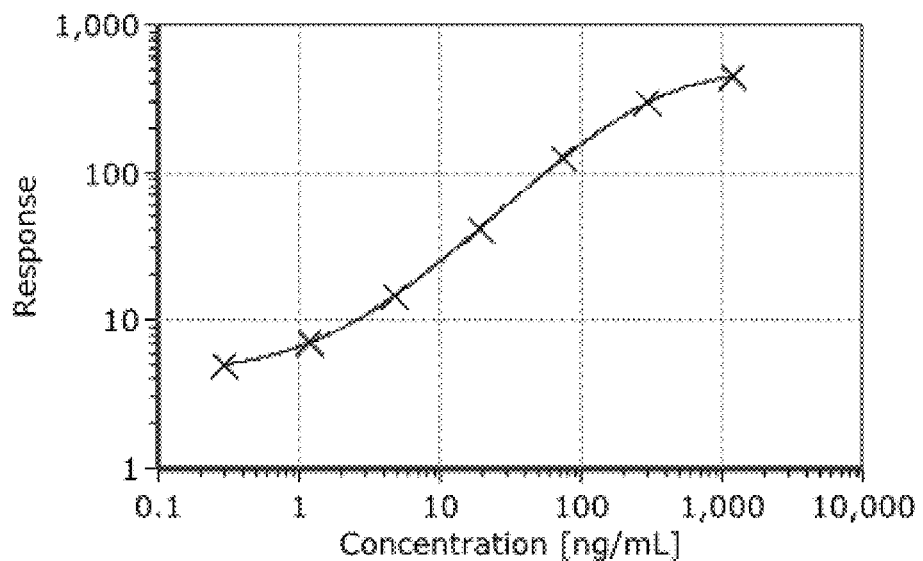

As shown in FIG. 4A, at the range of 1200-0.3 ng/ml, no matrix effect was observed at the cynomolgus monkey serum concentrations between 0 and 4%. When the assay matrix contained 10% and 25% of the cynomolgus monkey serum, some minor background signal was observed at the lower half of the standard curve. Therefore, the assay matrix containing 4% cynomolgus monkey serum was further tested with three QCs (750, 40 and 0.6 ng/ml of hIgG4) using the same standard curve. As shown in FIGS. 4B and 4C, an exemplary standard curve was obtained and two of the three QCs met both <20% bias and <20% CV, whereas the high QC had just missed the bias cut off by 0.9% (20.9%) and its CV was exemplary (4.56%).

We further tested the suitability of other rabbit anti-hIgG clones to be used as the capture reagent in Gyrolab™ assay. All six rabbit anti-hIgG clones, along with the commercial mouse anti-hIgG mAb MCA5748G clone, were biotinylated and used at similar a concentration in the Gyrolab™ assay. The Gyrolab™ generic PK assay capture reagent was used as control. As shown in FIGS. 5A and 5B, when the whole antibody molecule hIgG4 was used as the standard (same range form 1200-0.3 ng/ml), all the capture reagents generated a concentration-dependent curves with the highest background seen with the commercial clone MCA5748G. However, when Fab antibody molecule hFab was used as the standard (same range form 1200-0.3 ng/ml), all six rabbit anti-hIgG capture reagents generated concentration-dependent curves as well. In contrast, both the commercial mouse anti-hIgG clone MAC5748G and the control Gyrolab™ capture reagent failed to produce concentration-dependent curves.

Example 5: Dynamic Range of Rabbit mAb Clones in Gyrolab™ Assay

One advantage of the Gyrolab™ assay is that it offers significantly greater dynamic range compared to surface-based assay platforms such as ELISA and MSD (Fraley et al., *Bioanalysis* (2015) 5-1765-74). The human whole antibody hIgG4 was once again used to prepare the assay standard, which was a linear 6-point 1:5 dilution in the range of 5000-0.32 ng/ml as shown in Table 9.

TABLE 9

Performance of different capture reagents by Gyrolab™ assay

| Capture | Exp. Conc | Av. Resp. | Calc Conc | Av. Bias | S/B |
|---|---|---|---|---|---|
| Gyrolab™ Capture | 0 | 4.5 | NaN | NaN | 1.0 |
| | 0.32 | 4.6 | 0.4 | 20.1 | 1.0 |
| | 1.6 | 5.3 | 1.4 | −9.4 | 1.2 |
| | 8 | 9.3 | 8.3 | 3.1 | 2.1 |
| | 40 | 26.1 | 39.5 | −1.3 | 5.7 |
| | 200 | 94.1 | 201.2 | 0.6 | 20.8 |
| | 1000 | 267.3 | 997.3 | −0.3 | 59.0 |
| | 5000 | 467.6 | 5005.7 | 0.1 | 103.2 |
| MCA5748G | 0 | 11.8 | NaN | NaN | 1.0 |
| | 0.32 | 13.6 | 0.4 | 37.0 | 1.2 |
| | 1.6 | 14.2 | 1.3 | −17.1 | 1.2 |
| | 8 | 18.4 | 8.2 | 2.6 | 1.6 |
| | 40 | 33.8 | 40.4 | 1.0 | 2.9 |
| | 200 | 86.7 | 196.8 | −1.6 | 7.4 |
| | 1000 | 213.5 | 1021.5 | 2.2 | 18.1 |
| | 5000 | 282.9 | 4454.3 | −10.9 | 24.0 |
| 16F5 | 0 | 3.9 | NaN | NaN | 1.0 |
| | 0.32 | 4.4 | 0.3 | 2.2 | 1.1 |
| | 1.6 | 7.0 | 1.6 | −1.6 | 1.8 |
| | 8 | 18.5 | 8.0 | −0.1 | 4.7 |
| | 40 | 64.2 | 40.6 | 1.5 | 16.4 |
| | 200 | 197.2 | 196.0 | −2.0 | 50.5 |
| | 1000 | 368.7 | 1072.2 | 7.2 | 94.4 |
| | 5000 | 385.2 | 2171.9 | −56.6 | 98.6 |
| 9E6 | 0 | 2.9 | NaN | NaN | 1.0 |
| | 0.32 | 3.0 | 0.3 | −3.26 | 1.1 |
| | 1.6 | 4.1 | 1.6 | 1.65 | 1.4 |
| | 8 | 8.6 | 8.0 | −0.32 | 3.0 |
| | 40 | 28.4 | 39.9 | −0.16 | 9.8 |
| | 200 | 102.9 | 200.5 | 0.26 | 35.5 |
| | 1000 | 255.8 | 997.7 | −0.23 | 88.2 |
| | 5000 | 326.9 | 5041.0 | 0.82 | 112.7 |
| 2C5 | 0 | 2.1 | NaN | NaN | 1.0 |
| | 0.32 | 2.1 | 0.3 | −10.36 | 1.0 |
| | 1.6 | 3.0 | 1.7 | 6.36 | 1.4 |
| | 8 | 6.6 | 7.8 | −1.95 | 3.2 |
| | 40 | 23.4 | 40.1 | 0.18 | 11.1 |
| | 200 | 87.7 | 200.9 | 0.46 | 41.7 |
| | 1000 | 232.2 | 996.0 | −0.40 | 110.4 |
| | 5000 | 316.8 | 5043.1 | 0.86 | 150.6 |
| 19B1 | 0 | 1.7 | NaN | NaN | 1.0 |
| | 0.32 | 1.8 | 0.3 | −6.63 | 1.1 |
| | 1.6 | 2.7 | 1.7 | 4.82 | 1.6 |
| | 8 | 6.2 | 7.8 | −2.32 | 3.6 |
| | 40 | 22.8 | 40.5 | 1.20 | 13.3 |
| | 200 | 82.9 | 199.2 | −0.39 | 48.3 |
| | 1000 | 202.9 | 1001.9 | 0.19 | 118.2 |
| | 5000 | 246.3 | 4936.0 | −1.28 | 143.6 |
| 11G5 | 0 | 7.4 | NaN | NaN | 1.0 |
| | 0.32 | 7.5 | 0.4 | 10.6 | 1.0 |
| | 1.6 | 9.8 | 1.5 | −5.3 | 1.3 |
| | 8 | 20.3 | 8.0 | 0.6 | 2.7 |
| | 40 | 60.9 | 40.6 | 1.6 | 8.2 |
| | 200 | 183.7 | 196.0 | −2.0 | 24.8 |
| | 1000 | 393.7 | 1025.2 | 2.5 | 53.1 |
| | 5000 | 468.5 | 4581.7 | −8.4 | 63.3 |
| 11F9 | 0 | 3.0 | NaN | NaN | 1.0 |
| | 0.32 | 3.1 | 0.3 | −4.19 | 1.0 |
| | 1.6 | 5.0 | 1.7 | 3.47 | 1.7 |
| | 8 | 12.8 | 7.9 | −1.27 | 4.3 |
| | 40 | 45.1 | 39.8 | −0.47 | 15.2 |
| | 200 | 148.5 | 202.9 | 1.45 | 50.2 |
| | 1000 | 289.3 | 972.7 | −2.73 | 97.8 |
| | 5000 | 329.5 | 8125.0 | 62.50 | 111.4 |

Exp.: expected.
Av.: average.
Resp.: response.
Conc: concentration.

A similar Gyrolab™ assay procedure was performed and the data was then extracted and compared. At the upper end (5000 ng/ml), the Gyrolab™ capture and the rabbit mAb clones 9E6, 2C5 and 19B1 all had acceptable biases (<20) and signal-to-noise ratios greater than 100. The three rabbit anti-hIgG clones showed better signal-to-noise ratios than the Gyrolab™ capture. At 5000 ng/ml high end point, although clone 11 G5 had acceptable average bias, its signal-to-noise ratio was low (63.3%), which was caused by the relatively high blank signal level (7.4). For the same reason, the commercial mAb clone MCA5748 also had a very poor signal-to-noise ratio at the upper end (24.0).

These data suggest that clones 9E6, 2C5 and 19B1 offer a similar dynamic range when compared to the Gyrolab™ capture reagent with better signal to noise ratios. The detection dynamic range by clones 9E6, 2C5 and 19B1 was significantly better than the commercial mouse anti-hIgG clone MCA5748G. Clones 16F5, and 11F9 performed well at the 0-1000 ng/ml range, with <20% average Bias, but not at the 5000 ng/ml data point. This might be due to the fact that these two clones possess different binding epitopes from the four other clones.

Thus, in the initial Gyrolab™ assay, when the experiment was performed using clone 16F5 as the capture reagent, concentration-dependent assay curves were generated with the assay matrix containing up to 25% cynomolgus monkey serum. The assay performed well in the range of 0.30-1200 ng/ml with the assay matrix containing 4% cynomolgus monkey serum. In the expanded Gyrolab™ evaluation assays, all the six rabbit mAb clones demonstrated their capability to serve as capture reagents for the detection of both whole human IgG and Fab molecules. However, the two control capture reagents, the Gyros capture reagent and the commercial clone MCA5748G, were only able to detect the whole human IgG, but not the Fab molecule.

As summarized in Table 10, we developed six rabbit anti-human IgG mAb clones that can bind to both the whole human IgG molecule and the Fab molecule, without binding to cynomolgus monkey IgG. These six clones belong to three different epitope groups and are different from the commercial clone MCA5748G. Each of these clones have been tested for detection of human IgGs and Fabs in Gyrolab™ assays, and three of them exhibited greater dynamic range and signal to noise ratio.

TABLE 10

Summary of six rabbit anti-hIgG clones

| Antibody clones | hIgG | hFab | cynoIgG | Epitope | VH Phylogenetic Tree |
|---|---|---|---|---|---|
| Gyros Capture | Yes | No | No | Unknow | N/A |
| MCA5748G | Yes | No | minor | Unknow | N/A |
| 16F5 | Yes | Yes | No | Group A | Group A |
| 11F9 | Yes | Yes | No | Group B | Group B |
| 9E6 | Yes | Yes | No | Group C | Group C |
| 2C5 | Yes | Yes | No | Group C | Group C |
| 19B1 | Yes | Yes | No | Group C | Group C |
| 11G5 | Yes | Yes | No | Group C | Group C |

Example 6: Use of Rabbit Anti-Human IgG Monoclonal Antibody Clones as Generic Positive Control for PandA Assay Rabbit polyclonal anti-drug antibodies (pAb) are commonly used as the performance controls for anti-drug antibody (ADA) detection. But the generation of pAb is time consuming and requires repetitive use of experimental animals. Furthermore, pAb often shows low sensitivity as a control. This Example describes a study comparing two recombinantly produced rabbit anti-human IgG mAbs, 2C5 and 11 G5, and a commercial mouse anti-Fc mAb (JDC-10; Southern Biotech Cat #9040-01) as a positive control in a PandA assay.

2C5 and 11 G5, along with JDC-10, were diluted in monkey plasma pool at 5 µg/ml, 1 µg/ml, 0.75 µg/ml, 0.5 µg/ml, and 0 µg/ml, respectively.

Plasma samples containing diluted antibody were initially diluted 1:5 in assay buffer (300 mM Acetic acid, 2% BSA) containing excess drug (a monoclonal antibody of human IgG4 isotype; 10-50 µg/mL) and incubated for one hour at 37° C. with 450 rpm in a polypropylene plate to allow complexes to form between the drug and the added antibody in the sample. This was followed by the addition of 3% PEG in borate (pH 8.0) to each sample and an overnight incubation at 2-8° C. The final concentration of PEG buffer in each sample was 1.5%.

On the following day, the plate was centrifuged at 4,000 rpm for 20 minutes to precipitate the complexes into a pellet. The pellet was re-suspended with 1.5% PEG in borate (pH 8.0) and centrifuged for a second time at 4,000 rpm for 20 minutes. The wash cycle was repeated three times. Following the final centrifugation, each sample was suspended in 100 µl of 300 mM acetic acid and further diluted 1:10 (20 µl sample+180 µl acetic acid) for a final sample dilution of 1:50. Diluted samples were added in duplicate to the wells of an MSD High Bind plate at 25 µl per well and incubated for one hour at 24° C. with shaking at 450 rpm.

Following the incubation, the plate was washed with 1× plate wash buffer and blocked with 3% milk in PBS for one hour at 24° C. with shaking. The plate was then washed and 100 ng/ml of sulfo-TAG-Drug was added to the samples and incubated for one hour at 24° C. with shaking. After the final incubation, the plate was washed with 0.05% Tween in PBS. Read buffer T 2× was then added and the plate was read on a Sector PR2400. The electrochemiluminescence (ECL) signal was proportional to the anti-drug antibody in each sample.

Figure 6A:
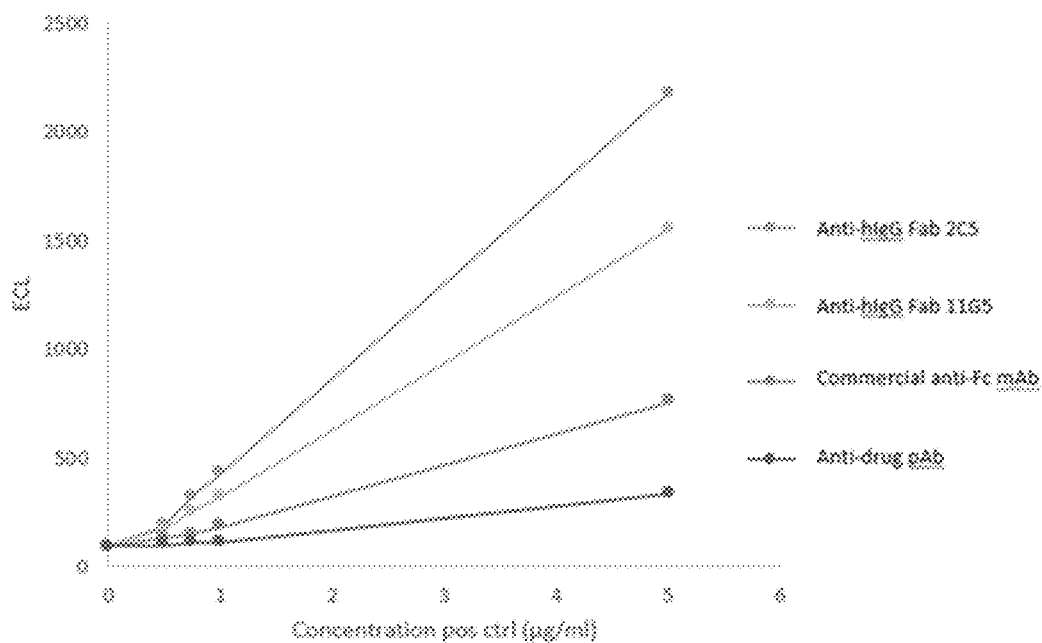
FIG. 6A shows a comparison of four antibodies used in a precipitation and acid dissociation (PandA) assay. The dynamic range and sensitivity of two rabbit anti-human IgG clones, 2C5 and 11 G5, were compared with a commercial mouse anti-Fc mAb, clone JDC-10 (Southern Biotech, Cat. No. 9040-01). pAb: a rabbit polyclonal anti-drug antibody (drug: a monoclonal antibody with a human IgG4 constant region). ECL: electrochemiluminescence.

As shown in FIG. 6A and Table 11, the two rabbit anti-hIgG clones 2C5 and 11 G5 demonstrated a greater dynamic range and sensitivity compared to the commercial anti-Fc mAb clone JDC-10.

TABLE 11

Comparison of Different Antibodies as Positive Control in PandA

| PC (µg/ml) | ECL Signal | | |
|---|---|---|---|
| | Anti-Fc mAb JDC-10 | Anti-hFab mAb 2C5 | Anti-hFab mAb 11G5 |
| 5 | 755.5 | 2,180 | 1,551 |
| 1 | 182.5 | 426 | 319.5 |
| 0.75 | 148.5 | 323 | 257 |
| 0.5 | 130.5 | 187.5 | 171 |
| NC | 95 | 94.5 | 95 |
| S/N | 1.37 | 1.98 | 1.80 |

*PC: positive control.
S/N: signal to noise.
NC: negative control.

Figure 6B:
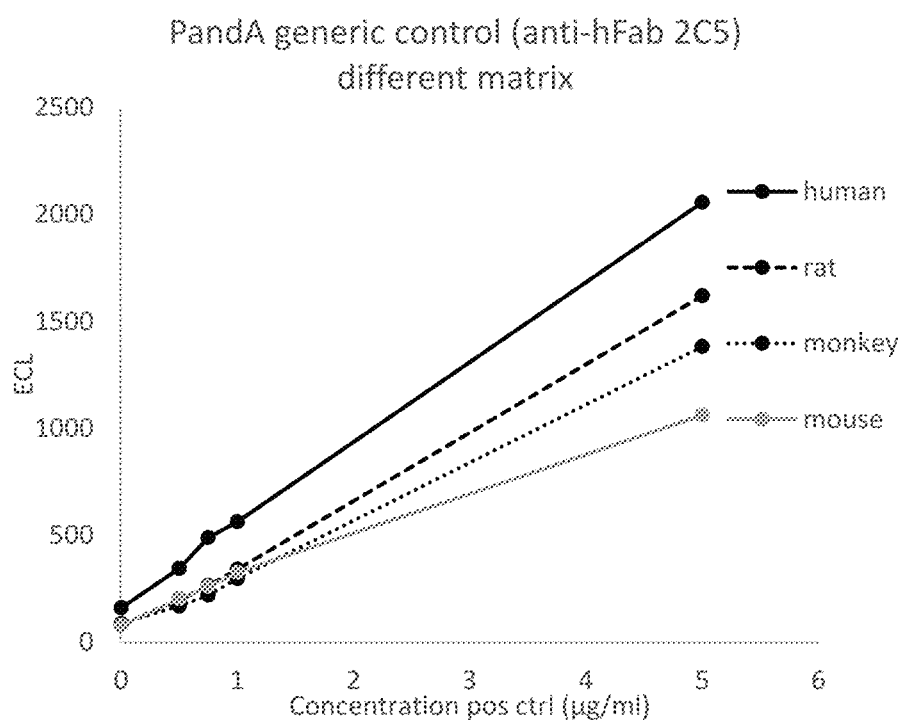
FIGS. 6B and 6C show the performance of clones 2C5 and 11 G5, respectively, in human, rat, monkey, and mouse serum matrices in a PandA assay. Pos ctrl: positive control.
Figure 6C:
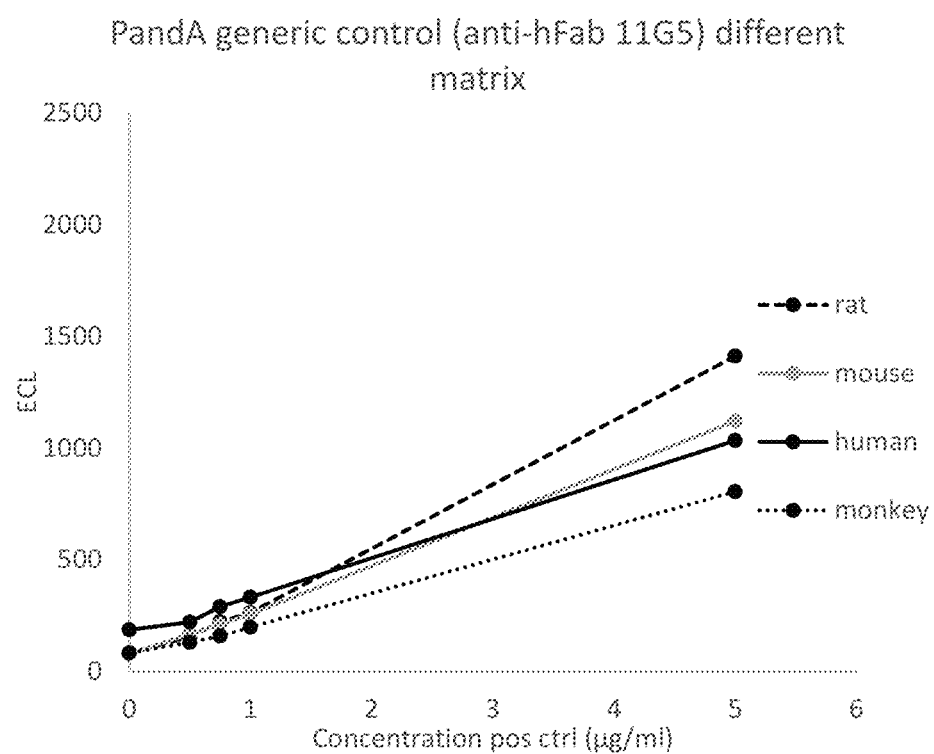

Clones 2C5 and 11 G5 also served as performance controls and were tested in human, rat, monkey, and mouse plasma and serum matrices. The data show that both 2C5 (FIG. 6B) and 11 G5 (FIG. 6C) could distinguish between human, monkey, mouse, and rat sera, with 2C5 being more sensitive than 11 G5 (Table 12). In the human matrix, the background increased for both clones as expected.

TABLE 12

Sensitivity in PandA Assay

| PC (µg/ml) | S/N (monkey) | |
|---|---|---|
| | 2C5 | 11G5 |
| 5 | 15.70 | 9.76 |
| 1 | 3.39 | 2.40 |
| 0.75 | 2.51 | 1.92 |
| 0.5 | 1.93 | 1.58 |

The above results demonstrate that recombinantly produced rabbit anti-human IgG mAbs are an excellent generic positive control for preclinical assays, especially for the PandA format (e.g., for monkey, rat, and mouse matrices). These antibodies performed well in both plasma and serum matrices. The rabbit IgG mAbs have an improved dynamic range and assay sensitivity.

The invention claimed is:

1. An isolated monoclonal antibody or an antigen-binding portion thereof that binds specifically to human IgG, wherein the antibody or portion comprises heavy chain complementarity-determining region (CDR) 1-3 and light chain CDR1-3 respectively comprising
SEQ ID NOs: 27-32,
SEQ ID NOs: 33-38,
SEQ ID NOs: 39-44,
SEQ ID NOs: 45-50,
SEQ ID NOs: 51-56, or
SEQ ID NOs: 57-62.

2. The monoclonal antibody or antigen-binding portion of claim 1, wherein the antibody or portion comprises heavy chain variable domain (VH) and light chain variable domain (VL) respectively comprising
SEQ ID NOs: 13 and 19,
SEQ ID NOs: 14 and 20,
SEQ ID NOs: 15 and 21,
SEQ ID NOs: 16 and 22,
SEQ ID NOs: 17 and 23, or
SEQ ID NOs: 18 and 24.

3. The monoclonal antibody of claim 1, wherein the antibody is a rabbit IgG antibody.

4. The monoclonal antibody of claim 1, comprising a heavy chain constant region amino acid sequence of SEQ ID NO: 25, and/or a light chain constant region amino sequence of SEQ ID NO: 26.

5. The monoclonal antibody of claim 1, comprising a heavy chain and a light chain having the amino acid sequences of
SEQ ID NOs: 63 and 69,
SEQ ID NOs: 64 and 70,
SEQ ID NOs: 65 and 71,
SEQ ID NOs: 66 and 72,
SEQ ID NOs: 67 and 73, or
SEQ ID NOs: 68 and 74,
respectively, with or without the leader sequences.

6. The monoclonal antibody or antigen-binding portion of claim 1, further comprising a detectable label.

7. A composition or a kit comprising the monoclonal antibody or antigen-binding portion of claim 1 in an aqueous buffered solution.

8. An isolated nucleic acid molecule encoding the heavy chain, the light chain, or both, of the monoclonal antibody or antigen-binding portion of claim 1.

9. The nucleic acid molecule of claim 8, comprising SEQ ID NOs: 1, 2, 3, 4, 5, 6, 7, 8, 9, 10, 11, and/or 12.

10. The nucleic acid molecule of claim 9, comprising
SEQ ID NOs: 1 and 7,
SEQ ID NOs: 2 and 8,
SEQ ID NOs: 3 and 9,
SEQ ID NOs: 4 and 10,
SEQ ID NOs: 5 and 11, or
SEQ ID NOs: 6 and 12.

11. An expression construct comprising the nucleic acid molecule of claim 8.

12. A host cell comprising nucleotide sequences encoding the heavy chain and the light chain of the monoclonal antibody or antigen-binding portion of claim 1.

13. The host cell of claim 12, wherein the host cell is a mammalian cell.

14. A method of producing an antibody or an antigen-binding portion thereof, comprising:
culturing the host cell of claim 13 under conditions that allow expression of the heavy chain and light chain of the antibody or portion, and
isolating the antibody or portion from the cultured cell or the supernatant of the cell culture.

15. A method of detecting human IgG or a fragment thereof in a sample, comprising contacting the sample with one or more monoclonal antibodies or antigen-binding portions of claim 1.

16. The method of claim 15, wherein the sample is obtained from an animal that has been administered an antibody comprising a human IgG constant region or a fragment thereof.

17. The method of claim 15, wherein the human IgG constant region is a human IgG1, IgG2, IgG3, or IgG4 constant region.

18. The method of claim 15, wherein the animal has been administered a Fab or F(ab') 2 fragment of an antibody comprising a human IgG1, IgG2, IgG3, or IgG4 constant region.

19. The method of claim 15, wherein the sample is a tissue sample.

20. The method of claim 15, wherein the animal is a non-human primate.

21. The method of claim 19, wherein the tissue sample is a blood, serum, or plasma sample.

22. The method of claim 20, wherein the non-human primate is a cynomolgus monkey or rhesus monkey.

* * * * *

UNITED STATES PATENT AND TRADEMARK OFFICE
CERTIFICATE OF CORRECTION

Page 1 of 1

PATENT NO. : 12,215,171 B2
APPLICATION NO. : 17/335291
DATED : February 4, 2025
INVENTOR(S) : Chu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 854 days.

Signed and Sealed this
Second Day of September, 2025

Coke Morgan Stewart
*Acting Director of the United States Patent and Trademark Office*